(12) United States Patent
Eisenbach et al.

(10) Patent No.: US 7,795,224 B2
(45) Date of Patent: Sep. 14, 2010

(54) TUMOR ASSOCIATED ANTIGEN PEPTIDES AND USE OF SAME AS ANTI-TUMOR VACCINES

(75) Inventors: Lea Eisenbach, Rehovot (IL); Erez Bar-Haim, Yavne (IL); Adrian Paz, Petach Tikva (IL); Matityahu Fridkin, Rehovot (IL); Cheryl Fitzer-Attas, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 12/326,675

(22) Filed: Dec. 2, 2008

(65) Prior Publication Data

US 2009/0136462 A1  May 28, 2009

Related U.S. Application Data

(62) Division of application No. 11/391,476, filed on Mar. 29, 2006, now Pat. No. 7,531,629, which is a division of application No. 09/744,804, filed as application No. PCT/IL99/00417 on Jul. 29, 1999, now Pat. No. 7,084,249.

(30) Foreign Application Priority Data

Jul. 30, 1998  (IL)  ..................................... 125608

(51) Int. Cl.
*A61K 38/00* (2006.01)
(52) U.S. Cl. .......................................... 514/15; 530/328
(58) Field of Classification Search ........................ None
See application file for complete search history.

(56) References Cited

U.S. PATENT DOCUMENTS

| 5,455,031 | A | 10/1995 | Ceriani et al. |
| 5,840,839 | A | 11/1998 | Wang et al. |

FOREIGN PATENT DOCUMENTS

| DE | 19516673 A1 | 10/1996 |
| DE | 19758400 A1 | 7/1999 |
| WO | WO94/20127 | 9/1994 |
| WO | WO95/04548 | 2/1995 |
| WO | WO95/15171 | 6/1995 |
| WO | WO95/19783 | 7/1995 |
| WO | WO97/08318 | 3/1997 |
| WO | WO97/11715 | 4/1997 |
| WO | WO97/35021 | 9/1997 |
| WO | WO98/43084 | 10/1998 |

OTHER PUBLICATIONS

Peshwa et al., Induction of prostate tumor-specific CD8+cytotoxic T-lymphocytes in vitro using antigen-presenting cells pulsed with prostatic acid phosphatase peptide, *The Prostate*, 36:129-138 (1998).
Salgaller et al., Report of immune monitoring of prostate cancer patients undergoing T-cell therapy using dendritic cells pulsed with HLA-A2-Specific peptides from prostate-specific membrane antigen (PSMA), *The Prostate*, 35:144-151 (1998).
Nseyo et al., Immunotherapy of Bladder Cancer, *Seminars in Surgical Oncology*, 13:342-349 (1997).
Urban et al., Tumor Antigens, *Annu. Rev. Immunol.*, 10:617-44 (1992).
Acres et al., Vaccinia Virus MUC1 Immunization of Mice: Immune Response and Protection Against the Growth of Murine Tumors Bearing the MUC1 Antigen, *Journal of Immunotherapy*, 14:136-143 (1993).
Gjertsen et al., Ex vivo ras Peptide Vaccination in Patients with Advanced Pancreatic Cancer: Results of A Phase I/II Study, *Int. J. Cancer*, 65:450-453 (1996).
Murphy et al., Phase I Clinical Trial: T-Cell Therapy for Prostate Cancer Using Autologus Dendritic Cells Pulsed With HLA-A0201-Specific Peptides from Prostate-Specific Membrane Antigen, *The Prostate*, 29:371-380 (1996).
Xue et al., Induction of Human Cytotoxic T Lymphocytes Specific for Prostate-Specific Antigen, *The Prostate*, 30:73-78 (1997).
Correale et al., In Vitro Generation of Human Cytotoxic T Lymphocytes Specific for Peptides Derived From Prostate-Specific Antigen, *Journal of the National Cancer Institute*, 89(4)293-300 (1997).
Tjoa et at, Presentation of Prostate Tumor Antigens by Dendritic Cells Stimulates T-Cell Proliferation and Cytotoxicity, *The Prostate*, 28:65-69 (1996).
Barnd et al., Specific, Major Histocompatibility Complex-Unrestricted Recognition of Tumor-Associated Mucins by Human Cytotoxic T Cells, *Proc. Natl. Acad. Sci. USA*, 86:7159-7163 (1989).
Agrawal et al., In Vitro Induction of MUC-1 Peptide-Specific Type 1 T Lymphocyte and Cytotoxic T Lymphocyte Responses from Healthy Multiparous Donors, *The Journal of Immunology*, 157:2089-2095 (1996).
Couto et a., Anti-BA46 Monoclonal Antibody Mc3: Humanization Using A Novel Positional Consensus and In Vivo and In Vitro Characterization, *Cancer Research*, 55:1717-1722 (1995).
Domenech et al., In Vito Studies of MHC-Restricted Recognition of A Peptide From the MUC1 Tandem Repeat Domain by CTL, *FASEB J.*, 9:A1023, (1995).
Apostolopoulos et al., Induction of HLA-A2-Restricted CTLs to the Mucin 1 Human Breast Cancer Antigen, *The Journal of Immunology*, 159:5211-5218 (1997).

(Continued)

*Primary Examiner*—Sheela J Huff
(74) *Attorney, Agent, or Firm*—Browdy and Neimark, PLLC

(57) ABSTRACT

The present invention relates to tumor associated antigen (TAA) peptides and to use of same, of polynucleotides encoding same and of cells presenting same as anti-tumor vaccines. More particularly, the present invention relates to tumor associated antigen peptides derived from Uroplakin Ia, Ib, II and III, Prostate specific antigen (PSA), Prostate acid phosphatase (PAP) and Prostate specific membrane antigen (PSMA), BA-46 (Lactadherin), Mucin (MUC-1), and Teratocarcinoma-derived growth factor (CRIPTO-1) and the use of same as anti-tumor vaccines to prevent or cure bladder, prostate, breast or other cancers, carcinomas in particular. Most particularly, the present invention relates to tumor associated antigen peptides which are presentable to the immune system by HLA-A2 molecules.

8 Claims, 29 Drawing Sheets

OTHER PUBLICATIONS

Weinstein B: "Chemistry and Biochemistry of Amino Acids, Peptides and Proteins, Passage" Chemistry and Biochemistry of Amino Acids, Peptides, and Proteins, XX,XX, vol. 7, p. 266-357 XP002032461, 1982.
Stubbs at al., *Proc. Natl. Acad. Sci. USA*, 87:8417-8421 (1990).
Sherman et al., *Critical reviews in Immunol.*, 18(1-2)47-54 (1998).
Ezzell, *NIH Res.*, 7:46-49 (1995).
Spitler, *Cancer Biotherapy*, 10:1-3 (1995).
Boon, *Adv. Can. Res.*, 58:177-210 (1992).
Gura, *Science*, 278:1041-1042 (1997).
Jain, *Sci. Am.*, 271:58-65 (1994).
Curti, *Crit. Rev. in Oncology/Hematology*, 14:29-39 (1993).
Hartwell et al., *Science*, 278:1064-1068 (1997).
Larocca et al., *Cancer Res.*, 51:4994-4998 (1991).
Riott et al., *Immunology*, Fourth Edition, Mosby, p. 7.9 col. 1 lines 1-10 (1996).
McMurry, *Organic Chemistry*, p. 65 only (1988).
Belllone et al., *J. Immunol.*, 165:2651-6 (Sep. 1, 2000).
Guagler et al., *J. Exp. Med.*, 179:921-930 (1994).
Born, *Adv. Can. Res.*, 58:177-210 (1992).
Bodey et al., *Anticancer Research*, 20:2665-2676 (2000).
DeGruijl et al., *Nature Medicine*, 5410:1124-1125 (Oct. 1999).
Ezzell, *J. NIH Res.*, 7:46-49 (1995).

TUMOR ASSOCIATED ANTIGEN PEPTIDES AND USE OF SAME AS ANTI-TUMOR VACCINES

CROSS-REFERENCE TO RELATED APPLICATIONS

The present application is a division of application Ser. No. 11/391,476, filed Mar. 29, 2006, which is a division of application Ser. No. 09/744,804, now issued as U.S. Pat. No. 7,084,249, which is a 371 national stage application of PCT/IL99/00417, filed Jul. 29, 1999. The entire content of these applications are incorporated herein by reference.

FIELD AND BACKGROUND OF THE INVENTION

The present invention relates to tumor associated antigen (TAA) peptides and to the use of same, of polynucleotides encoding same and of cells presenting same as anti-tumor vaccines. More particularly, the present invention relates to tumor associated antigen peptides derived from Uroplakin Ia, Ib, II and III, Prostate specific antigen (PSA), Prostate acid phosphatase (PAP) and Prostate specific membrane antigen (PSMA), BA-46 (Lactadherin), Mucin (MUC-1), and Teratocarcinoma-derived growth factor (CRIPTO-1) and the use of same as anti-tumor vaccines to prevent or cure bladder, prostate, breast or other cancers, carcinomas in particular. Most particularly, the present invention relates to tumor associated antigen peptides which are presentable to the immune system by HLA-A2 molecules.

Local therapy such as surgical excision or ablation by radiation is a mainstay for the treatment of primary cancer and is curative for a percentage of patients. However, many malignancies will recur locally or at a distant site. Thus the prevention or cure of metastases remains a major focus in clinical oncology (1). Although early detection followed by surgery provides good prognosis for a number of major cancer types, a large fraction of patients would need adjuvant therapy. Part of these patients will, with time, succumb to metastasis (2-4). Alternative approaches based on gene therapy and immunotherapy have been the focus of attention in the last years. One such approach is specific active immunotherapy (SAI, 5). The objective of SAI is to stimulate a tumor specific cytotoxic T lymphocytes (CTL) immune response that is capable of eliminating residual metastatic disease and induce a state of immunity to protect the patients from recurrent disease. The underlying assumption of SAI is that tumor cells express tumor antigens which are sufficiently distinct in structure or context to induce an effective CTL response (6). Although the validity of these assumptions was questioned, a number of studies in the last decade have demonstrated the rational of SAI. In a landmark study, van Pel and Boon have shown that tumor associated antigens (TAAs) can be isolated and defined (7). Importantly, ex-vivo manipulations of "non-immunogenic" animal tumor cells can be used to elicit effective immune responses which will also recognize parental "non-immunogenic" tumor cells (8). Studies employing rodent tumor models with little intrinsic immunogenicity have shown that genetically modified tumor cells transduced to express MHC class I, cytokines such as IL-1, IL-2, IL-4, IL-6, IL-7, IL-12, γIFN or GM-CSF or costimulatory molecules such as B7-1 or B7-2 were capable of preventing or causing regression of tumors or metastases (reviewed in 9). Although gene modified tumor vaccine (GMTV) clinical trials, with improved retroviral vectors or other transfer methodologies are currently tested, it becomes clear that GMTV using autologous tumor cells might be limited by its complexity, high cost and ineffective gene transfer methodologies (10). One alternative approach would be vaccination with tumor associated antigens (TAAs) presented in an effective way to the patient's immune system, to induce antigen specific CTL (11).

Cytotoxic T lymphocytes (CTL), directed against peptides presented by MHC class I molecules, constitute powerful effectors of the immune system against tumors or infectious agents (12). These peptides are usually 8-10 amino acids long with 2-3 primary anchor residues that interact with the MHC class I molecules and 2-3 amino acid residues which bind to the T cell receptor (13). Several methods have been employed to identify CTL epitopes. If the amino acid sequence of a protein antigen is known, like in the case of viral proteins, oncogenes, suppressor genes or growth factor receptors, overlapping peptides of 8-10 amino acids in length can be synthesized and screened as CTL targets (14). CTL epitopes may also be identified subsequent to the search for MHC binding motifs in known proteins (15). If the tumor antigen is not known, isolation of the TAA peptides from total acid extract or from MHC class I molecules followed by HPLC fractionation steps and Edman sequencing (16) or mass spectrometry (17) provide a direct way of identifying CTL epitopes. Recently, a synthetic combinatorial library approach, in which defined amino acids in two MHC anchor positions are fixed and all other positions are subgrouped for CTL screening has led to the description of novel EL4 TAA peptide mimotopes (18).

The most fruitful method, so far, designed by T. Boon and his colleagues is the genetic approach in which cDNA expression libraries are pool transfected into COS7 cells with the appropriate HLA and screened by CTL lines. This approach led to the discovery of several human melanoma and mouse mastocytoma antigens recognized by specific CTL (19). The first report of a phase I clinical trial with the synthetic MAGE3 melanoma peptide, restricted by HLA-A1, showed regression of cutaneous, subcutaneous and lung metastases in 3/6 patients (20). Recently, two reports of clinical trials have shown that treatment of patients with a melanoma gp100 TAA peptide together with IL-2 resulted in significant tumor regression in 13/31 (42%) patients and that vaccination with defined peptides or total peptide extracts on autologous dendritic cells (DC) resulted in complete or partial cures (21, 22). Regression of lung carcinoma established metastases or small established tumors was demonstrated in a murine model by peptide vaccination (23, 24). These observations suggest that TAA peptide vaccines may constitute a reasonable therapeutic modality in advanced cancer. In studies with murine tumors, CTL are induced in vivo by immunization with irradiated tumor cells, often gene modified by MHC class I; cytokine or costimulatory molecules like B7-1 or B7-2 genes (16, 18, 25). In melanomas, CTL lines were mostly induced from peripheral blood mononuclear cells (PBMC) of patients or from tumor infiltrated lymphocytes (TIL, 19, 26). Yet, most metastatic tumors are non-immunogenic tumors and it is extremely difficult to derive CTL lines or clones from TIL or patient's PBL. Moreover, in vitro propagated CTL clones do not always represent dominant anti-tumor specificities but rather sporadic clones surviving culture conditions. Lately, a number of studies have compared the CTL repertoire of viral or other defined peptides, restricted by HLA-A2.1 in human PBL from HLA-A2.1 expressing patients to CTL induced in HLA-A2.1 transgenic mice. Good concordance between human HLA-A2.1 and murine transgenie HLA-A2.1 CTL repertoire was found, confirming the potential of such transgenics in identification of human CTL epitopes (27).

Although vaccination with defined peptides of HLA transgenic mice shows an overlapping repertoire to human CTL, vaccination of such mice with multi-epitope proteins shows that murine H-2 restricted responses are dominant and obliterate, as a rule, cytolytic responses with direct recognition of human HLA (28). Thus, by combining classical HLA class I transgenesis with selective destruction of murine H-2, it is possible to derive useful mouse strains for the study of HLA class I restricted responses. While reducing the present invention to practice, we utilized such mice for preparation of anti-tumor CTL as a tool for TAA purification and as a model system to assess the immunogenicity of peptides.

Murine H-2 knockout mice transgenic for a single human HLA seem to be a suitable model for induction of anti-tumor CTL. Classical $\beta_2$ microglobulin knockout mice ($\beta_2$m–/–) do not express H-2 $K^b$ or other non-classical class I molecules, yet they express low levels of H-2 $D^b$ heavy chain in the absence of $\beta_2$m. To derive fully H-2 knockout mice, Prof. F. Lemonnier (Pasteur Institute, Paris), prepared H-2 $D^{b-/-}$ mice. These mice were crossed with $\beta 2m^{-/-}$ mice and bred to derive homozygous $\beta_2 m^{-/-}$, $D^{b-/-}$ mice that do not express any H-2 class I. These mice are practically depleted of $CD8^+$ splenocytes, as well as other $CD8^+$ cells. To reconstitute in these mice expression of a stable HLA-A2.1, expression of $\beta_2$m is necessary. A construct containing a leader sequence, domains α1 and α2 of HLA-A2.1 and α3, transmembrane and cytoplasmic domains of H-2 $D^b$ fused to human $\beta_2$m (HhD) was prepared. The exchange of the α3 human domain by a murine domain in HhD is thought to improve the interaction of the class I molecule with CD8 molecules of the murine CTL (29). This HhD construct was transfected into RMA and RMA-S cells and shown to bind HLA-A2.1 restricted peptides. The HhD construct was used to produce transgenic mice in C57BL/6 recipients and positive founder mice were bred to the $\beta_2 m^{-/-}$, $D^{b-/-}$ mice (30).

The $\beta_2 m^{-/-}$, $D^{b-/-}$, $HhD^{-/+}$ heterozygous mice show reconstitution of $CD8^+$ cells in the periphery relative to $\beta_2 m^{-/-}$ $D^{b-/-}$ mice. Moreover, preliminary data from Prof. Lemonnier's lab showed that CTL induced in HhD mice against influenza NP are directed to the same HLA-A2 dominant epitope as in the human repertoire. Homozygous HhD mice were derived and a colony was established in the Weizmann Institute of Science, Israel.

SUMMARY OF THE INVENTION

According to one aspect of the present invention there is provided a peptide derived from a protein selected from the group consisting of Uroplakin (UP), Prostate specific antigen (PSA), Prostate specific membrane antigen (PSMA), Prostate acid phosphatase (PAP), Lactadherin (BA-46) and Mucin (MUC1), and Teratocarcinoma-derived growth factor (CRIPTO-1), the peptide comprising 8 to 10 amino acid residues, of which a second residue from an amino terminal of the peptide and a carboxy terminal residue of the peptide are hydrophobic or hydrophilic natural or non natural amino acid residues, for example, SEQ ID NOs:1-64 and 65 to 77.

According to further features in preferred embodiments of the invention described below, the peptide is derived from Uroplakin, such as Uroplakin II, Uroplakin Ia, Uroplakin III and Uroplakin Ib, for example, SEQ ID NOs:1-19 or 50-64.

According to still further features in the described preferred embodiments the peptide is derived from the Prostate specific antigen (PSA), for example, SEQ ID NOs:20-24.

According to still further features in the described preferred embodiments the peptide is derived from the Prostate specific membrane antigen (PSMA), for example, SEQ ID NOs:25-30.

According to still further features in the described preferred embodiments the peptide is derived from the Prostate acid phosphatase (PAP), for example, SEQ ID NOs:31-34.

According to still further features in the described preferred embodiments the peptide is derived from the Mucin, for example, SEQ ID NOs:42-49.

According to still further features in the described preferred embodiments the peptide is derived from a non tandem repeat array of the Mucin.

According to still further features in the described preferred embodiments the peptide is derived from a region selected from the group consisting of a signal peptide, a cytoplasmic domain and an extracellular domain of the Mucin.

According to still further features in the described preferred embodiments the peptide is derived from the Lactadherin (BA-46), for example, SEQ ID NOs:35-41.

According to still further features in the described preferred embodiments, the peptide is derived from the Teratocarcinoma-derived growth factor (CRIPTO-1), for example, SEQ ID NOs. 66 to 77.

According to still further features in the described preferred embodiments the Uroplakin (UP), Prostate specific antigen (PSA), Prostate specific membrane antigen (PSMA), Prostate acid phosphatase (PAP), Lactadherin (BA-46) and Mucin (MUC1) and Teratocarcinom-derived growth factor (CRIPTO-1) are each independently of mammalian origin.

According to still further features in the described preferred embodiments the mammal is selected from the group consisting of a humanoid and a rodent.

According to still further features in the described preferred embodiments the peptide includes at least one non-natural modification.

According to still further features in the described preferred embodiments the peptide includes at least one non-natural modification rendering peptides more immunogenic or more stable.

According to still further features in the described preferred embodiments the at least one modification is selected from the group consisting of peptoid modification, semipeptoid modification, cyclic peptide modification, N terminus modification, C terminus modification, peptide bond modification, backbone modification and residue modification.

According to another aspect of the present invention there is provided a pharmaceutical composition comprising, as an active ingredient, at least one peptide at set forth herein and a pharmaceutically acceptable carrier.

According to another aspect of the present invention there is provided a vaccine composition comprising, as an active ingredient, at least one peptide at set forth herein and a vaccination acceptable carrier.

According to still further features in the described preferred embodiments the carrier is selected from the group consisting of a proteinaceous carrier to which the at least one tumor associated antigen peptide is linked, an adjuvant, a protein or a recombinant protein and an antigen presenting cell.

According to still further features in the described preferred embodiments the composition, pharmaceutical or vaccine, is effective in prevention or cure of cancer or carcinoma metastases.

According to still further features in the described preferred embodiments the cancer is selected from the group consisting of breast, bladder, prostate, pancreas, ovary, thyroid, colon, stomach and head and neck cancer.

According to still further features in the described preferred embodiments the cancer is a carcinoma.

Further according to the present invention there is provided a method of prevention or cure of a cancer or of metastases thereof comprising the step of administering to a patient an effective amount of the pharmaceutical composition described herein.

Still further according to the present invention there is provided a method of prevention or cure of a cancer or of metastases thereof comprising the step of vaccinating a patient with an effective amount of the vaccine composition described herein.

According to yet another aspect of the present invention there is provided a polynucleotide encoding at least one peptide as set forth herein. One ordinarily skilled in the art would know how to reverse translate any of the peptides according to the present invention such as the peptides set forth in SEQ ID NOs:1-64 and 66 to 77, using, for example, the human preferred codon usage, to derive the sequences of the polynucleotides according to the present invention. Such polynucleotides are readily synthesisable using the well known solid phase technology for preparation of oligonucleotides such as oligodeoxynucleotides or analogs thereof.

According to still further features in the described preferred embodiments the polynucleotide forms a part of a longer polynucleotide designed to encode a fused protein product from which at least one peptide is cleavable by a protease.

According to a further aspect of the present invention there is provided a pharmaceutical composition comprising, as an active ingredient, at least one polynucleotide at set forth herein and a pharmaceutically acceptable carrier.

According to still a further aspect of the present invention there is provided a cellular vaccine composition comprising an antigen presenting cell presenting at least one peptide derived from a protein selected from the group consisting of Uroplakin (UP), Prostate specific antigen (PSA), Prostate specific membrane antigen (PSMA), Prostate acid phosphatase (PAP), Lactadherin (BA-46) Mucin (MUC1) and Teratocarcinoma-derived growth factor (CRIPTO-1), the at least one peptide comprising 9 or 10 amino acid residues, of which a second residue from an amino terminal of the peptide and a carboxy terminal residue of the peptide are hydrophilic or aliphatic non-charged natural or synthetic amino acid residues.

According to still further features in the described preferred embodiments the antigen presenting cell is selected from the group consisting of a dendritic cell, a macrophage, a B cell and a fibroblast.

According to still further features in the described preferred embodiments the antigen presenting cell is caused to present the at least one tumor associated antigen peptide by a method selected from the group consisting of (a) genetically modifying the antigen presenting cell with at least one polynucleotide encoding the at least one tumor associated antigen peptide such that the said peptide or at least one longer polypeptide including said peptide will be expressed; (b) loading the antigen presenting cell with at least one polynucleotide encoding the at least one tumor associated antigen peptide; (c) loading the antigen presenting cell with the at least one tumor associated antigen peptide; and (d) loading the antigen presenting cell with at least one longer polypeptide including the at least one tumor associated antigen peptide.

According to a still further aspect of the present invention there is provided a pharmaceutical composition also comprising a helper peptide.

According to a still further aspect of the present invention there is provided a pharmaceutical composition, wherein the helper peptide has a T helper epitope.

According to a still further aspect of the present invention there is provided a vaccine composition also comprising a helper peptide.

According to a still further aspect of the present invention there is provided a vaccine composition, wherein the helper peptide has a T helper epitope.

According to a still further aspect of the present invention there is provided a use of the at least one peptide in the manufacture of a medicament.

According to a still further aspect of the present invention there is provided the at least one peptide for use as a medicament.

According to a still further aspect of the present invention there is provided a use of the at least one peptide in the manufacture of a medicament for the prevention or cure of a cancer or cancer metastases.

According to a still further aspect of the present invention there is provided the at least one peptide for use as a medicament for the prevention or cure of a cancer or cancer metastases.

According to a still further aspect of the present invention there is provided a peptide derived from a protein selected from the group consisting of Uroplakin (UP), Prostate specific antigen (PSA), Prostate specific membrane antigen (PSMA), Prostate acid phosphatase (PAP), Lactadherin (BA-46) and Mucin (MUC1) and Teratocarcinoma-derived growth factor (CRIPTO-1), the peptide comprising 8-10 amino acid residues as selected so as to promote effective binding to a MHC class 1 type molecule such that a CTL response is elicitable.

The present invention successfully addresses the shortcomings of the presently known configurations by providing novel tumor associated antigen peptides effective in eliciting CTL response which may therefore be effective therapeutic agents to combat cancer.

BRIEF DESCRIPTION OF THE DRAWINGS

The invention herein described, by way of example only, with reference to the accompanying drawings, wherein:

In FIGS. 23a-d peptides were loaded onto target cells at a concentration of 200 µM. For FIG. 23e two concentrations of peptide were used for loading (20 µM and 200 µM). The protein origins of the peptides examined are listed in Table 3.

DESCRIPTION OF THE PREFERRED EMBODIMENTS

Figure 1:
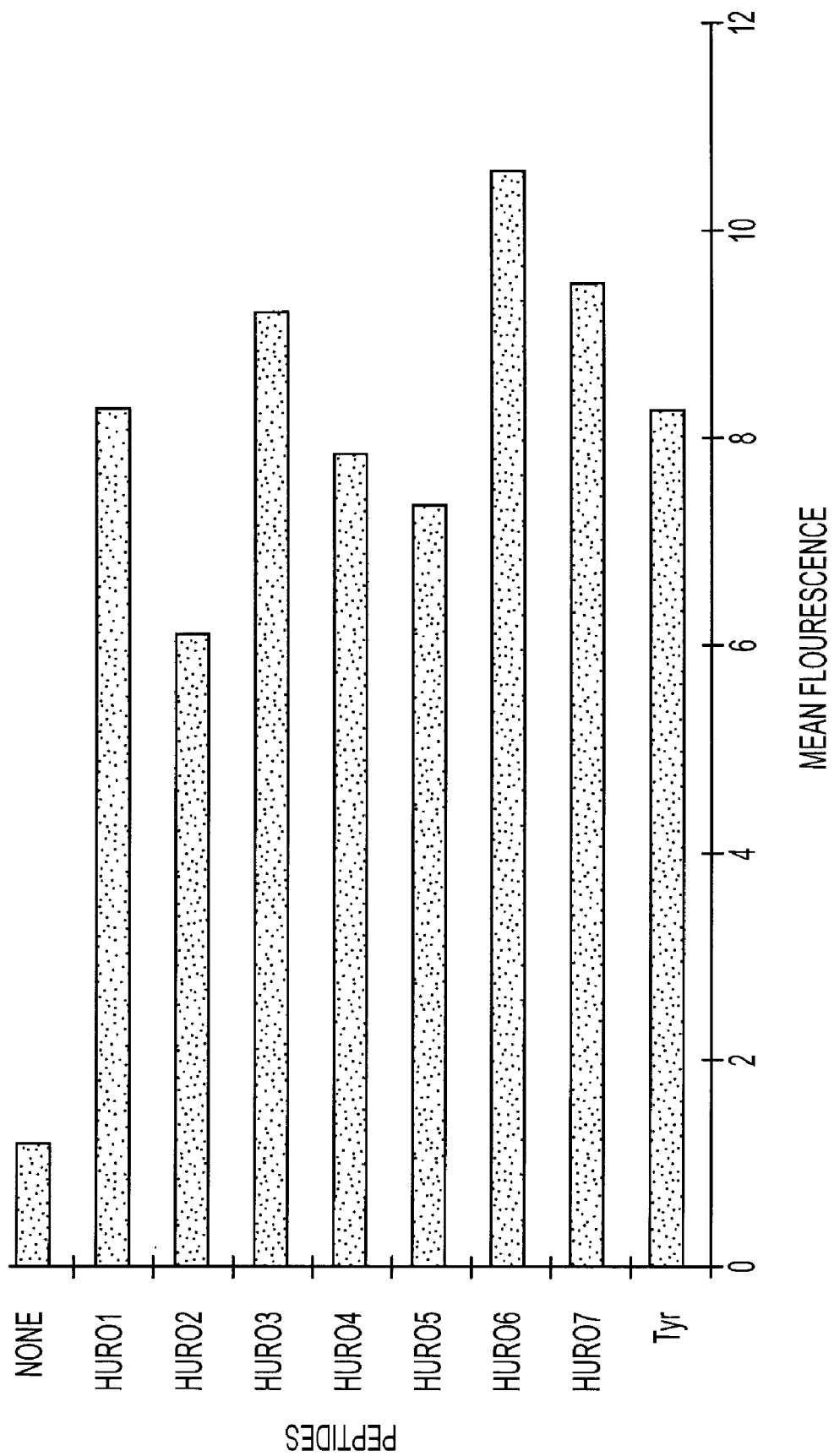
FIG. 1 demonstrates stabilization of cell surface HhD on RMA-S cells by human Uroplakin II derived peptides. Uroplakin II derived synthetic peptides (HURO1-7) or a peptide from the melanoma associated TAA Tyrosinase (Tyr) which served as a control were loaded at various concentrations (3-300 µM) on the RMA-HhD cells as described. Indirect fluorescence activated cell sorter (FACS) analyses were performed by incubating $5 \times 10^5$ loaded cells with the anti-HLA-A2 monoclonal antibodies BB7.2 for 30 minutes at 4° C. After washing the cells in PBS-0.5%, BSA-0.1°/, sodium azide, the second antibody, goat anti mouse-FITC was applied for 30 minutes at 4° C. Following another wash the fluorescence was recorded on a FACS scan (BD). Mean fluorescence at 300 µM is shown.

The present invention concerns peptides and pharmaceutical and vaccine compositions including same which can be used to prevent or cure cancer, both primary tumors and metastases. Specifically, the present invention can be used to provide vaccines which include novel and potent tumor associated antigen peptides derived from Uroplakins, Prostate specific antigen, Prostate acid phosphatase, Prostate specific membrane antigen, Lactadherin Mucin and Teratocarcinoma-derived growth factor, which can be used as anti-tumor vaccines to prevent or cure, for example, bladder, prostate or breast cancers, carcinomas in particular, or any other tumor expressing the above listed proteins.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

A specific CTL response was found in patients with bladder transitional cell carcinoma (TCC) against the tumor extract and against peptides homologous to Uroplakin II sequence, which was significantly augmented after BCG intravesical therapy. All Uroplakin II peptides employed were good immunizers in HhD mice and CTL from these mice induced intense lysis of targets loaded with Uroplakin II homologue peptides, TCC peptide extract and of the J82 HLA-A2 expressing cell line. CTL from HhD mice immunized with TCC peptide extract showed cross reactivity and induced significant lysis of targets loaded with Uroplakin II, or Uroplakin Ia homologue peptides, with TCC peptide extract and of J82 cells. For all immunized HhD mice, there was reduced lysis of targets loaded with normal bladder mucosa peptide extract and of TCC SUP cells (minimal HLA-A2 expression). Also there was no non-specific lysis. In addition, a cross reactivity of CTL induced by human Uroplakin II peptides against murine homologue peptides was found. Despite this finding there was no damage, or inflammatory infiltrate in the internal organs, including the urinary bladder on careful histological examination. These data indicate that Uroplakin homologue peptides constitute specific CTL epitopes and may be considered for immunotherapeutic vaccines alone, or in combination with intravesical BCG instillations in patients prone to recurrence and progression of bladder TCC. Similar results were obtained with human Uroplakin Ib and III.

By using HhD mice, HLA-A2 transgenic and which do not express murine MHC class I, it was found that 3 Prostate specific antigen (PSA), 4 Prostate specific membrane antigen (PSMA) and 4 Prostate acid phosphatase (PAP) homologue peptides were immunogenic. The 3 PSA homologue peptides and 2 of the 4 PSMA homologue peptides were not evaluated previously. The 2 PSMA homologue peptides, which were evaluated previously and were found to be CTL epitopes in CAP patients, were also found to be immunogenic in HhD mice. PAP homologue peptides were not evaluated previously and all 4 HLA-A2 binding peptides were very immunogenic in HhD mice and induced also, specific lysis of DU145-HhD cells. Moreover, CTL derived from HhD mice immunized with CAP peptide extract, or with DU145-HhD cells induced specific lysis of targets loaded with CAP peptide extract and PAP homologue peptides. There was also cross reactivity between CTL derived from CAP immunized HhD mice and PSA, or PSMA homologue peptide loaded targets. Low cross reactivity was found for CTL derived from DU145-HhD immunized HhD mice, probably due to low expression of these proteins by DU145 cells. There was no damage, or inflammatory infiltrate in the internal organs of immunized or control HhD mice on careful histological examination. These data indicate that PSA, PSMA and especially PAP homologue peptides constitute specific CTL epitopes and may be considered for immunotherapy of CAP patients.

It was further found a specific CTL response in HhD mice against breast tumor extract and against novel peptides complementary to Lactadherin (BA-46) sequences. These data indicate that BA-46 peptides constitute specific CTL epitopes enriched in breast carcinoma and may be considered for immunotherapeutic vaccines.

It was yet further found that Mucin (MUC-1) derived peptides are potential TAA peptides that can be used in anti-tumor vaccine preparations. CTL induced by these peptides lyse better tumor extract loaded targets than normal tissue extract loaded targets. The lysis is HLA-A2 restricted and breast specific. Three novel peptides, from non-tandem repeat array (TRA) domains were shown to constitute potential CTL epitopes.

Thus, in accordance with one aspect of the teachings of the present invention there is provided a vaccine composition which includes at least one tumor associated antigen peptide derived from a protein selected from the group consisting of Uroplakin (UP), Prostate specific antigen (PSA), Prostate specific membrane antigen (PSMA), Prostate acid phosphatase (PAP), Lactadherin (BA-46) and Mucin (MUC1).

A specific CTL response has been obtained from Teratocarcinoma-derived growth factor (CRIPTO-1) derived peptide in HhD transgenic mice. This data indicates CRIPTO-1 peptides may constitute effective CTL epitopes in humans with HLA-A2 haplotypes and may be considered for immunotherapeutic cancer vaccines.

According to another aspect of the present invention there is provided a method of vaccination for prevention or cure of cancer. The method is effected by administering to a patient a vaccine composition including at least one tumor associated antigen peptide derived from a protein selected from the group consisting of Uroplakin (UP), Prostate specific antigen (PSA), Prostate specific membrane antigen (PSMA), Prostate acid phosphatase (PAP), Lactadherin (BA-46) and Mucin (MUC1).

Immunotherapy by in vivo DNA transfer of DNA coding for TAA is based on the rationale of quality or quantity increased peptide presentation leading to activation of an immune response against these peptides. Gene or DNA vaccination results in the intracellular processing and presentation of immunogenic peptides (99). Initial reports on DNA vaccination showed that "naked" DNA injected into the muscle tissue of a mouse is expressed efficiently (32). Embryonically expressed TAA such as CEA was tested (33). Immunization of mice with CEA expressing plasmid DNA was indeed found to protect 100% of these mice against a challenge with CEA-expressing colon carcinoma cells (34). Both cellular and humoral responses have been reported after DNA vaccination in mice. In other studies a MUC-1 tandem repeat array was used for DNA vaccination of mice and 30% of these mice were protected from a tumor challenge with MUC-1 transfected murine tumor cells (35). DNA vaccination may also be used to elicit immune responses against predefined peptide epitopes, several groups now exploit the string-bead approach to link multiple different CTL or helper epitopes together on the DNA level (36). In some cases the string-bead of peptide coding DNA is built into a vaccinia virus as a delivery vehicle. Recently, it was shown that such a vaccinia virus recombinant poly-epitope vaccine was able to protect mice against several virus infections and a tumor challenge (37). The authors show that all 10 minimal peptide epitopes encoded by the string-bead are expressed and recognized by the appropriate T cell clones (38). RNA was also shown to confer anti-tumor immunity. Vaccination with RNA to ovalbumin induced CTL in mice (39). In conclusion, multiple studies have shown the efficacy of DNA vaccines in anti-viral and anti-tumor immunity.

Thus, according to yet another aspect of the present invention there is provided a DNA vaccine composition which includes at least one polynucleotide encoding a tumor associated antigen peptide derived from a sequence encoding a protein selected from the group consisting of Uroplakin (UP), Prostate specific antigen (PSA), Prostate specific membrane antigen (PSMA), Prostate acid phosphatase (PAP), Lactadherin (BA-46), Mucin (MUC1) and Teratocarcinoma-derived growth factor (CRIPTO-1). As further detailed herein, the at least one polynucleotide can be a part of a longer polynucleotide designed to encode a fused protein product from which the tumor associated antigen peptide is cleavable by a protease.

The polynucleotide is preferably DNA in a form of, or contained in, for example, naked DNA, plasmid, retroviral vector, adenoviral vector, vaccinia viral vector, herpes viral vector, lenti virus vector, EBV vector, CMV vector, polio virus vector, sindbis viral vector, semliki forest virus vector, parvo virus vector, adeno-associated virus vector, virus like particle (VLP) vector. Alternatively, the polynucleotide can be in the form of RNA. The polynucleotide can also be delivered in a non-viral delivery system, such as, for example, but not limited to, in liposomes, in complex with cationic reagents, or with a polycation, such as poly-lysine. The polynucleotide can also be delivered by mechanical means, such as, but not limited to, a gene-gun, by electrical means, or in bacterial vectors like BCG.

There is increasing evidence that peptide vaccination may be much more effective when the peptides are introduced together with an antigen presenting cell (APC) (40). In previous studies of a murine lung carcinoma we have shown that vaccination with a defined TAA peptide (MUT-1) loaded on APC result in long term survival of mice bearing lung metastases (41, 42). The most common cells used to load antigens are bone marrow and peripheral blood derived dendritic cells (DC), as these cells express costimulatory molecules that help activation of CTL. Preliminary clinical trials have been performed. In one trial HLA-A1 melanoma patients have been treated with autologous DC loaded with a MAGE-1 peptide. CTL activity was increased in tumor infiltrated lymphocytes (43). In another study, five patients with advanced pancreatic carcinoma were treated with a K-ras derived peptide loaded on DC. As a mutation of K-ras at codon 12 is frequently found in pancreatic carcinoma, three differently mutated peptides, 12-Asp, 12-Arg and 12-Val (non mutated sequence is 12-Gly) were used for vaccination, matched to the mutation in the patient's tumor. Two of the patients showed a specific CTL response and prolonged survival (44). A phase I clinical trial in 51 prostate cancer patients compared a soluble peptide to a DC based peptide in HLA-A2 patients. The peptide was derived from PSMA (SEQ ID NO:29). Only 7 patients that received DC based vaccines with this peptide responded by decreased levels of serum PSA (45). In animal studies a number of groups showed that macrophages loaded with peptides constitute efficient vaccines, yet the number of cells used for vaccination is 10 fold higher than equivalent DC vaccines. Recently in a murine lung carcinoma model the efficacy was tested of syngeneic fibroblasts treated with a proteasome inhibitor to decrease levels of endogenous peptides and loaded with synthetic MUT peptides as vaccines. Effective protection was found against metastatic spread of lung carcinoma.

Thus, according to still another aspect of the present invention there is provided a cellular vaccine composition which includes an antigen presenting cell presenting at least one tumor associated antigen peptide derived from a protein selected from the group consisting of Uroplakin (UP), Prostate specific antigen (PSA), Prostate specific membrane antigen (PSMA), Prostate acid phosphatase (PAP), Lactadherin (BA-46), Mucin (MUC1) and Teratocarcinoma-derived growth factor (CRIPTO-1). As further detailed herein, the antigen presenting cell can, for example, be a dendritic cell, a macrophage, a B cell and a fibroblast. Presenting the at least one tumor associated antigen peptide can be effected by a method selected from the group consisting of (a) transducing the antigen presenting cell with at least one polynucleotide (e.g., DNA) encoding the at least one tumor associated antigen peptide; (b) loading the antigen presenting cell with at least one polynucleotide (e.g., RNA) encoding the at least one tumor associated antigen peptide; (e) loading the antigen presenting cell with the at least one tumor associated antigen peptide (e.g., synthetic); and (d) loading the antigen presenting cell with at least one longer polypeptide (e.g., purified) including the at least one tumor associated antigen peptide. Loading can be external or internal. The polynucleotide, peptide or longer polypeptide can be fused to internalizing sequences, antennapedia sequences or toxoid sequences or to helper sequences, such as, but not limited to, heat shock protein sequences.

While it is clear that CD8+ class-I restricted CTL recognize and destroy tumor cells in vitro and in vivo, animal models often show a requirement of CD4+ MHC-class-II restricted T cell help for optimal responses (83). Helper T cell epitopes can contribute to induction of cellular immune responses by class I peptide vaccines, as seen by the synergistic tumor protection upon simultaneous vaccination with T helper and CTL epitopes (84). The 'help' to CTL is most often provided via the production of specific cytokines. Helper epitopes can be specific and derived from a tumor antigen (85). They can also broadly crossreact with a number of MHC class II molecules, and may be either pathogen-derived or comprised of sequences not found in nature (86-88). More specifically, a sequence containing a T helper epitope can be linked to a CTL epitope to create one immunogenic entity. Alternatively, a mixture of 2 or move separate entities, corresponding to CTL and T helper epitopes can be administered to elicit the desired CTL response. T helper epitopes can also be conjugated to other molecules or compounds which increase their biological activity.

As used herein in the specification and in the claims section below the phrase "tumor associated antigen" also refers to tumor specific antigen.

As used herein in the specification and in the claims section below the term "peptide" refers to native peptides (either degradation products or synthetically synthesized peptides) and further to peptidomimetics, such as peptoids and semi-peptoids which are peptide analogs, which may have, for example, modifications rendering the peptides more stable while in a body, or more immunogenic. Such modifications include, but are not limited to, cyclization, N terminus modification, C terminus modification, peptide bond modification, including, but not limited to, CH$_2$—NH, CH$_2$—S, CH$_2$—S=O, O=C—NH, CH$_2$—O, CH$_2$—CH$_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein. Further detail in this respect is provided herein.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids useful in MHC-1 recognizable peptide antigens are given herein.

Peptides can be of 8, 9 or 10 amino acids and peptides of 9 or 10 amino acid residues may be desirable, preferably 9. Thus, assume the following positions (P1-P9) in a 9-mer peptide:

P1-P2-P3-P4-P5-P6-P7-P8-P9

The P2 and P9 positions include the anchor residues which are the main residues participating in binding to MHC class 1 molecules, more specifically HLA-A2. Amino acid resides engaging positions P2 and P9 are hydrophobic or hydrophilic natural amino acids or non-natural amino acids. Examples of natural amino acids being Ala, Cys, Gln, Glu, Ile, Leu, Met, Ser, Thr and Val. These residues may preferably be neutral, hydrophobic, aliphatic and more preferably Val, Leu and Ile. Examples of non-natural amino acids being norleucine (Nle), norvaline (Nva), aminobutyric acid preferably α-aminobutyric acid. These residues may preferably be non charged and more preferably aliphatic. P9 can also be an aliphatic amino acid of the general formula —HN(CH$_2$)$_n$COOH, wherein n=2-5, as well as by branched derivatives thereof, such as, but not limited to,

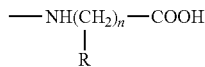

wherein R is, for example, methyl, ethyl or propyl, located at any one or more of the n carbons.

Positions P1 and P3 are also known to include amino acid residues which participate or assist in binding to MHC molecules, however, these positions can include any amino acids, natural or non-natural.

The amino terminal residue (position P1) can also be positively charged aliphatic carboxylic acids, such as, but not limited to, H$_2$N(CH$_2$)$_n$COOH, wherein n=2-5 and H$_2$N—C(=NH)—NH(CH$_2$)$_n$COOH, wherein n=2-4, hydroxy Lysine, N$^\epsilon$-methyl Lysine, N$^\epsilon$-ethyl Lysine, N$^\epsilon$-propyl Lysine or ornithine (Orn). Additionally, the amino terminal residue can be aromatic residues, such as, but not limited to, phenyl glycine, p-aminophenyl alanine, p-guanidinophenyl alanine or pyridinoalanine (Pal). These latter residues may form hydrogen bonding with the OH$^-$ moieties of the Tyrosine residues at the MHC-1 N-terminal binding pocket, as well as to create, at the same time aromatic-aromatic interactions The other positions P4-P8 are engaged by amino acid residues which typically do not participate in binding to MHC molecules, rather these amino acids are presented to the immune cells. Further details relating to the binding of peptides to MHC molecules can be found in reference 82, see Table V thereof, in particular.

Amino acid residues engaging position P4-P8 can include any amino acids natural or non natural. These residues may optionally be phosphorylated and/or glycosylated. Indeed residues which have been phosphorylated or glycosylated have been shown in some cases to enhance the binding to the T cell receptor.

Cyclization can engage position P4-P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)$_n$—COOH)—C(R)H—COOH or H—N((CH$_2$)$_n$—NH$_2$)—C(R)H—COOH, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—CH$_2$—)$_n$—S—CH$_2$—C(=O)—, wherein n=1 or 2, which is possible, for example, through incorporation of Cys or homoCys and reaction of its free SH group with, e.g., bromoacetylated Lys, Orn, Dab or Dap.

In longer peptides such as in a 10 mer peptide in which the second anchor amino acid is at position P10 the amino acid engaging P9 may include most L amino acids. In some cases shorter peptides such as an 8 mer peptide are also applicable, in which the carboxy terminal acid P8 may serve as the second anchor residue. All the options described for the anchor amino acid residues engaging positions P2 and P9 in a 9 mer peptide may apply likewise to the anchor amino acid residues engaging positions P2 and P10 in a 10 mer peptide and P2 and P8 in an 8 mer peptide.

The amino acids may be modified as is necessary to provide certain characteristics such as greater immunogenicity, more stability or improved pharmacological properties. The peptides can be for instance subject to changes such as the replacement of one or more amino acid residues whether dissimilar or similar.

Modification of the peptides may also be by decreasing, e.g. in a 10 mer peptide, or extending, e.g. in an 8 mer peptide, the amino acid sequence, for example, by deletion or addition of amino acids. It will be appreciated that preferably anchor amino acids should not be deleted.

Peptide bonds (—CO—NH—) within the peptide may be replaced by N-alkylated bonds such as N-methylated (—N(CH$_3$)—CO—), ester bonds (—C(R)H—C—O—O—CH(R)—N—), ketomethylen bonds (—CO—CH$_2$—), α-aza bonds (—NH—N(R)—CO—), wherein R is hydrogen or any alkyl, e.g., methyl carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), and peptide derivatives (—N(R)—CH$_2$—CO—), naturally presented on the carbon atom.

These modifications can occur at any of the bonds along the peptide chain and even at several (2-3) at the same time. Preferably, but not in all cases necessary, these modifications should exclude anchor amino acids.

For amino acid residues engaging positions other than the second residue from the amino terminal and the end residue at the carboxy terminal natural aromatic amino acids, Trp, Tyr and Phe, may be replaced by synthetic non-natural acid such as TIC, naphthylalanine (NaI), ring-methylated derivatives of Phe, halogenated derivatives of Phe or o-methyl-Tyr.

As used herein in the specification and in the claims section below, the term "transduced" refers to the result of a process of inserting nucleic acids into cells. The insertion may, for example, be effected by transformation, viral infection, injection, transfection, gene bombardment, electroporation or any other means effective in introducing nucleic acids into cells. Following transduction the nucleic acid is either integrated in all or part, to the cell's genome (DNA), or remains external to the cell's genome, thereby providing stably transduced or transiently transduced cells.

As used herein in the specification and in the claims section below the phrase "derived from a protein" refers to peptides derived from the specified protein or proteins and further to homologous peptides derived from equivalent regions of proteins homologous to the specified proteins of the same or other species, provided that these peptides are effective as anti-tumor vaccines. The term further relates to permissible amino acid alterations and peptidomimetics designed based on the amino acid sequence of the specified proteins or their homologous proteins.

As used herein in the specification and in the claims section below the phrase "anti-tumor vaccines" refers to vaccines effective in preventing the development of, or curing, cancer, including primary tumor and/or metastases.

As used herein in the specification and in the claims section below the phrase "prevention or cure" also refers to inhibiting, slowing or reversing the progression of a disease, substantially ameliorating clinical symptoms of a disease or substantially preventing the appearance of clinical symptoms of a disease.

In the specification and in the claims section below the phrase as used herein 'loading' refers to exposing, adding or introducing a substance into or onto a cell or vesicle or part thereof.

According to a preferred embodiment of the present invention the Uroplakin (UP), Prostate specific antigen (PSA), Prostate specific membrane antigen (PSMA), Prostate acid phosphatase (PAP), Lactadherin (BA-46), Mucin (MUC1) and Teratocarcinoma-derived growth factor (CRIPTO-1) proteins are each independently of a mammal, e.g., a humanoid such as a human being or a rodent such as murine.

According to yet another preferred embodiment of the present invention the composition further comprising a carrier. Usually the tumor associated antigen peptide(s) are presented in context of the carrier.

The carrier can be a proteinaceous carrier to which the peptides are linked. Methods of linking short peptides to carriers are well known in the art of vaccination. The carrier can alternatively be a particulate adjuvant, an oil or emulsifier based adjuvant, a gel based type adjuvant, or an adjuvant based on specific targeting of antigen, such as, but not limited to, antibody-liposom conjugates. The carrier can also be a protein or a recombinant protein produced, for example in bacteria, yeast or in mammalian cells, including cytokines, such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon alpha, interferon beta, interferon gamma and others. The carrier can also be an antigen presenting cell, such as, but not limited to, a dendritic cell, a macrophage, a B cell or a fibroblast. The cell selected is either an autologous or non-autologous HLA matching cell. Optionally the cell can be a cultured cell, a cell treated by various reagents (e.g., by early and/or late acting cytokines), transduced by genes, and/or irradiated or radiated.

The vaccine composition according to the present invention is effective in prevention or cure of cancer and/or cancer metastases. In other words, the composition is effective for primary tumors, secondary tumors and metastases thereof in the same organ or in another organ, provided that the tumor expresses the above listed tumor associated proteins. According to a preferred embodiment of the present invention the cancer being treated or prevented via the administration of the vaccine composition is a carcinoma. i.e., a malignant tumor composed of epithelial tissue. The cancer treated or prevented according to the present invention can be, for example, breast, bladder, prostate, pancreas, ovary, thyroid, melanoma, colon, stomach and/or head and neck cancer.

According to an embodiment of the present invention, the Uroplakin protein can be Uroplakin II, Uroplakin Ia, Uroplakin III and Uroplakin 1b.

According to another embodiment of the present invention, the tumor associated antigen peptides derived from the Mucin protein are from a non-tandem repeat array of Mucin.

According to yet another embodiment of the present invention, one or more tumor associated antigen peptides derived from the Mucin protein are from a region selected from the group consisting of a signal peptide, a cytoplasmic domain and an extracellular domain of Mucin.

According to a presently preferred embodiment of the present invention the one or more tumor associated antigen peptides are selected from SEQ ID NOs: 1 to 64 and 66 to 77 and effective homologues and analogs thereof.

For therapeutic or prophylactic anti-tumor treatment, the vaccine composition according to the present invention may include thickeners, carriers, buffers, diluents, surface active agents, preservatives, and the like, all as well known in the art. The composition may also include one or more active ingredients, such as, but not limited to, anti-inflammatory agents, anti-microbial agents, anesthetics and the like.

The vaccine composition may be administered in either one or more ways. Administration may be effected topically (including ophthalmically, vaginally, rectally, intranasally), orally, by inhalation, or parenterally, for example by intravenous drip or intraperitoneal, intravesical, subcutaneous, or intramuscular injection.

Compositions for topical administration can include, but are not limited to, lotions, ointments, gels, creams, suppositories, drops, liquids, sprays and powders. Conventional pharmaceutical carriers, aqueous, powder or oily bases, thickeners and the like may be necessary or desirable.

Formulations for parenteral administration can include, but are not limited to, sterile aqueous solutions which may also contain buffers, diluents, adjuvant and other suitable additives. The adjuvant is preferably of a type allowed for use in treating human beings, such as BCG adjuvant.

Dosing is dependent on responsiveness, but will normally be one or more doses per week or month, with course of treatment lasting from several weeks to several months. Persons ordinarily skilled in the art can easily determine optimum dosages, dosing methodologies and repetition rates.

The present invention provides novel tumor associated antigen peptides effective in eliciting CTL response which can therefore be effective therapeutic agents to combat cancer.

According to another embodiment of the present invention there is provided a peptide derived from a protein selected from the group consisting of Uroplakin (UP), Prostate specific antigen (PSA), Prostate specific membrane antigen (PSMA), Prostate acid phosphatase (PAP), Lactadherin (BA-46) and Mucin (MUC1) and Teratocarcinoma-derived growth factor (CRIPTO-1), the peptide comprising 8-10 amino acid residues as selected so as to promote effective binding to a MHC class 1 type molecule such that a CTL response is elicitable Each of the various aspects of the present invention as delineated hereinabove and as claimed in the claims section below finds experimental support in the Examples section that follows.

EXAMPLES

Reference is now made to the following examples, which together with the above descriptions, illustrate the invention in a non limiting fashion.

Materials and Experimental Methods

Mice: The derivation of HLA-A2.1/$D^b$-$\beta_2$m monochain, transgenies, H-$2D^b$×$\beta_2$m double knockout mice (HhD mice) was descried before (30).

Tumor and cell lines: RMA-S is a TAP-2 deficient lymphoma clone of C57BL/6 origin. The RMA-S HhD and RMA-S-HhD-B7.1 are transfectants carrying the HhD construct without or with the gene for murine B7-1 costimulatory molecule, respectively. T2 is a TAP-2 deficient human lymphoblastoid line expressing HLA-A2. RMA-S, RMA-S derivatives and T2 cells were maintained in RPMI 1640-10% FCS and antibiotics.

The human tumor cell lines, J82 (TCC of the bladder) sup (TCC of the bladder, DU145 (prostate carcinoma) and MDA-MB-157 (breast carcinoma) and the HhD transfectants of DU145 and MDA-MB-157 were maintained in DMEM-10% FCS 2 mM glutamine-1 mM sodium pyruvate-1% non-essential amino acids and antibiotics.

HhD and B7-1 transfectants were grown in presence of 500-1000 µg/ml of Geniticin, G418. All tissue culture media and supplements were purchased from Gibco.

Peptide synthesis: Peptides were synthesized on an ABIMED AMS 422 multiple peptide synthesizer (Langenfeld, Germany), employing the a-N-9-fluorenylmethoxy-cartonyl (Fmoc) strategy following the company's commercially available protocols. Peptide chain assembly was conducted on a 2-chlorotrityl chloride resin (Novabiochem, Laufelfingen, Switzerland). Crude peptides were purified to homogeneity by reversed-phase HPLC on a semi-preparative silica C-8 column (250×10 mm; Lichnonorb RP-8; Merck). Elution was accomplished by a linear gradient established between 0.1% trifluoroacetic acid in water and 0.1% trifluoroacetic acid in 70% acetonitrile in water (v/v). Purity of peptides (≅96%) was ascertained by analytical HPLC (RP-18) using various acetonitrile water (containing 0.1% trifluoroacetic acid) gradients. The products' compositions were determined by amino acid analysis (Dionex automatic amino acid analyzer, Sunnyvale, Calif.) after extraction acid hydrolysis. Molecular weight was ascertained by mass spectrometry (VG Tofspec; Laser Desorption Mass. Spectrometry; Fison Instruments, Manchester, U.K.). Tables 1-8 present these peptides.

Preparation of peptide fractions from fresh human tumors and normal tissues: Surgical specimens of TCC, normal bladder mucosa, prostate carcinoma, hyperplastic benign prostate, breast carcinoma or normal breast tissue were transferred on ice from surgery to a qualified pathologist. Tumor tissue were cleaned from most adjacent tissue and snap frozen. Non-necrotic fragments, from 5-10 patients were homogenized in PBS; 0.5% Nonidet P-40; 10 µg/ml soybean trypsin inhibitor; 5 µg/ml lupeptide; 8 µg/ml aprotinin and 0.5 mM PMSF and homogenized using a glass-teflon homogenizer. Following further stirring for 30 minutes at 4° C., the homogenates were titrated with 10% TFA to a final concentration of 0.1% TFA and stirred for 30 minutes at 4° C. After ultra-centrifugation for 30 minutes at 42K rpm the supernatants were applied to Sephadex G25 columns and fractions were monitors at 230 nm. Peptide fractions under 10 Kd were pooled, lyophilized and further fractionated by centriprep 3 by centrifugation (Amicon, Beverly, Mass.). The peptide pool after lyophilization, was dissolved in opti-MEM (Gibco) for further use.

Scoring of HLA-A2.1 binding peptides: Protein sequences were screened for MHC binding by a HLA Peptide Binding Predictions software approachable through a worldwide web interface at (see also reference 82). This software, based on accumulated data, scores every possible peptide in the protein for possible binding to MHC according to the contribution of every amino acid in the peptide. Theoretical binding scores represent calculated half-life of the HLA-A2.1-peptide complex.

Measurement of peptide binding by stabilization of cell surface MHC: Peptide binding to HhD was measured by stabilization of HhD on RMA-S transfectants, using an indirect FACS assay as follows: $5 \times 10^5$ peptide loaded TAP-2 deficient RMA-S-HhD cells (see vaccination), were incubated with anti HLA monoclonal antibodies for 30 minutes at 4° C. After washing the cells with PBS–0.5%, BSA+0.1%, sodium azide, the second antibody, goat anti mouse-FITC (Jackson Lab.), was applied for 30 minutes at 4° C. Following washing, the amount of bound antibodies was detected by FACSscan (Bacson).

Mouse monoclonal antibodies B-9-12, w6/32 (anti HLA A, B, C) and B.B7.2 (anti HLA-A2.1) were used for analyses.

Vaccination: Mice were immunized intraperitonealy three times at 7-day intervals, with $2 \times 10^6$ irradiated (5,000 rad) tumor cells, or with peptide-loaded RMA-S-HhD-B7.1 transfectants. Peptide loading of RMA-S-HhD-B7.1 cells was performed as follows: After washing the cells 3 times in PBS, the surface expression of HhD monochins was stabilized by a 4 hours culture at 26° C. Synthetic peptides, or peptide extracts were added to $10 \times 10^6$ cells in 1 ml of opti-MEM (Gibco) medium to a concentration of 100 µM or 1 mM, respectively. The cells were incubated at 26° C. and for additional 3 hours at 37° C. Peptide loaded RMA-S-HhDσ-σB7.1 cells were irradiated (5000 rad), washed, resuspended in PBS and injected into mice. In mixed synthetic vaccines, RMA-S-HhD-B7.1 cells were loaded separately with each peptide and pooled before vaccination.

In vitro cytotoxicity assays: Mice were immunized intraperitonealy three times at 7-day intervals, with $2 \times 10^6$ irradiated (5,000 rad) tumor cells, or with peptide-loaded RMA-S-HhD-B7.1 transfectants. Spleens were removed on day 10 after the last immunization and splenocytes were restimulated in vitro with either irradiated tumor cells (for mice immunized with tumor cells) or with lymphocytes pulsed with 100 µM synthetic peptides or 1 mM patients-derived extract in opti-MEM (Gibco) medium Restimulated lymphocytes were maintained in RPMI 1640 medium containing 10% FCS, 1 mM glutamine, combined antibiotics, 1 mM sodium pyruvate, 10 mM HEPES, pH 7.4, $5 \times 10^{-5}$ M β-mercaptoethanol, and 1% nonessential amino acids (RPMI-HEPES medium) for 5 days. Viable lymphocytes (effector cells), were separated by lymphocyte-M (Cedarlane, Ontario, Canada) centrifugation, resuspended in RPMI-HEPES medium, and admixed at different ratios with $5 \times 10^3$ peptide loaded RMA-S-HhD cells, previously loaded with different peptides (see vaccination). CTL assays were performed in U-shaped microtiter wells, at 37° C., 5% $CO_2$ for 5 hours. Cultures were terminated by centrifugation at 1,000 rpm for 10 minutes at 4° C. A total of 100 µl of the supernatants was mixed with scintillation fluids and counted in a beta counter. Percentage of specific lysis was calculated as follows: % lysis=(cpm in experimental well–cpm spontaneous release)/(cpm maximal release–cpm spontaneous release)×100. Spontaneous release was determined by incubation of 100 µl-labeled target cells with 100 µl of medium. Maximal release was determined by solubilization of target cells in 100 µl 0.1 M NaOH.

Sensitization of human PBL in vitro: Patients were HLA typed by the Tissue Typing Unit of The Rabin Medical Center, Israel. Only HLA-A2.1 carrying haplotypes were used herein. Heparanized blood, 40 ml/patient was separated on Ficoll gradients, mononuclear cells were collected at the interphase, washed three times in PBS and resuspended in PBS. A third of the lymphocyte volume was incubated with tumor extracted peptides, at a concentration of 1 $O.D_{230}$/ml for 2 hours at 37° C. The other two thirds of the cells were suspended at $10^6$ cells/ml in RPMI-10% FCS, 2 mM glutamine, 1 mM sodium pyruvate, 10 mM Hepes, $5 \times 10^{-3}$ M β-mercaptoethanol and combined antibiotics. Peptide loaded cells were added together with 5-20 U/ml of recombinant human IL-2 (Peprotec, Rehovot, Israel). Cells were incubated for 5-7 days at 37° C., 5% $CO_2$ and then used in CTL assays as described above.

Experimental Results

Example 1

Uroplakins are T Cell Defined TAAs in Transitional Cell Carcinoma (TCC)

Transitional cell carcinoma (TCC) of the bladder represents a prevalent cancer. Its incidence increases gradually during life and peaks in the 7th and 8th decade to 200/100,000. About 95% of bladder tumors are TCC. Of these, 75% are superficial papillary tumors and have a 15%-20% progression rate during the first two years of follow up. Approximately, 20%-25% of TCC present as muscle invasive tumors with aggressive behavior and a 40% survival rate at 5 years (46). After surgical resection of superficial tumors, intravesical instillations of chemotherapeutics as Tiotepa or Mitomycin, or non-specific intravesical immunotherapy with Bacillus Calmette Guerein (BCG), reduce the frequency of recurrences and have a minimal effect on progression. BCG intravesical instillation was found to be the most effective in reducing the recurrence and progression rate of high grade papillary TCC and of transitional cell carcinoma in situ. The mechanism of action was not yet elucidated. However, following therapy there is a mononuclear infiltrate of the lamina propria of the bladder mucosa. This infiltrate is rich in T-cells, macrophages and Langerhans cells (47). It was found that CD8 T-cells were activated after BCG intravesical therapy and induced specific lysis of TCC cells (48). Also, BCG intravesical instillation resulted in increased presentation of MHC complexes on transitional cell membrane (49). Lately, CTL, which induced specific lysis of autologous tumor cells, were identified among tumor infiltrating lymphocytes grown from transitional cell carcinomas of the bladder (50). It seems that specific cytotoxic T-cell immunity against TCC may be augmented by BCG intravesical therapy.

An important group of TAAs are actually differentiation antigens. Such antigens were shown to induce CTL in melanoma and in colon carcinoma patients (22, 23).

Transitional epithelium is a differentiated multilayered epithelium which is restricted to the urinary tract. It is composed of 4 to 7 cell layers: a basal cell layer; an intermediate 2-3 cell layer and an apical (luminal) layer composed of umbrella like cells. These latter cells are connected by tight junctions and create an impermeable barrier to water and urinary solutes.

Lately, differentiation proteins of transitional epithelium have been characterized morphologically and biochemically. These proteins were found in urothelial plaques which are present in the luminal plasma membrane of urothelial superficial (umbrella) cells. The molecular constituents of these plaques comprise four transmembranal proteins designated Uroplakins (UP); UP Ia (27 Kd); UP Ib (28 Kd); UP II (15 Kd) and UP III (47 Kd glycoprotein; the size of the core protein is 28.9 Kd). Uroplakin III probably plays a role in the formation of the urothelial glycocalyx and may interact with the cytoskeleton. An extensive evaluation of UP tissue distribution showed that UP are restricted to normal transitional cell epithelium and to TCC (51). In normal transitional epithelium the UPs were found in the apical membrane of the superficial umbrella cells. In superficial papillary TCC, the UPs were localized in the apical membrane of the luminal cells and in the cell membranes lining intra and inter-cellular lumina. In invasive TCC, UPs were localized more randomly in the cell membrane of the cells which infiltrated the stroma. Recently, the sequence of human Uroplakin II cDNA and Uroplakin Ia genomic sequence were determined and their protein sequences were deduced (NCBI accession Nos. 2190407 and 2098577, respectively). Since TCC patients treated by BCG were shown to have increased T cell infiltrates in the bladder mucosa, we first tested whether BCG treated patients show increased CTL activity against TCC derived peptides and whether UP II peptides may constitute CTL specific epitopes. We further used the TCC model to test the T cell repertoire overlap between patient derived CTL and CTL induced in the unique H-2 $D^{b-/-} \times \beta 2m^{-/-} \times HhD^{+/+}$ (HhD) mice.

Cytotoxic activity of human peripheral blood lymphocytes (PBL) against target cells pulsed with Uroplakin II peptide homologues: The human UP II amino acid sequence was screened for potential HLA-A2 binding, 9 amino acids peptides by a HLA binding motif program. We chose that particular HLA allele because it is present in 45% of the population. Seven 9-mer peptides, which were predicted to bind with high affinity to HLA-A2 were selected and synthesized (Table 1). The binding of these peptides to HLA-A2 was tested by an MHC stabilization assay utilizing TAP negative cells, which can present exogeneously bound peptides. The RMA-S cells (30) transfected by the HhD construct were loaded with various concentrations of UP II peptides and then reacted with anti-HLA antibody. High affinity binding was shown for all 7 peptides by FACS analyses (FIG. 1).

TABLE 1

Predicted human Uroplakin II peptides that bind to HLA-A2

| Peptide | Sequence | Amino acids* | SEQ ID: |
|---------|----------|--------------|---------|
| HURO1   | FLLVLGFII | 168-176     | 1       |
| HURO2   | VLPSVAMFL | 161-169     | 2       |
| HURO3   | LVLGFIIAL | 170-178     | 3       |
| HURO4   | KVVTSSFVV | 67-77       | 4       |
| HURO5   | LVPGTKFYI | 109-117     | 5       |
| HURO6   | LLPIRTLPL | 4-12        | 6       |
| HURO7   | YLVKKGTAT | 119-127     | 7       |

The prediction program is described in Materials and Methods. The peptides are listed in descending order of predicted HLA-A2.1-peptide complex stability. Single letter amino acid codes and the position of the peptide in the protein are listed. * Numbering is according to NCBI accession No. 2190407.

Figure 2:
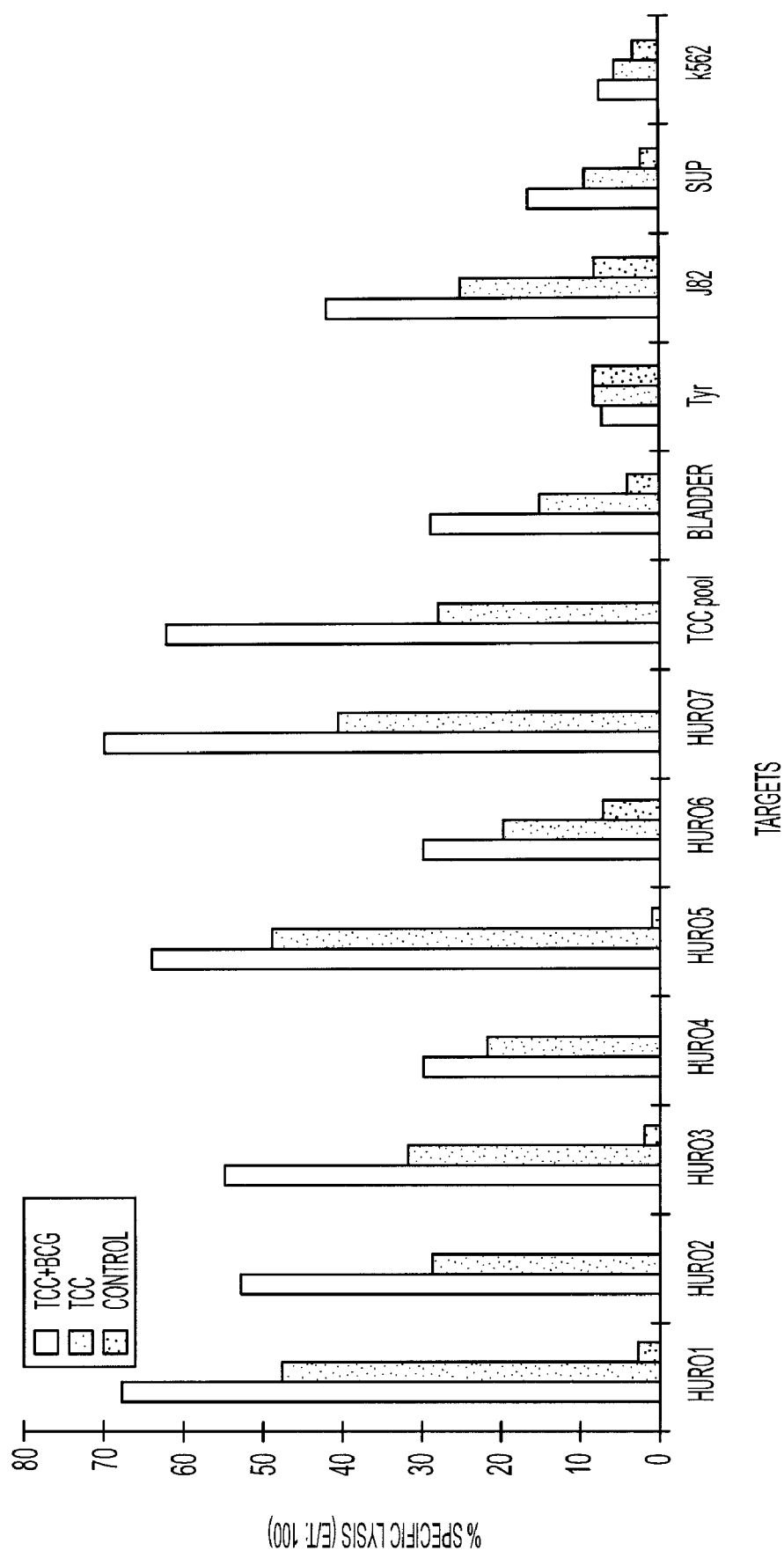
FIG. 2 demonstrates lytic activity of human peripheral blood lymphoyctes (PBL) against Uroplakin II loaded target cells. PBL from HLA-A2 positive patients were resensitized with tumor extracted peptide preparations from transitional cell carcinoma (TCC) specimens as described in Materials and Methods. Resensitized lymphocytes from 4 TCC patients treated with Bacillus Calmette Guerein (BCG), 2 non-treated TCC patients, and 1 prostate cancer patient (control), were admixed at different ratios with labeled T2 cells, loaded with TCC extracted peptides (TCC pool) normal bladder mucosa extracted peptides (bladder), synthetic Uroplakin II peptides (HURO1-7) or the melanoma peptide from Tyrosinase (Tyr). Labeled target cells, J82, a HLA-A2 expressing TCC line, SUP, a low class I expresser and K562, a NK sensitive line were also tested. Percent specific lysis, at effector: target of 100:1 is presented.
Figure 3:
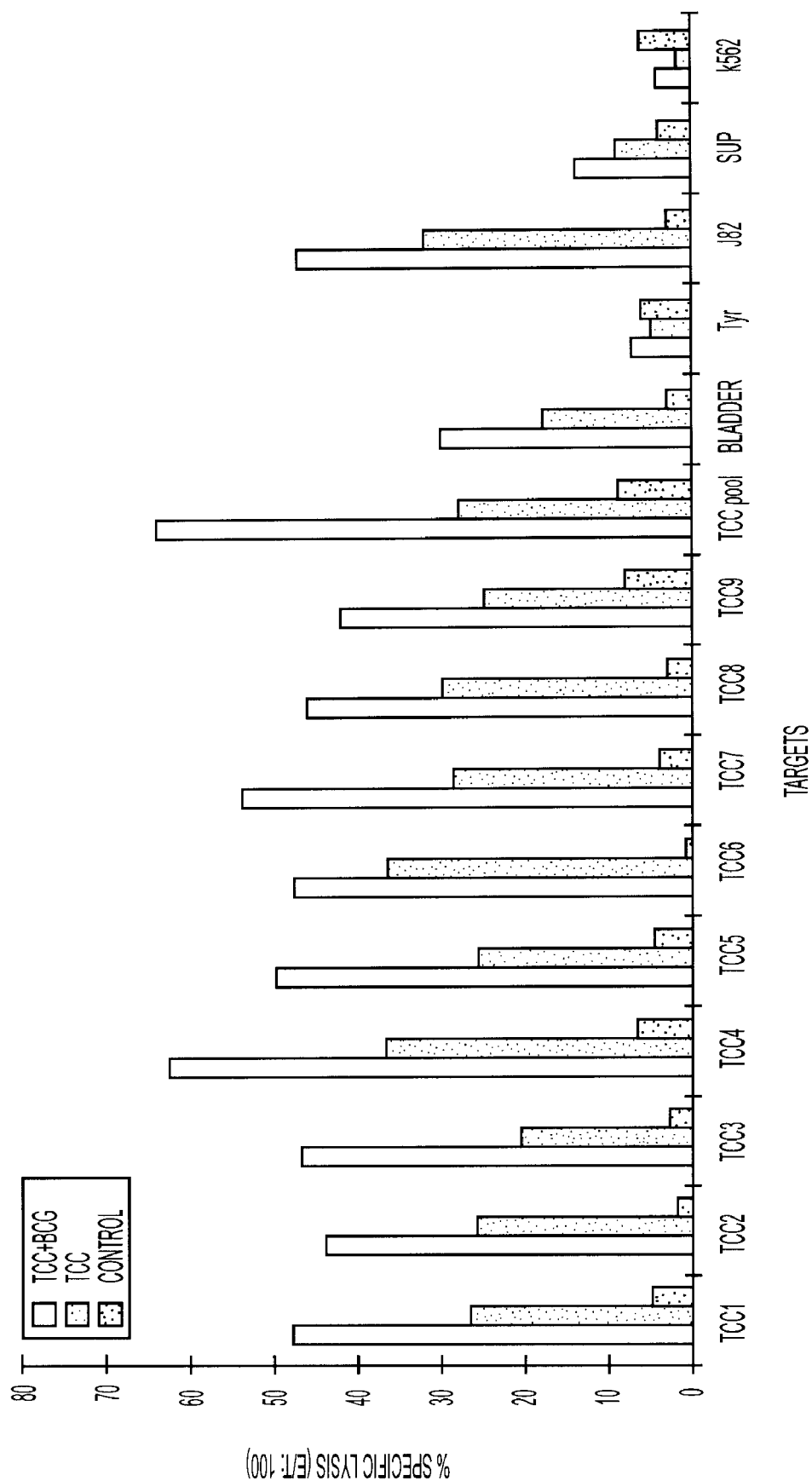
FIG. 3 demonstrates lytic activity of human peripheral blood lymphocytes against peptides extracted from individual TCC tumors. PBL were resensitized as in FIG. 2. Peptides extracted from 9 individual tumors (TCC1-9), that were pooled for resensitization, were loaded on T2 cells. Labeled loaded targets were tested for lysis by sensitized PBL as described in FIG. 2.

To restimulate CTL activity in patient's PBL we chose 6 TCC patients of the HLA-A2 haplotypes: 4 patients underwent adjuvant intravesical BCG instillations and 2 underwent no adjuvant therapy after endoscopic resection of the TCC. Another patient without TCC served as control. PBL were stimulated in vitro by a mixture of tumor acid extracted peptides from 9 TCC samples as described before (52). Each tumor was extracted individually and an equimolar ratio of each sample was added to the mixture. The final concentration of peptides in the stimulation reaction was 1 O.D. 230/ ml. Antigen presenting cells (APC) from the same peripheral blood were pulsed with the tumor extract. Peripheral blood lymphoyctes (PBL) were stimulated with APC loaded with pooled TCC extract and with IL2 for 5 days. Uroplakin II peptides, TCC extracted peptides and normal bladder extracted peptides were loaded on labeled T2 cells (HLA-A2 positive cells which are TAP deficient, express empty MHC molecules and can be loaded only with exogenous peptides), and were screened by CTL obtained from PBL of the patients, as described. CTL from TCC patients treated with BCG induced 32% to 71% specific lysis of Uroplakin II peptide loaded T2 cells (FIG. 2). Tumor extract loaded targets were lysed at 62% while normal bladder extract loaded targets were lysed at 29% only, indicating preferential recognition of tumor antigens. CTL from TCC patients without BCG adjuvant therapy induced 25% to 48% specific lysis of T2 cells loaded Uroplakin II peptides, 29% lysis of tumor extract loaded T2 cells and 15% lysis of bladder extract loaded T2 cells. There was no lysis of T2 cells loaded with breast tumor extract, or with a HLA-A2 binding peptide homologue to tyrosinase, a melanoma differentiation antigen. A TCC cell line expressing HLA-A2, J82 was effectively killed while another TCC line SUP, was not lysed. Also, there was no lysis of a natural killer (NK) sensitive cell line (K562). CTL obtained from the patient without TCC induced no specific lysis of tumor extract, or Uroplakin II peptides loaded APC cells. The differences between TCC patients treated with BCG, TCC patients without adjuvant therapy and non-TCC patients were very significant (P<0.001). We also tested the activity of patient's PBL, resensitized by the pool of tumor extracts, against individual tumor extracts. FIG. 3 shows higher activity of lymphocytes derived from BCG treated patients than lymphocytes derived from non-treated patients. Control lymphoyctes show low activity. Thus shared antigens are expressed in all TCC samples.

CTL induced in HhD mice recognize the same UP II peptides as human PBL: The immunogenicity of Uroplakin homologue peptides was also evaluated in a mouse model, in which the murine MHC class I genes are not expressed ($D^{b-/-}$, β2-microglobulin –/–, double knockout) and which is transgenic for a HLA-A2 and human β2-microglobulin monochain (HhD mice). The advantage of a HLA-A2 transgenic mouse model is that CTL epitopes can be detected more easily and reproducibly, without lengthy and repeated in vitro stimulations. The murine MHC knockout mice used herein has the additional advantage that their CTL repertoire is only HLA-A2 restricted and the CTL response against human tumor extract or human cell lines is not masked by a potential xenogeneic response. HhD mice were immunized with the 7 Uroplakin II homologue peptides or with the same TCC peptide extract used for stimulation of patient's PBL. Lymphocytes were obtained from the spleens of these mice and restimulated in vitro once with the corresponding peptides.

The 7 UP II peptides, that were recognized by human CTL, 8 new UP Ia homologues peptides with high HLA-A2 binding affinity (Table 2), 4 murine UP II derived HLA-A2 binding peptides (Table 3), TCC and normal bladder mucosa peptide extracts and two TCC cell lines: J82 (HLA-A2 positive) and TCCSUP were screened by the CTL obtained from these mice.

TABLE 2

Predicted human Uroplakin Ia peptides that bind to HLA-A2

| Peptide | Sequence | Amino acids* | SEQ ID: |
|---------|----------|--------------|---------|
| HURO11  | SLFAETIWV | 33-41       | 8       |
| HURO12  | MLIAMYFYT | 248-256     | 9       |
| HURO13  | LMWTLPVML | 241-249     | 10      |

TABLE 2-continued

Predicted human Uroplakin Ia peptides that bind to HLA-A2

| Peptide | Sequence | Amino acids* | SEQ ID: |
|---------|----------|--------------|---------|
| HURO14  | MLIVYIFEC | 100-108     | 11      |
| HURO15  | YIFECASCI | 104-112     | 12      |
| HURO16  | LVLMLIVYI | 97-105      | 13      |
| HURO17  | ALCRRRSMV | 85-93       | 14      |
| HURO18  | LLSGLSLFA | 28-36       | 15      |

The prediction program is described in Materials and Methods. The peptides are listed in descending order of predicted HLA-A2.1-peptide complex stability. Single letter amino acid codes and the position of the peptide in the protein are listed.
*Numbering is according to NCBI accession No. 2098577.

TABLE 3

Predicted murine Uroplakin II peptides that bind to HLA-A2

| Peptide | Sequence | Amino acids* | SEQ ID: |
|---------|----------|--------------|---------|
| MURO1   | FLLVVGLIV | 168-176     | 16      |
| MURO3   | LVVGLIVAL | 170-178     | 17      |
| MURO4   | KVVKSDFVV | 69-77       | 18      |
| MURO6   | TLPVQTLPL | 4-12        | 19      |

The prediction program is described in Materials and Methods. The peptides are listed in descending order of predicted HLA-A2.1-peptide complex stability. Single letter amino acid codes and the position of the peptide in the protein are listed. The murine 1, 3, 4, 6 peptides are homologous to the human Uroplakin II peptides 1, 3, 4, 6 in Table 1.
*Numbering is according to NCBI accession No. 586160.

Figure 4:
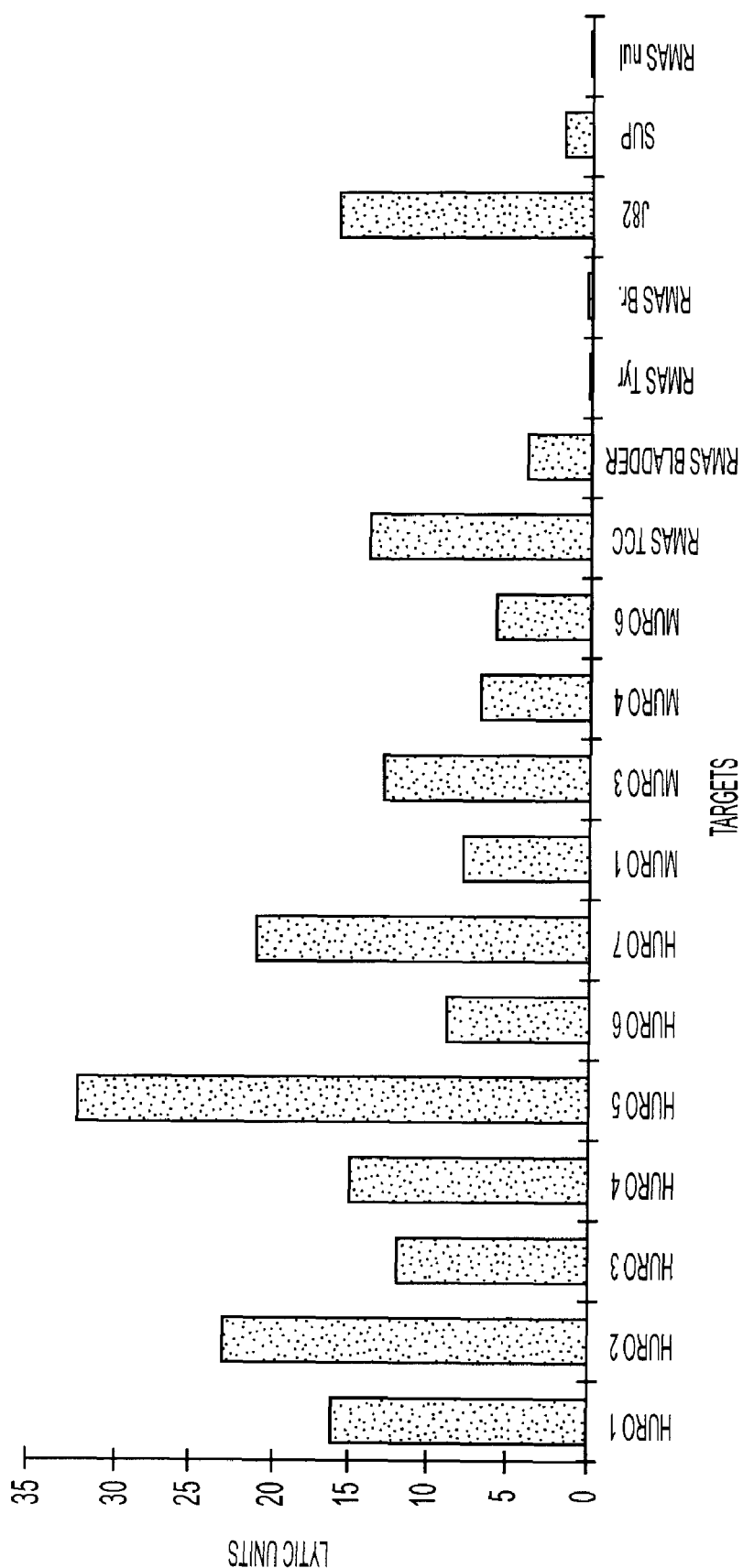
FIG. 4 demonstrates lysis of human Uroplakin II and murine Uroplakin II peptide loaded target cells by CTL induced again human Uroplakin II derived peptides in HhD mice. Mice were immunized as described, by RMA-S-HhD-B7.1 cells, loaded with human Uroplakin II derived synthetic peptides 1-7 as described in Materials and Methods. Loading was performed with individual peptides and cells were pooled for immunization. Resensitized CTL (see Materials and Methods) were tested for lysis of RMA-S-HhD targets loaded with human or murine Uroplakin II peptides (HURO 1-7, MURO1, 3, 4, 6) with TCC or normal bladder extracted peptides (RMA-S TCC, RMA-S bladder), with the tyrosinase peptide (RMA-S Tyr) with peptides derived from breast tumors (RMA-S Br.) or with the cell lines J82 or SUP. E:T ratios of 100:1, 50:1, 25:1 and 12.5:1 were tested and the results are presented in lytic units LU30 was calculated by linear regression analysis of percentage lysis vs. the log (1n) of effector cell number and expressed as the number of LU per $10^6$ effector cells. The coefficient was 0.85-0.95 for all groups.

The results are expressed as lytic units (LU30), which represent $10^6$/the number of effectors which induce 30% specific target lysis. More LU signify a more potent CTL response. FIG. 4 shows that CTL from HhD mice immunized with Uroplakin II peptides (1-7 loaded individually and injected by a mixture of loaded cells) induced a significant lysis of RMA-S-HhD cells loaded with Uroplakin II homologue peptides (8.1 to 32.2 LU). There was no lysis of RMA-S-HhD cells loaded with nonspecific peptides as breast tumor extract or the HLA-A2 binding tyrosinase homologue peptide. Also, there was no lysis of RMA-S-HhD cells without peptides (empty target cells). There was intense lysis of J82 cells (17.3 LU) and there was much less lysis of TCCSUP cells (1.2 LU). There was also intense lysis of RMA-S-HhD cells loaded with TCC peptide extract (15 LU) and less lysis of normal bladder mucosa peptide extract loaded cells (4.5 LU) (FIG. 4).

Figure 5:
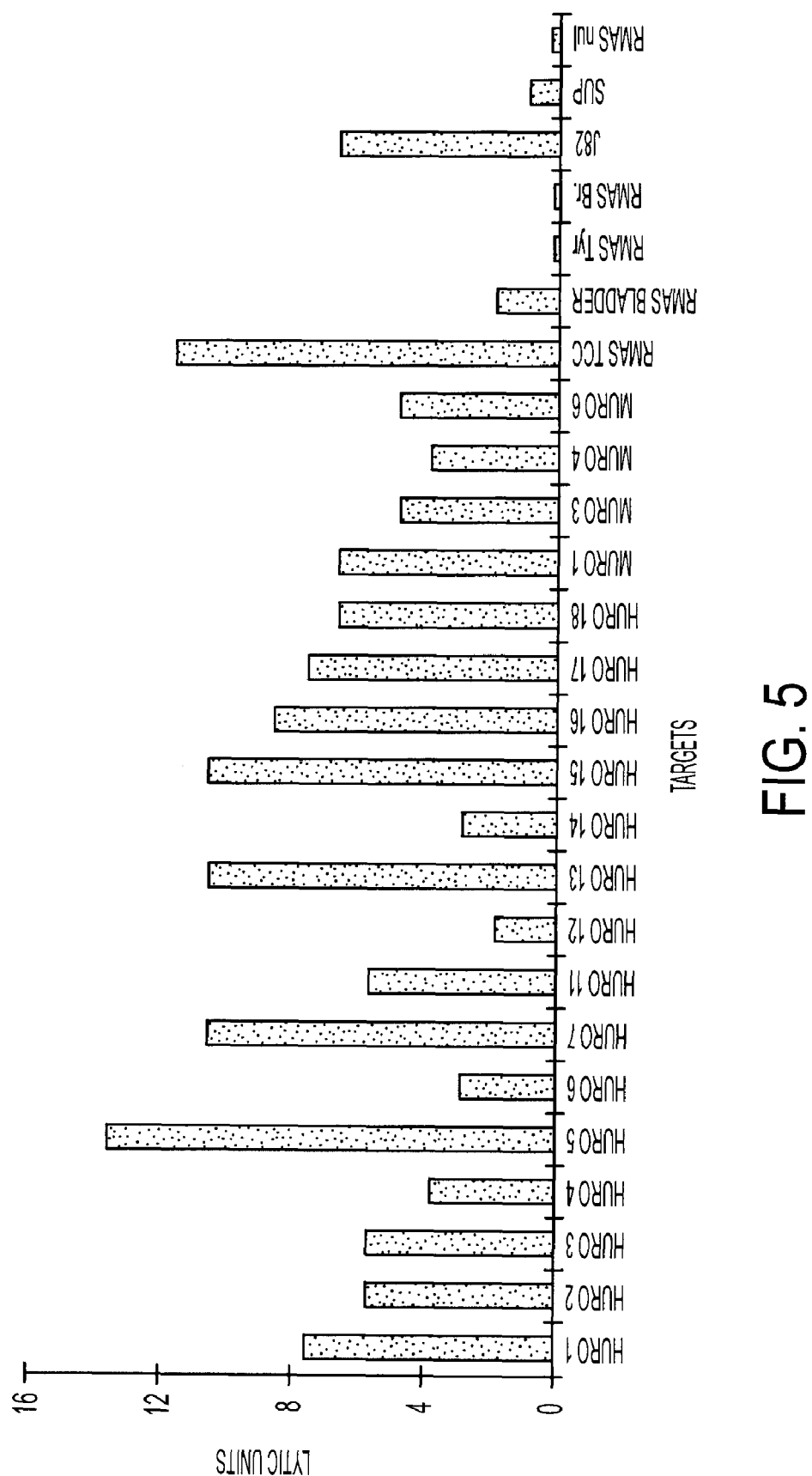
FIG. 5 demonstrates lysis of human Uroplakin II and Ia and murine Uroplakin II derived peptide loaded target cells by CTL induced against TCC extracted peptides in HhD mice. HhD mice were immunized by RMA-S-HhD-B7.1 cells loaded with peptides extracted from 9 TCC samples and pooled. CTL were prepared as described and tested for lysis of labeled RMA-S-HhD target cells loaded with synthetic, tissue derived or control peptides and cell lines as in FIG. 4 and synthetic peptides derived from Uroplakin Ia (HURO 11-18). The results are presented in lytic units as described in FIG. 4.

CTL from mice immunized with TCC peptide extract induced significant lysis of RMA-S-HhD targets loaded with Uroplakin II homologue peptides (3.2 to 14 LU); Uroplakin Ia homologue peptides (2 to 11.4 LU); TCC peptide extract (12.6 LU) and less lysis of these targets loaded with normal bladder mucosa peptide extract (2 LU). There was also intense lysis of J82 cells (7.6 LU) and less lysis of TCCSUP cells (0.8 LU). There was no lysis of target cells loaded with nonspecific peptides or of empty target cells. The lysis pattern of the targets loaded with the different Uroplakin II homologue peptides was similar to the CTL assays using human PBL, CTL from HhD mice immunized with Uroplakin II peptides or with TCC peptide extract (FIG. 5).

Although human and HhD murine CTL recognize the same UP II peptides, it was not clear whether HhD murine CTL are directed against the actual T cell epitopes or against possible differences between humanoid and rodent UP II. We evaluated also the crossreactivity of CTL from mice immunized with human Uroplakin II peptides against 4 homologue murine Uroplakin II peptides. The murine UP II sequence was screened for HLA-A2 binding peptides and 4 peptide homologues to human peptides 1, 3, 4 and 6 were synthesized. Murine peptides differ in 1-3 amino acids from similar human peptides, yet most are conservative changes (Tables 1 and 3). Murine UP II peptides bind stably to RMA-S-HhD cells.

There was significant lysis of the targets loaded with each of these murine peptides. A good correlation between the LU30 results for the human and their homologue murine peptides was found. Three human peptides induced more target lysis than their murine counterpart and for the fourth peptide the trend was opposite (FIGS. 4 and 5). Thus, the specificity of the HhD murine CTL, as the specificity of human PBL is directed to common epitopes on the peptides. To examine whether any autoimmune effects are observed in peptide vaccinated HhD mice, the internal organs of the HhD mice immunized with TCC peptide extract or with Uroplakin II homologue peptides were formalin fixed and representative sections from each organ were stained with hematoxylin and eosin. Two non-immunized HhD mice served as control. There were no pathological finding such as tissue necrosis or inflammatory infiltrate in any of the organ examined. The urinary bladder was carefully examined using a larger number of sections. The bladder wall including the mucosa was normal in the immunized and in the control mice.

The immunogenicity of additional Uroplakin-derived peptides was evaluated in the HhD mouse strain, in which the murine MHC class I genes are not expressed ($Db^{-/-}$, $\beta$2-microglobulin$^{-/-}$ double knock-out), and which is transgenic for an HLA-A2 and human $\beta$2-microglobulin monochain. Seven HLA-A2 binding peptides derived from the sequence of Uroplakin Ib, 2 from Uroplakin II, and 6 from Uroplakin III (see Table I) were tested for their ability to evoke specific CTL responses in these mice. After three weekly immunizations, splenic lymphocytes were restimulated in vitro with cognate peptide and then incubated with radiolabeled peptide-loaded target cells. FIGS. 23*a-e* show that several of the tested peptides (peptides B1, B2, B5, B6, 3.2, 3.3, and 8) could elicit lymphocytes which specifically lysed target cells. Importantly, in all assays there was no significant lysis of unloaded target cells (non) or of cells loaded with a non-specific HLA-A2 binding peptide from the melanoma antigen tyrosinase (tyr).

Table 3a below shows the sequences of the peptides tested in single letter amino acid code, their starting position in the intact protein.

TABLE 3a

Predicted human Uroplakin Ib, II and III peptides that bind to HLA-A2

| Peptide | Start Position | Sequence | SEQ ID NO: |
|---------|---------------|----------|------------|
| Uroplakin Ib/B1 | 239 | AILCWTFWV | 50 |
| Uroplakin Ib/B2 | 92  | FILMFIVYA | 51 |
| Uroplakin Ib/B3 | 29  | LTAECIFFV | 52 |

TABLE 3a-continued

Predicted human Uroplakin Ib, II and III peptides that bind to HLA-A2

| Peptide | Start Position | Sequence | SEQ ID NO: |
|---|---|---|---|
| Uroplakin Ib/B4 | 154 | MLQDNCCGV | 53 |
| Uroplakin Ib/B5 | 240 | ILCWTFWVL | 54 |
| Uroplakin Ib/B6 | 86 | KILLAYFIL | 55 |
| Uroplakin Ib/B7 | 64 | FVGICLFCL | 56 |
| Uroplakin II/8 | 161 | VLLSVAMFL | 57 |
| Uroplakin II/9 | 162 | LLSVAMFLL | 58 |
| Uroplakin III/3.1 | 214 | ILGSLPFFL | 59 |
| Uroplakin III/3.2 | 128 | ILNAYLVRV | 60 |
| Uroplakin III/3.3 | 221 | FLLVGFAGA | 61 |
| Uroplakin III/3.4 | 20 | NLQPQLASV | 62 |
| Uroplakin III/3.5 | 47 | CMFDSKEAL | 63 |
| Uroplakin III/3.6 | 62 | YLYVLVDSA | 64 |
| Tyrosinase | 368 | YMDGTMSQV | 65 |

Table 3a shows the sequences of the peptides tested in single letter amino acid code and their starting position in the intact protein (according to NCBI accession nos. 3298345 (peptides 3.1-3.6), 3483011 (peptides 8 and 9), and 3721858 (peptides B1-B7).

Example 2

Figure 6:
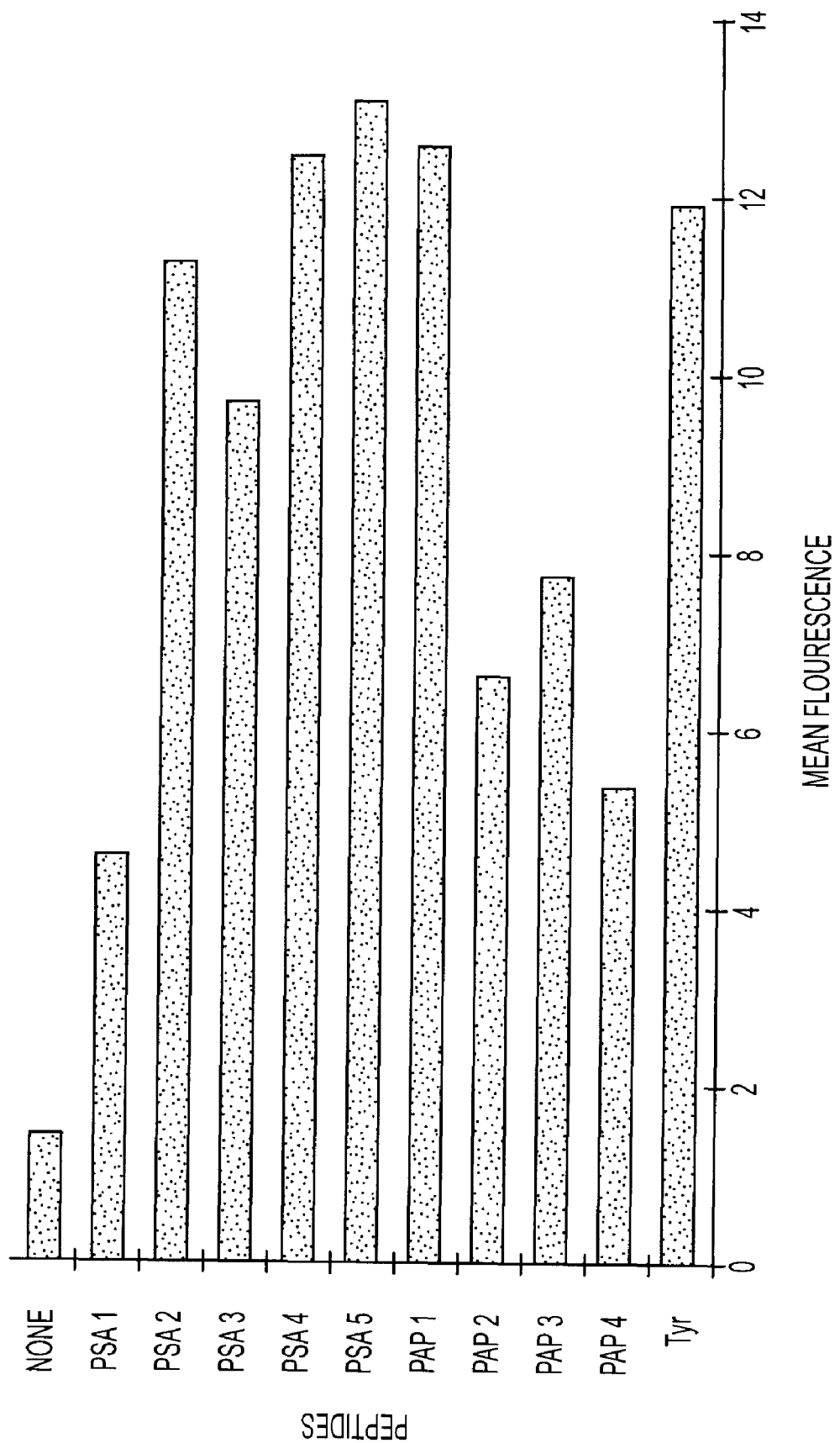
FIG. 6 demonstrates stabilization of cell surface HhD on RMA-S cells by human Prostate specific antigen (PSA) and Prostate acid phosphatase (PAP) derived peptides. PSA and PAP derived peptides were loaded at various concentrations (1 μM-1 mM) on RMA-S-HhD cells. FACS analysis was performed as described in FIG. 1, wherein Tyr served as a control. Mean fluorescence at 1 mM is presented.
Figure 7:
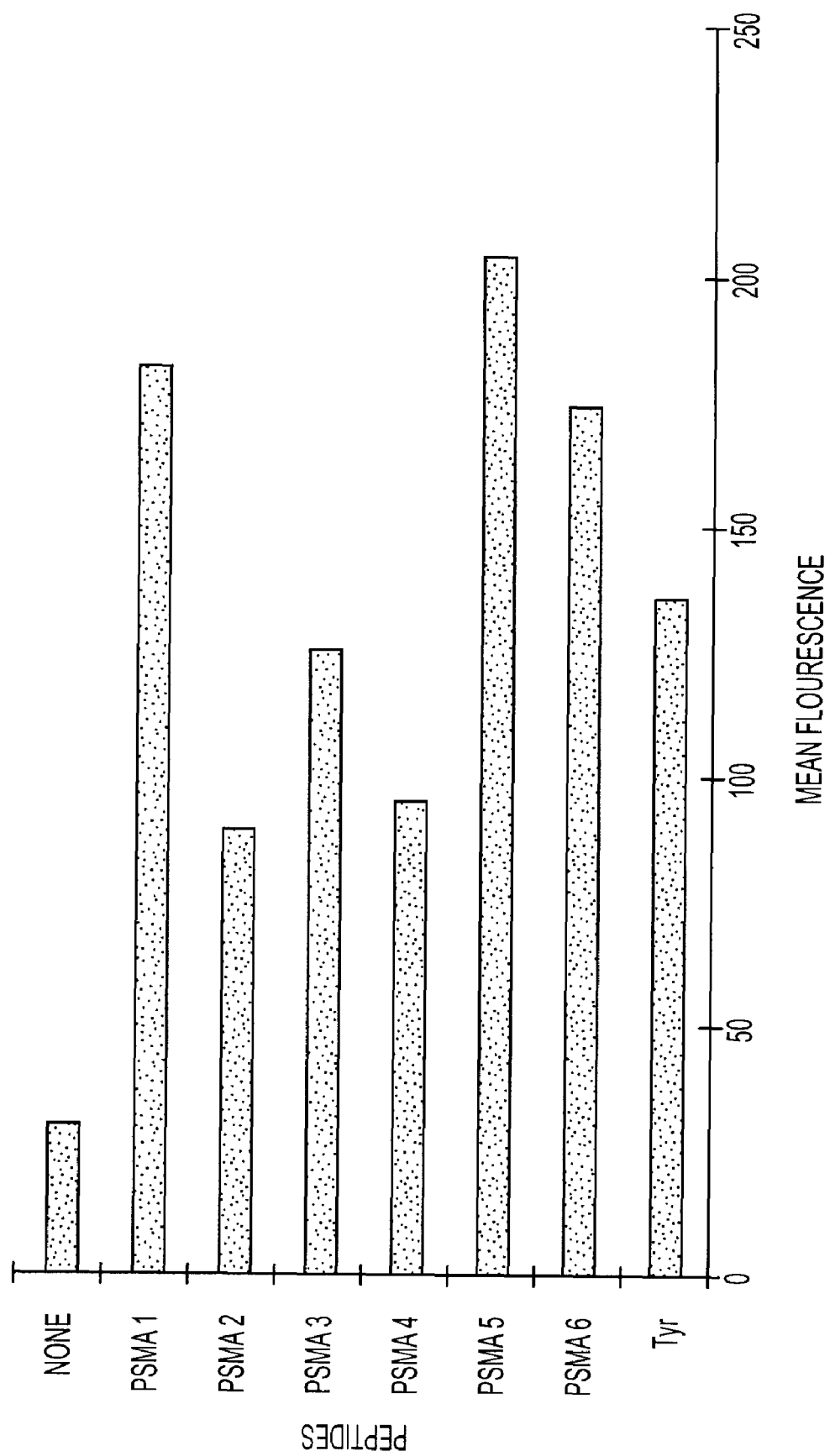
FIG. 7 demonstrates stabilization of cell surface HhD on RMA-S cells by human Prostate specific membrane antigen (PSMA) derived peptides. PSMA derived peptides (1 μM-1 mM) were loaded and cells were monitored as described in FIG. 6.

PSA, PSMA and PAP Homologue Peptides are Immunogenic CTL Epitopes in HLA-A2 Transgenic H-2 $D^b$, $\beta$2m Double Knockout Mice Carcinoma of the prostate (CAP) is the most prevalent cancer and the second cause of death in man (53). The use of prostate specific antigen (PSA) in early detection of CAP has caused a stage shift of the disease (54). By now, 70% of CAP cases are detected when they are still organ confined. These patients may be cured by radical prostatectomy or by radiation therapy. However, the long term cancer specific survival of organ confined disease after radical prostatectomy, even in the best series, is only 70% (55). Patients with large tumors, high grade tumors and those with seminal vesicle invasion, or positive lymph nodes are at increased risk of metastases and death due to CAP (56). However, CAP is a slow growing tumor and there is no effective adjuvant chemotherapy (57). Androgen ablation by surgical or medical means does not increase survival, but only increases time to recurrence and palliate symptomatic bone metastases (58). There is a need for an effective adjuvant or neo-adjuvant therapy for CAP and for systemic therapy for metastatic CAP. Thus, specific immunity is being investigated as a potential adjuvant therapy. PSA and prostate specific membrane antigen (PSMA) are proteins which are expressed almost exclusively in prostate tissue, benign or malignant and are differentiation antigens. Prostate acid phosphatase (PAP) is expressed also in other tissues but its concentration is much higher in prostate tissue. In a few studies, 3 PSA homologue peptides (59-60) and 2 PSMA homologue peptides (61-62) were found to be immunogenic and to induce specific CTL by repeated in vitro stimulation of peripheral blood lymphocytes from CAP patients. In one of these studies (62), patients with metastatic prostate cancer were immunized with the 2 immunogenic PSMA peptides, loaded on dendritic cells. There was some partial responses expressed by a reduction in PSA levels and some objective reduction in bone metastases burden. However, the procedures used to induce CTL lines in vitro are cumbersome, lengthy and not reliable. Some CTL peptide epitopes which bind with high affinity to MHC class I may induce tolerance and will be not detected. Moreover, repeated in vitro stimulations, necessary for inducing CTL lines may select CTL which have a growth advantage in culture and not the most potent and specific CTL in vivo. Herein the HLA-A2 transgenic, H-2 $D^{b-/-}$ $\beta$2m$^{-/-}$ double knockout mice (HhD mice) was used for identification of novel prostate cancer specific CTL epitopes. Peptides homologue to PSA, PSMA and PAP, which are expressed mainly in benign or malignant prostate tissue, were evaluated for their capacity to induce specific CTL in HhD mice. The amino acid sequences of these proteins (NCBI accession Nos. 296671, 2897946 and 439658) were screened by a HLA binding motif program. The peptides which were predicted to bind to HLA-A2 were synthesized (Tables 4, 5, 6) and their binding affinity was tested on RMA-S-HhD cells (TAP deficient cells, capable of presenting only exogenous peptides and which were transfected with the HhD construct) by FACS (FIGS. 6 and 7). The peptides with high binding affinity were used for immunization of HhD mice. Five PSA homologue peptides, in addition to the peptides detected by other authors, 6 PSMA homologue peptides, including the 2 peptides detected by other authors (PSMA 5 and 6) and 4 PAP homologue peptides were found.

TABLE 4

Predicted human prostate specific antigen (PSA) peptides that bind to HLA-A2

| Peptide | Sequence | Amino acids* | SEQ ID: |
|---|---|---|---|
| PSA1 | DLHVTSNDV | 175-183 | 20 |
| PSA2 | VLVHPQWVL | 53-61 | 21 |
| PSA3 | FLRPGDDSS | 110-118 | 22 |
| PSA4 | ALGTTCYAS | 147-155 | 23 |
| PSA5 | KLQCVDLHV | 170-178 | 24 |

The prediction program is described in Materials and Methods. The peptides are listed in descending order of predicted HLA-A2.1-peptide complex stability. Single letter amino acid codes and the position of the peptide in the protein are listed.
*Numbering is according to NCBI accession No. 296671.

TABLE 5

Predicted human prostate specific membrane antigen (PSMA) peptides that bind to HLA-A2

| Peptide | Sequence | Amino acids* | SEQ ID: |
|---|---|---|---|
| PSMA1 | ELAHYDVLL | 109-117 | 25 |
| PSMA2 | NLNGAGDPL | 260-268 | 26 |
| PSMA3 | TLRVDCTPL | 461-469 | 27 |
| PSMA4 | MMNDQLMFL | 663-671 | 28 |
| PSMA5 | ALFDIESKV | 711-719 | 29 |
| PSMA6 | LLHETDSAV | 4-12 | 30 |

The prediction program is described in Materials and Methods. The peptides are listed in descending order of predicted HLA-A2.1-peptide complex stability. Single letter amino acid codes and the position of the peptide in the protein are listed.
*Numbering is according to NCBI accession No. 2897946.

TABLE 6

Predicted human prostate acid phosphatase (PAP) peptides that bind to HLA-A2

| Peptide | Sequence | Amino acids* | SEQ ID: |
|---|---|---|---|
| PAP1 | VLAKELKFV | 30-38 | 31 |
| PAP2 | ILLWQPIPV | 135-143 | 32 |
| PAP3 | DLFGIWSKV | 201-209 | 33 |
| PAP4 | PLERFAELV | 352-360 | 34 |

The prediction program is described in Materials and Methods. The peptides are listed in descending order of predicted HLA-A2.1-peptide complex stability. Single letter amino acid codes and the position of the peptide in the protein are listed. *Numbering is according to NCBI accession No. 439658.

HhD mice were immunized and boosted twice with the PSA, PSMA, or PAP peptides. Peptides were loaded individually on RMA-S-HhD cells and equal numbers of pulsed cells were mixed in the vaccine. Mice were also immunized with CAP peptide extract, or with DU145-HhD, a CAP cell line transfected with the HhD construct. Lymphocytes were obtained from the spleen of these mice and restimulated once, in vitro with the corresponding peptide tumor extract or cells. PSA, PSMA, PAP, CAP and normal prostate peptide extract and DU145-HhD cells were screened by the CTL obtained from these mice. The results are expressed as lytic units (LU) which represent $10^6$/Number of CTL effectors which induce 30% specific target lysis. More lytic units signify a more potent CTL response.

Figure 8:
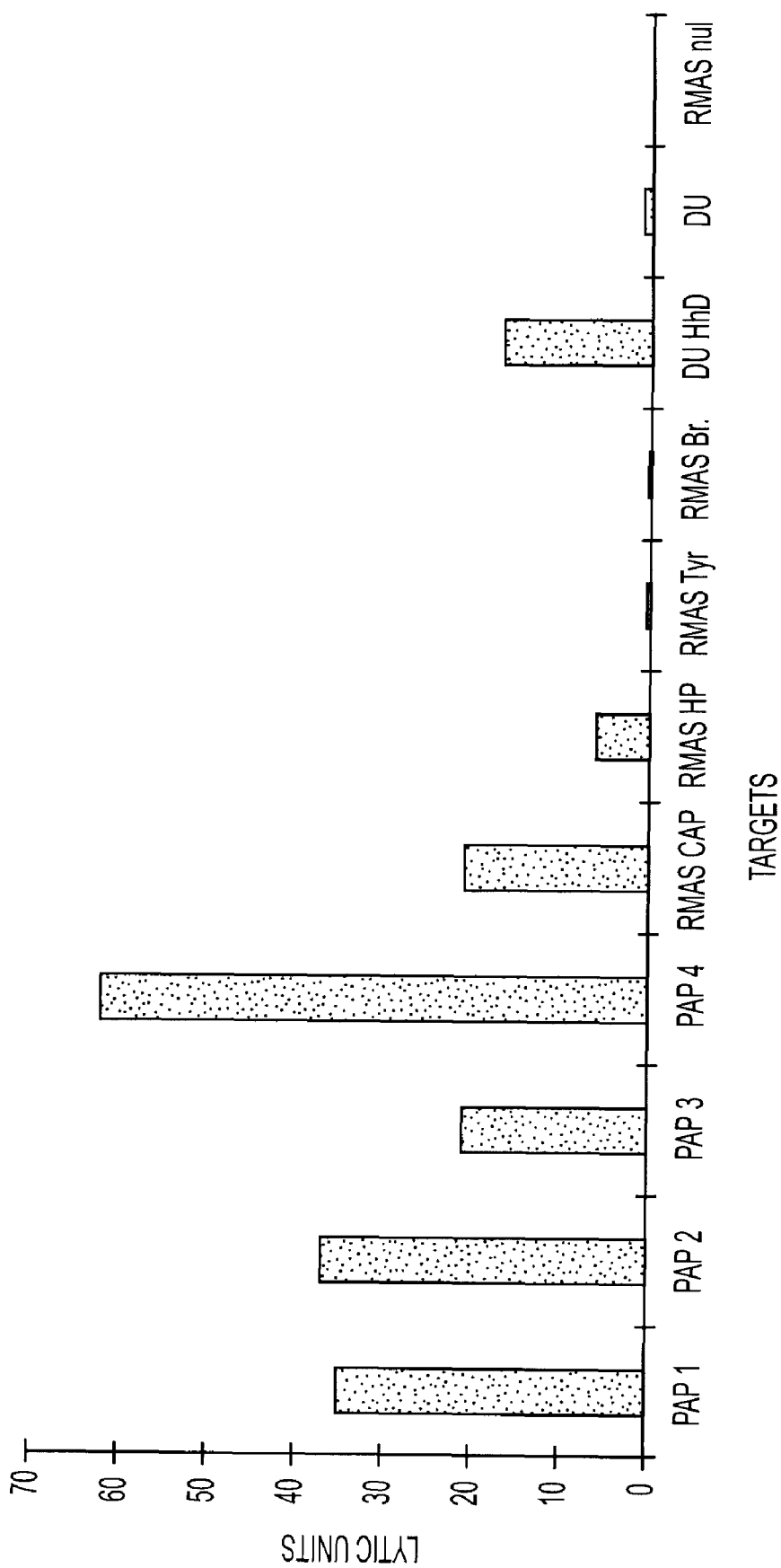
FIG. 8 demonstrates immunogenicity and antigenicity of PAP derived peptides in HhD mice. HhD mice were immunized as described, by RMA-S-HhD-B7.1 cells loaded individually with each PAP peptide and pooled before vaccination. CTL were tested against RMA-HhD cells loaded with synthetic peptides (PAP 1-4), prostate carcinoma extracted peptides (RMA-S, CAP), hyperplastic (normal) prostate extracted peptides (RMA-S HP), breast carcinoma derived peptides (RMA-S Br, control) and tyrosinase (RMA-S Tyr, control). The prostate carcinoma cell line DU145 (DU) and its HhD transfectant (DU HhD) were also tested as targets. The results are presented in lytic units as in FIG. 4.
Figure 9:
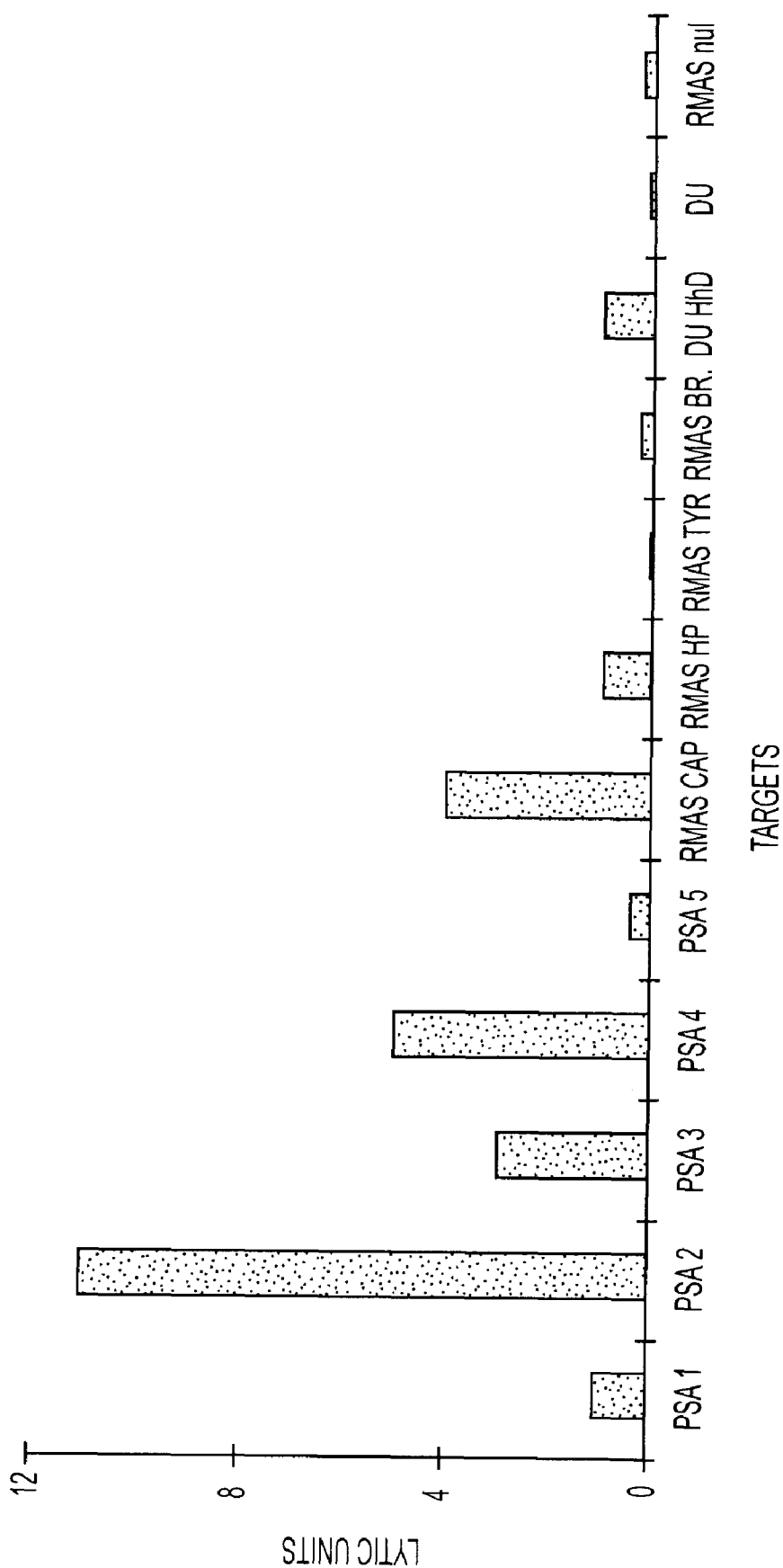
FIG. 9 demonstrates immunogenicity and antigenicity of PSA derived peptides in HhD mice. Procedures were performed and results are presented as in FIG. 8.
Figure 10:
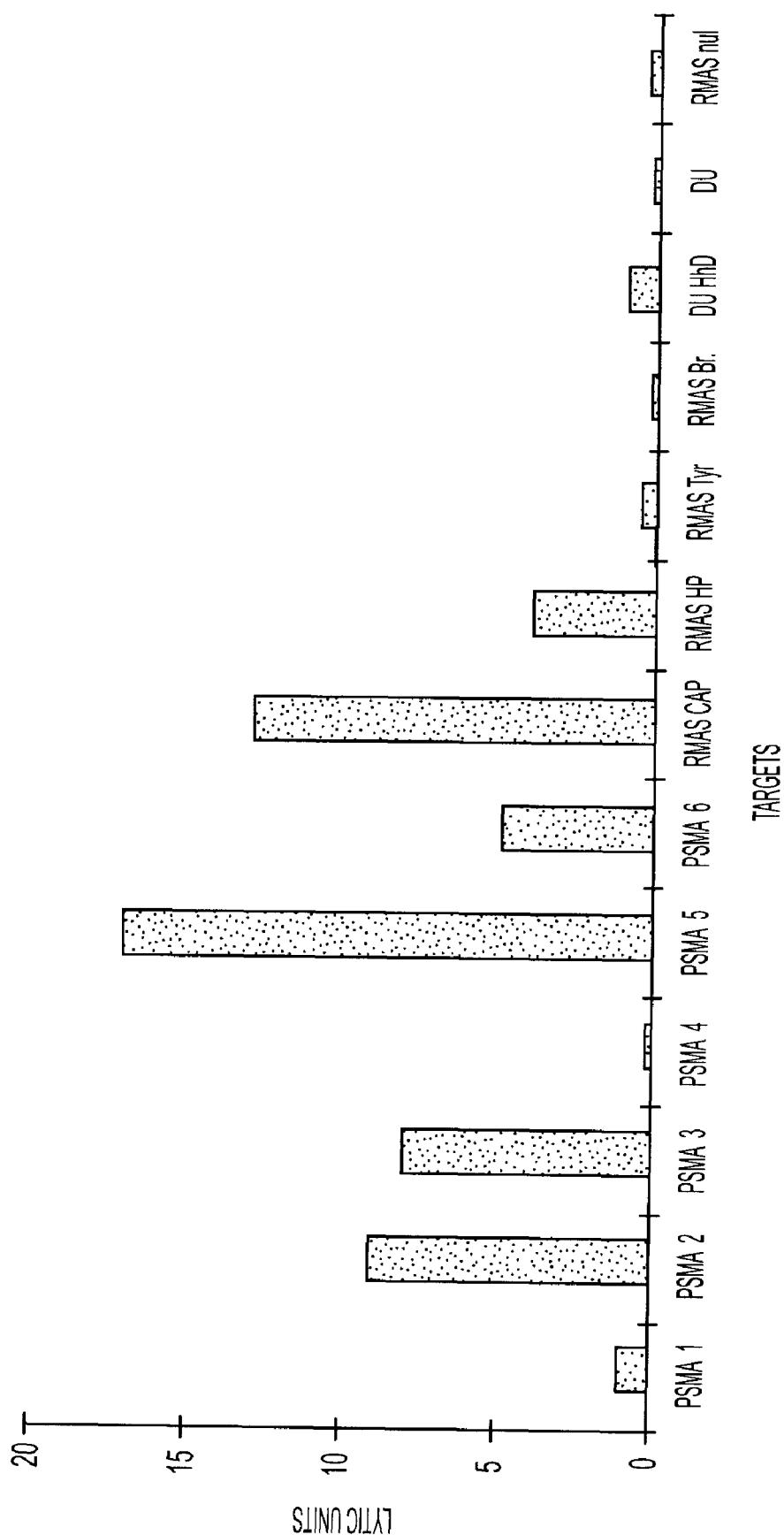
FIG. 10 demonstrates immunogenicity and antigenicity of PSMA derived peptides in HhD mice. Procedures were performed and results are presented as in FIG. 8.
Figure 11:
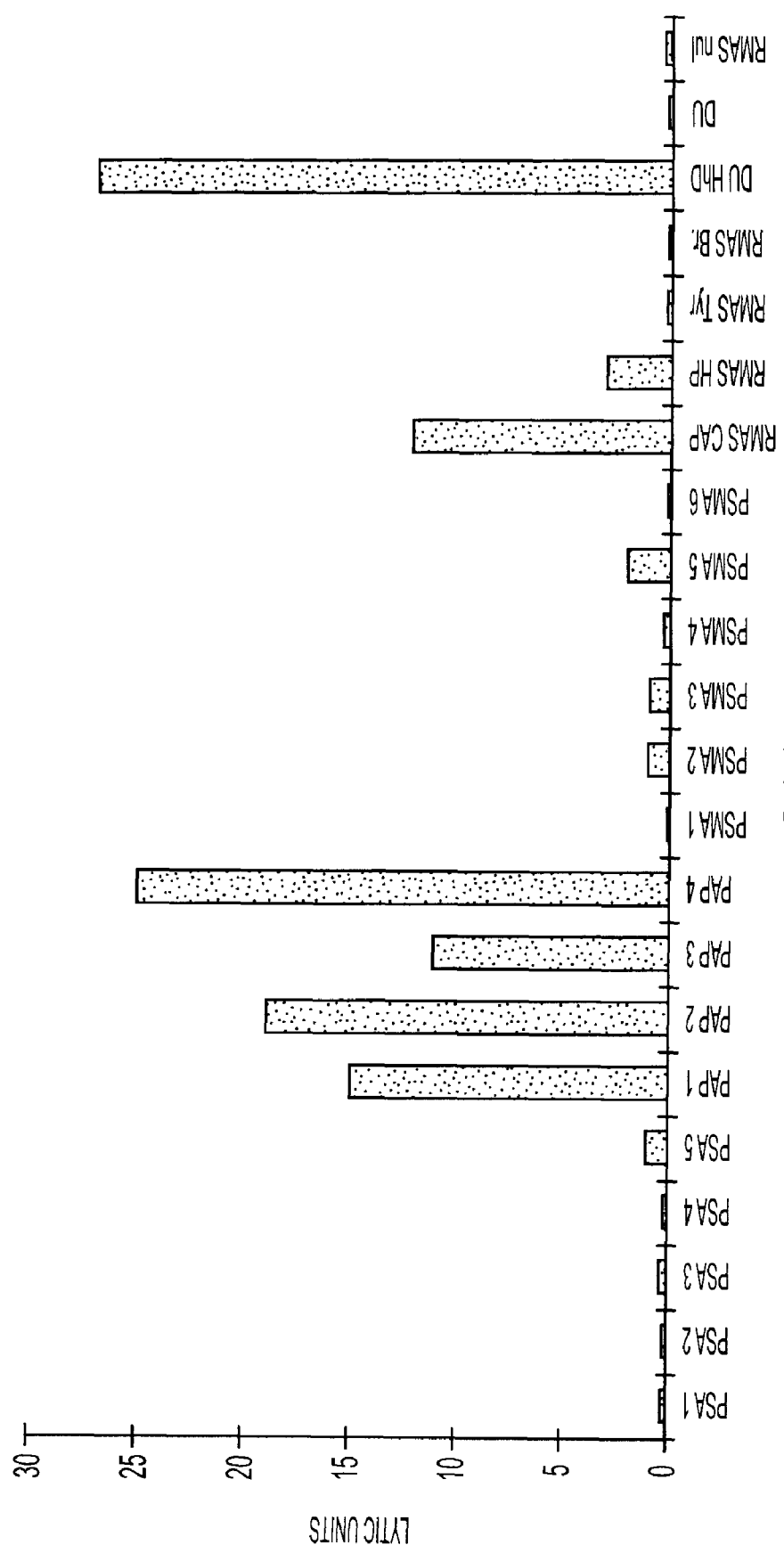
FIG. 11 demonstrates lysis of PSA, PAP and PSMA derived peptide loaded RMA-S-HhD cells by CTL induced against DU145-HhD cells in HhD mice. Mice were immunized with irradiated DU145-HhD cells and CTL assays were performed as described in Materials and Methods. Labeled RMA-S-HhD target cells were loaded with synthetic PSA (1-5), PAP (1-4), PSM-A (1-6) or tyrosinase (RMA-S Tyr) peptides, with prostate carcinoma (RMA-S CAP), breast carcinoma (RMA-S Br.) or hyperplastic prostate (RMA-S HP) extracted peptides. DU145 (DU) and DU145-HhD also served as targets. The results are presented in lytic units as in FIG. 4.
Figure 12:
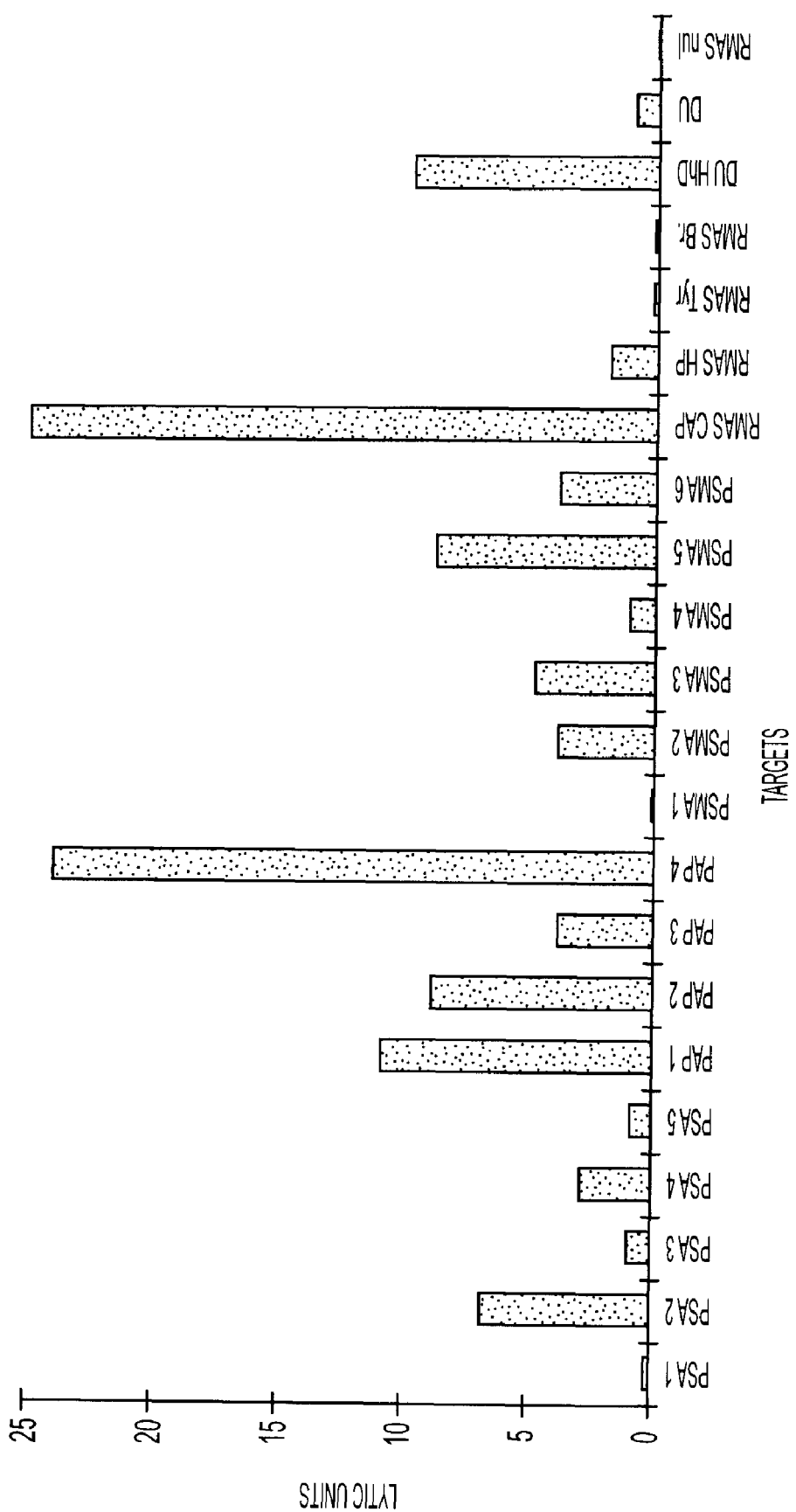
FIG. 12 demonstrates lysis of PSA, PAP and PSMA derived peptide loaded RMA-S-HhD by CTL induced against prostate carcinoma extracted peptides in HhD mice. HhD mice were immunized with RMA-S-HhD-B7.1 cells loaded with peptides extracted from prostate carcinoma samples. Experimental details are equivalent to the details in FIG. 11.

CTL from HhD mice immunized with PAP peptides induced intense lysis of RMA-S-HhD cells (targets) loaded with PAP homologue peptides (20 to 65 LU, FIG. 8). Three out of 5 PSA homologue peptides induced significant and specific lysis of targets loaded with the corresponding peptide (5.2 to 11.4 LU, FIG. 9). Four out of 6 PSMA homologue peptides induced significant lysis of the targets loaded with the corresponding peptide (5 to 17 LU, FIG. 10). Two out of these 4 peptides were found to be immunogenic by other authors, by in vitro stimulation of human peripheral blood lymphocytes. CTL obtained from each group of immunized HhD mice induced significant lysis of targets loaded with CAP peptide extract (4.5 to 22 LU). There was significantly less lysis of normal prostate peptide extract loaded targets than of the CAP peptide extract loaded targets for each immunizing peptide (FIGS. 8, 9 and 10). Also, there was intense lysis of DU-145-HhD cells by CTL obtained from HhD mice immunized with these cells (FIG. 11), or immunized by PAP homologue peptides, or CAP peptide extract (28, 19 and 11 LU, respectively, FIG. 12). There was no significant lysis of DU145-HhD cells by CTL derived from HhD mice immunized with PSA, or PSMA homologue peptides. These findings result probably from low expression of PSA and PSMA by DU145 cells.

There was good cross reactivity between CTL derived from mice immunized with CAP peptide extract and PSA, PSMA and PAP homologue peptides, which were found to be immunogenic in HhD mice. The CTL derived from mice immunized with DU145-HhD cells cross reacted with the immunogenic PAP homologue peptides (11 to 26 LU) CAP peptide extract (12 LU), and less with normal prostate peptide extract (3 LU). Overall, there was no lysis of targets loaded with nonspecific peptides such as breast cancer peptide extract, or HLA-A2 binding tyrosinase homologue peptide. Also, there was no lysis of RMA-S-HhD cells without peptides and there was no lysis of non transfected DU 145 cells (HLA-A2 negative). The internal organs of the HhD mice immunized with PSA, PSMA, PAP homologue peptides, or with CAP peptide extract, or with DU145-HhD cells, were formalin fixed and representative slices from each organ were stained with hematoxyllin and eosin. Two non-immunized HhD mice served as control. There was no pathological finding such as tissue necrosis or inflammatory infiltrate in any of the organ examined.

Example 3

Breast Specific CTL Induction by BA-46 (Lactadherin) Peptides and by MUC1 Peptides in HhD Mice Breast cancer is the second leading cause of cancer death among women in the Western World and the leading cause of death among women at the age of 30 to 70. Breast cancer afflicts 200,000 women per annum in the USA today. The highest mortality is restricted to patients whose regional lymph nodes are involved. Early detection, followed by surgery provides good prognosis. In patients with occult lymph node metastasis, adjuvant chemotherapy or hormonal therapy for breast cancer have been proven to be effective, yet a large fraction of patients will succumb to metastasis. (63).

As pointed out above, TAA vaccines may constitute an additional treatment modality for residual disease. A number of tumor associated antigens have been described for breast carcinomas. The MUC-1 Mucin, a high molecular weight glycoprotein is highly expressed on breast carcinomas. Specific, MHC-unrestricted recognition of MUC-1 by human cytotoxic T cells were demonstrated (64). More recently peptides from MUC-1 were shown also to induce MHC class I and MHC class II restricted responses (65, 66). HER2/neu derived peptides were shown to be recognized by CTL from breast carcinoma patients (67).

BA-46 is a 46 kDa transmembrane-associated glycoprotein of the human milk fat globule membrane (HMFG), that is overexpressed in human breast carcinomas (68). The protein contains cell adhesion sequences (RGD), supports RGD based adhesion and interacts with integrin (69). It also contains an EGF-like domain, and a phospholipid binding sequence C1/C2-like domain of coagulation factor V and VIII. BA-46 is present in the circulation of breast cancer patients but not in healthy individuals (70). Moreover, anti BA-46 radio-conjugated monoclonal antibodies, have successfully targeted human breast tumors transplanted into mice (71). Herein we tested MUC1 and BA-46 derived peptides as potential TAA peptides in the HhD mouse system. BA-46 homologous peptide vaccines induce HLA-A2 restricted CTL which preferentially recognize breast tumor derived peptides.

BA-46 is overexpressed in many breast carcinomas, yet, no cellular immunity to BA-46 protein has been reported so far. We evaluated peptides complementary to the amino acid sequences of human BA-46, The sequence was screened for HLA-A2 binding motifs by a HLA binding motif program. Seven 9-mer peptides which were predicted to bind with high affinity to HLA-A2 were selected and synthesized (Table 7).

TABLE 7

Predicted human breast associated BA-46 peptides that bind to HLA-A2

| Peptide  | Sequence  | Amino acids* | SEQ ID: |
|----------|-----------|--------------|---------|
| BA-46-1  | KQGNFNAWV | 271-279      | 35      |
| BA-46-2  | NLLRRMWVT | 131-139      | 36      |
| BA-46-5  | NLFETPILA | 356-364      | 37      |
| BA-46-6  | NLFETPVEA | 194-202      | 38      |
| BA-46-7  | GLQHWVPEL | 97-105       | 39      |
| BA-46-8  | VQFVASYKV | 313-321      | 40      |
| BA-46-9  | RLLAALCGA | 5-13         | 41      |

The prediction program is described in Materials and Methods. The peptides are listed in descending order of predicted HLA-A2.1-peptide complex stability. Single letter amino acid codes and the position of the first amino acid of the peptide in the protein sequence as well as the calculated binding score are listed.
*Numbering is according to NCBI accession No. 1589428 (SEQ ID NO:78).

Figure 13:
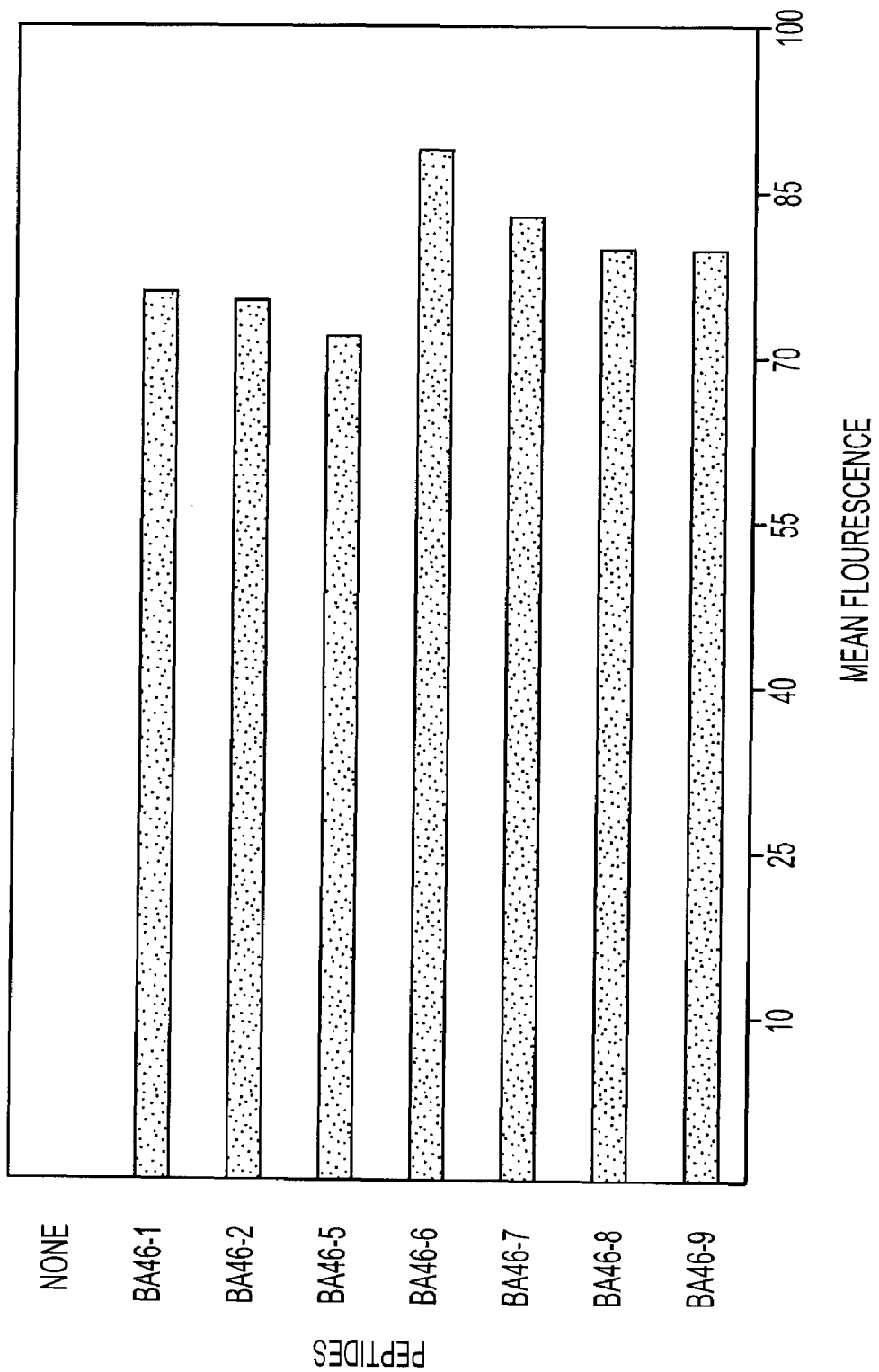
FIG. 13 demonstrates stabilization of cell surface HhD on RMA-S-cells by human BA-46 (Lactadherin) derived peptides. RMA-S-HhD cells were incubated with 1-100 μM synthetic peptides and monitored as described in FIG. 1.

All peptides bound well to the HhD molecules expressed on RMA-S transfectant (FIG. 13). HhD mice were vaccinated three times at weekly interval using $2 \times 10^6$ RMA-S-HhD/B7.1 with either tumor extract prepared from 5 samples of breast carcinoma by acid extraction and separation of molecules <3 Kd, or with a pool of BA-46 peptides. Ten days after the last immunization, HhD spleen-derived antigen presenting cells (APC) were pulsed for 3 hour at 37° C. with either breast tumor extract or a BA-46 peptide pool, followed by incubation with the rest of the splenocytes for 4 more days. BA-46 peptides, breast extracted peptides and normal breast extracted peptides were loaded on labeled RMA-S-HhD cells and were screened by cytotoxic T lymphocytes (CTL) obtained from the HhD mice as described before (62).

Figure 14:
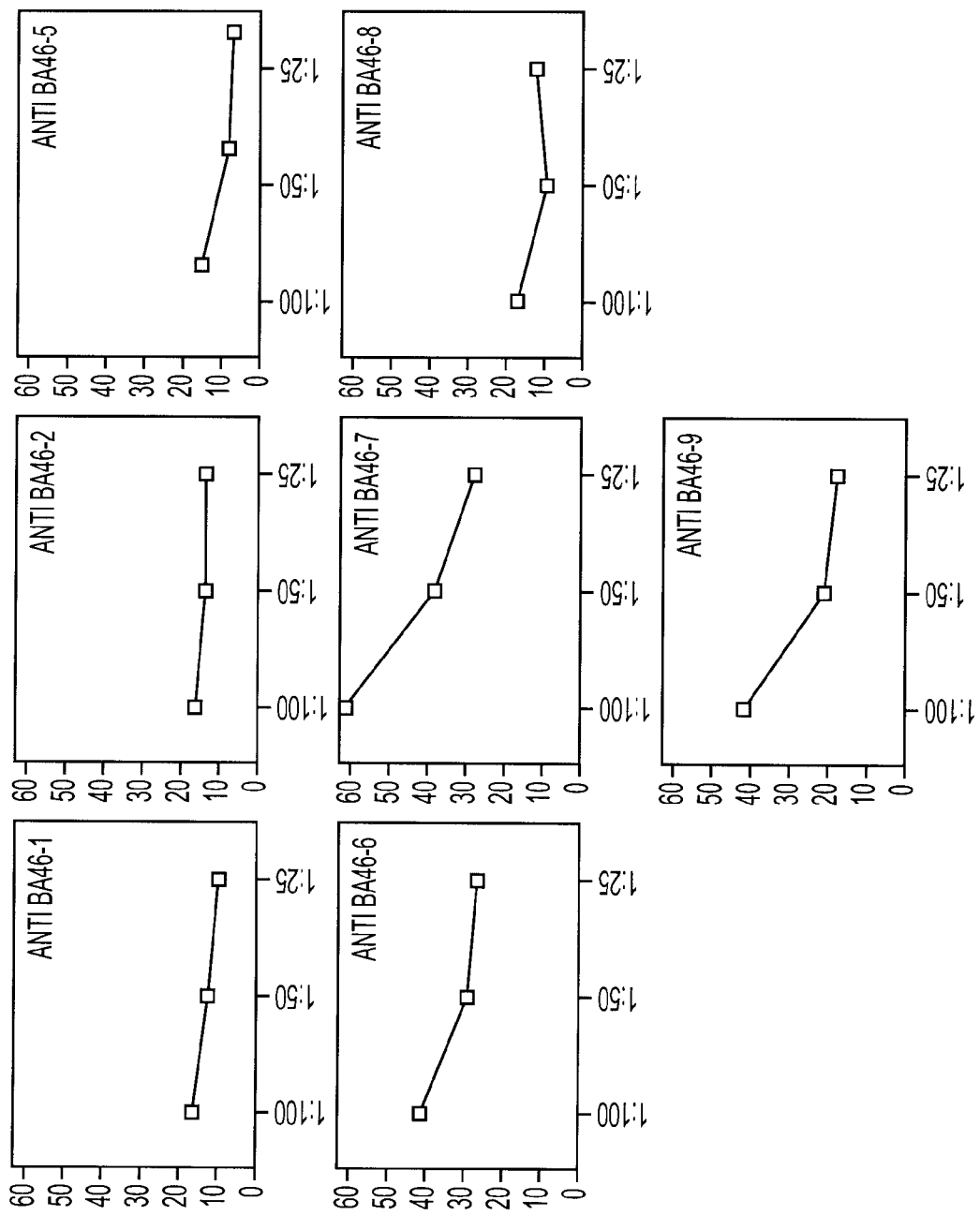
FIG. 14 demonstrates immunogenicity of BA-46 peptides in HhD mice. Mice were immunized as described in Materials and Methods, with RMA-S-HhD-B7.1 cells loaded with synthetic peptides. CTL assays were performed on RMA-S-HhD target cells loaded with homologous peptides.
Figure 15:
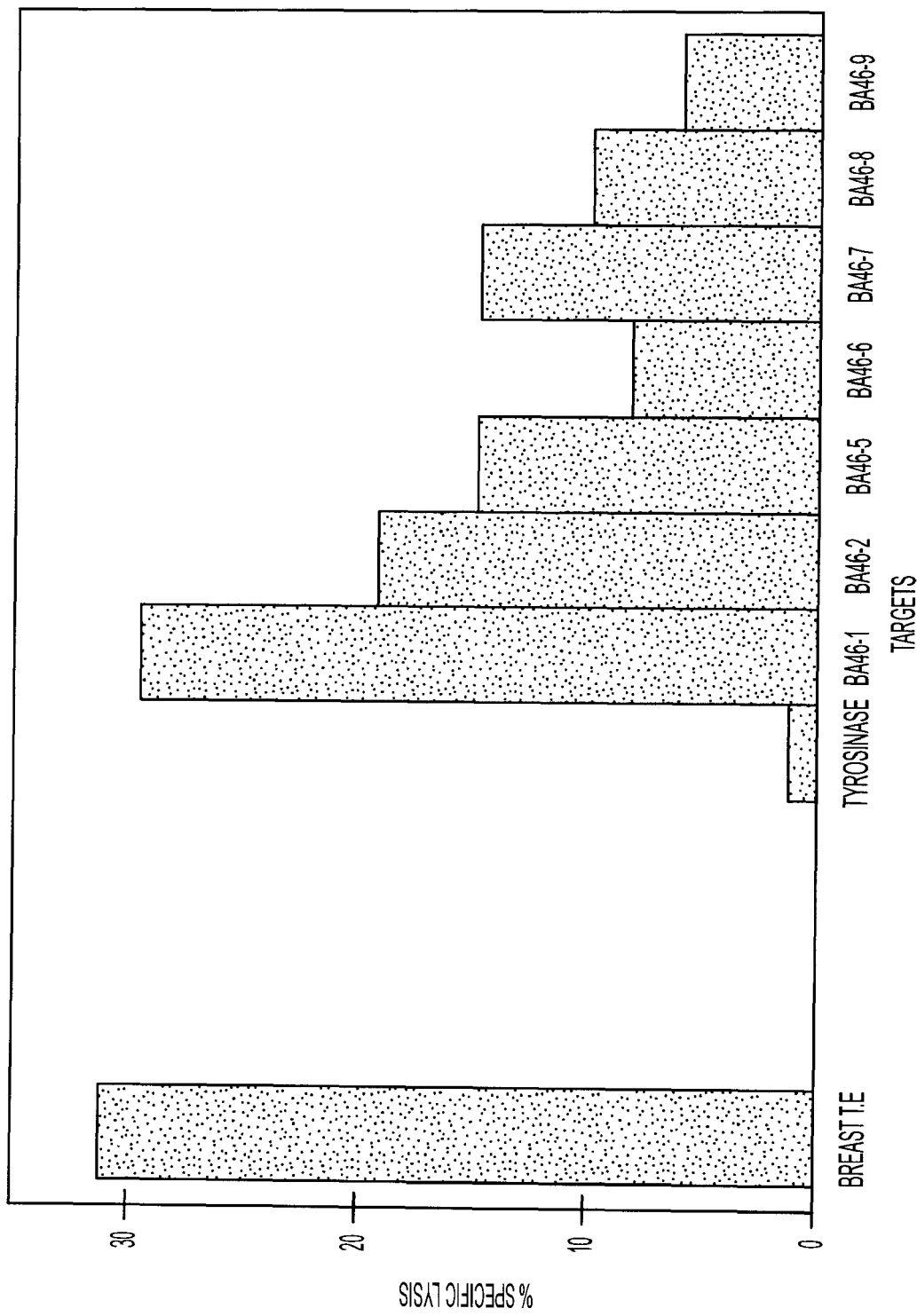
FIG. 15 demonstrates lysis of BA-46 peptide loaded targets by CTL induced against breast carcinoma extracted peptides in HhD mice. HhD mice were immunized with RMA-S-HhD-B7.1 cells loaded with peptides extracted from breast carcinoma samples. Experimental details are as in FIG. 11. The data is presented as percent specific lysis at E:T of 100:1.
Figure 16:
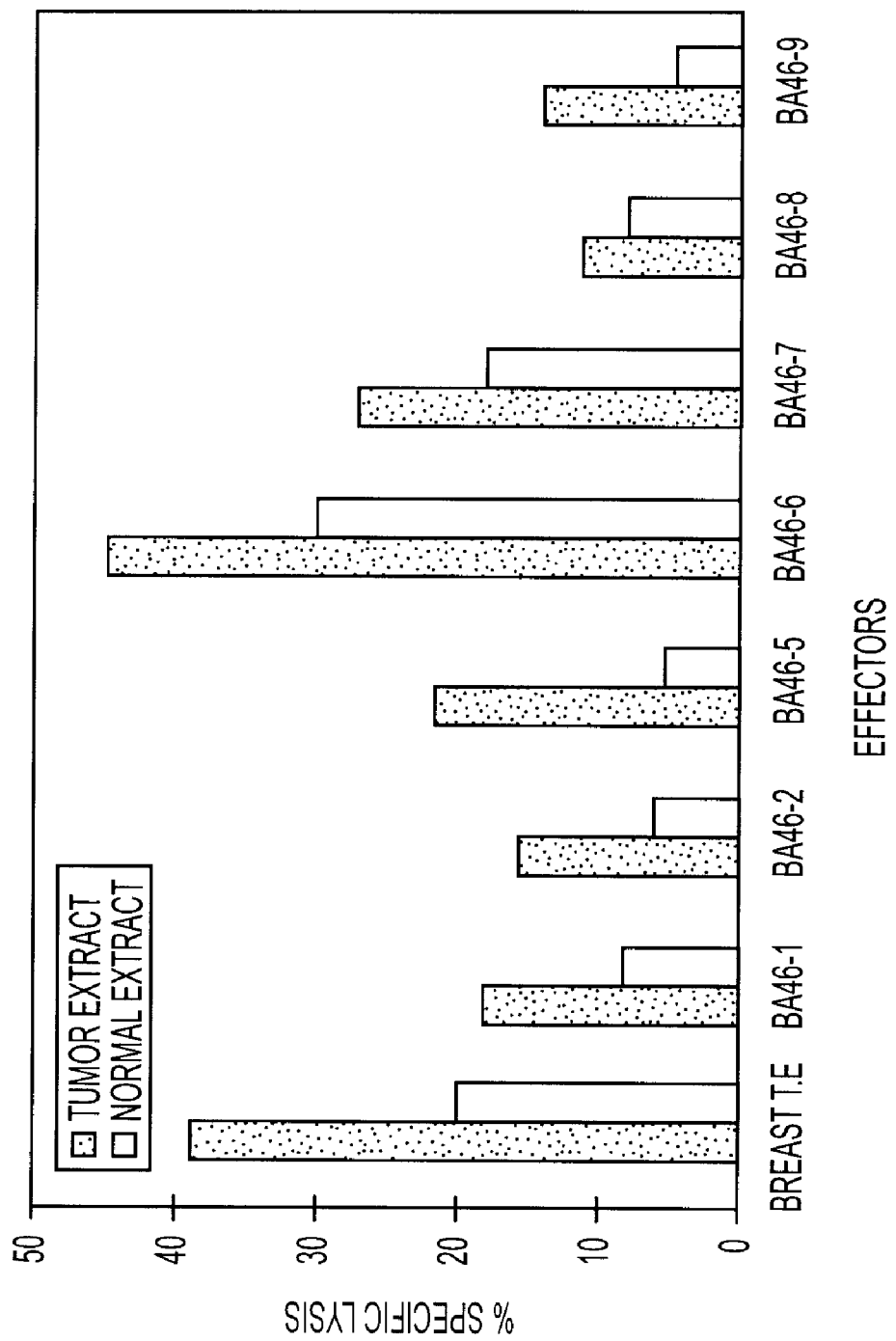
FIG. 16 demonstrates differential lysis of tumor extracted peptide loaded target cells by CTL induced again tumor peptides or BA-46 derived peptides in HhD mice. Mice were immunized by RMA-S-HhD-B7.1 cells loaded with synthetic BA-46 derived peptides or breast carcinoma derived peptides as described in Materials and Methods. CTL were tested against RMA-S-HhD cells loaded with breast carcinoma extracted peptides or normal breast tissue extracted peptides. Percent specific lysis at E:T of 100:1 is presented.
Figure 17:
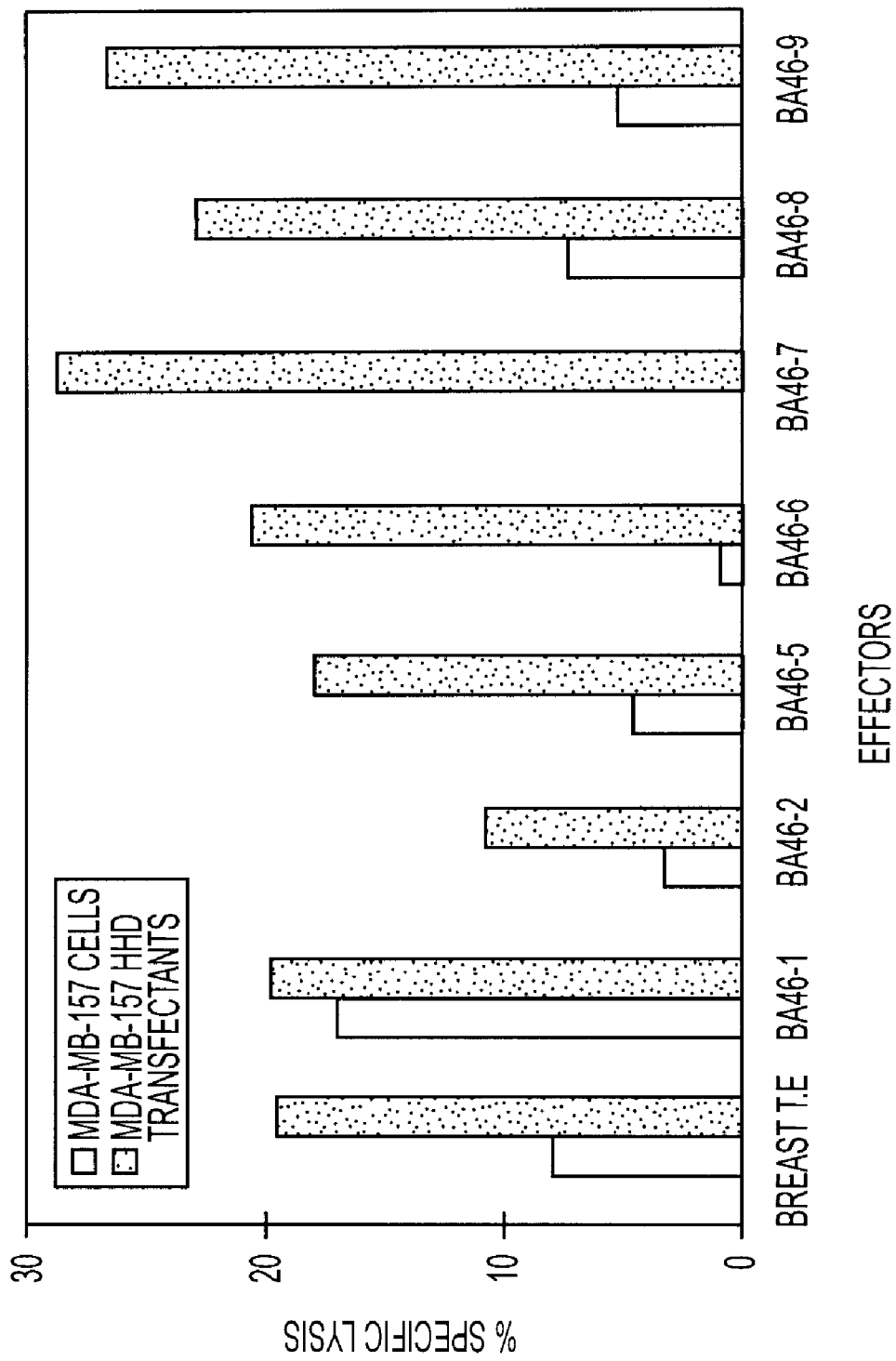
FIG. 17 demonstrates HLA-A2.1 (HhD) restricted lysis of a breast carcinoma cell line by CTL induced against BA-46 derived peptides or tumor extracted peptides. HhD mice were immunized as in FIG. 16 and CTL were tested against the HLA negative MDA-MB-157 and their HhD transfectants. The data is presented in percent specific lysis at a E:T of 100:1.

Anti BA-46 peptide CTL activity showed variability in immunogenicity at a range between 20% to 60%. Lysis of 60% was obtained against BA-46-7, 40% against BA-46-6, BA-46-9 and 20% against the rest of the peptides (FIG. 14). CTL from HhD mice immunized with breast tumor extract peptide induced 10% to 30% specific lysis of BA-46 peptide loaded RMA-S-HhD cells, 31% lysis of tumor extract loaded targets and only 12% and 14% lysis of normal breast extracted peptides and colon extracted peptides loaded RMA-S-HhD cells, respectively. No lysis of the melanoma associated synthetic tyrosinase peptide was obtained (FIG. 15). The ability of BA-46 peptides to induce a breast associated CTL reaction that is HLA-A2.1 restricted was further examined. CTL against individual BA-46 peptides showed 30-50% higher activity against breast tumor extract versus normal breast loaded target cells, supporting the fact that a preferential activity is obtained against breast tumor TAAs. These effectors also lysed preferentially a breast carcinoma line-HhD transfectant relative to parental cells, stressing the HLA-A2 restriction of the reaction (FIGS. 16 and 17).

Example 4

Characterization of Novel Breast Carcinoma MUC1 Derived Peptides as CTL Epitopes The polymorphic epithelial Mucin, encoded by the MUC-1 gene is a high molecular weight transmembranal glycoprotein overexpressed in a broad range of tumors, such as breast, pancreas, ovary, thyroid and myeloma (72) cancer. It was found that the growth rate of primary breast tumors induced by the polyoma middle T antigen is significantly slower in MUC-1 null mice, suggesting that MUC-1 might play a role in the progression of mammary carcinoma (73). Furthermore, high level of MUC-1 expression by human breast cancer cells was found to be directly correlated with the presence of axially lymph node metastasis (74). A major feature of the MUC-1 molecule is the presence of an highly immunogenic extracellular tandem repeat array (TRA) heavily O-glycosidic-linked serine and threonine residues (75). Altered carbohydrate structure of MUC-1 in breast cancer cells, is probably responsible for the exposure of core epitopes within MUC-1, specifically recognized by monoclonal antibodies, as well as non MHC-restricted cytotoxic T lymphocytes (76). HLA-A11 (77) and more recently for HLA-A2.1 (78) restricted responses to the extracellular TRA have also been reported. However it was suggested that Mucin can actively suppress cell-mediated response against glycosylated TRA (79), or induced direct T cell apoptosis (80). More recently Agrawal et al showed that synthetic peptides derived from MUC-1 TRA cause suppression of human T-cell proliferative responses (81). This data points out the ambiguous role of MUC-1 TRA in T cell activation.

A series of peptides derived from non-TRA domains of the MUC-1 as potential CTL epitopes. The MUC-1 sequence was screened for potential HLA-A2.1 binding peptides (Table 8) and the eight peptides were synthesized.

TABLE 8

Predicted human breast associated MUC-1 peptides that bind to HLA-A2

| Peptide  | Sequence  | Amino acids* | SEQ ID: |
|----------|-----------|--------------|---------|
| MUC1-/C6 | LLLLTVLTV | 31-40        | 42      |
| MUC1-/D6 | LLLTVLTVV | 32-41        | 43      |
| MUC1-/F6 | FLSFHISNL | 323-331      | 44      |
| MUC1-/A5 | LLVLVCVLV | 442-451      | 45      |
| MUC1-/F4 | ALLVLVCVL | 441-450      | 46      |
| MUC1-/B5 | SLSYTNPAV | 519-528      | 47      |
| MUC1-/A7 | NLTISDVSV | 412-421      | 48      |
| MUC1-/E6 | ALASTAPPV | 226-234      | 49      |

The prediction program is described in Materials and Methods. The peptides are listed in descending order of predicted HLA-A2.1-peptide complex stability. Single letter amino acid codes and the position of the first amino acid of the peptide in the protein sequence as well as the calculated binding score are listed.
*Numbering is according to NCBI accession No. 182253.

Figure 18:
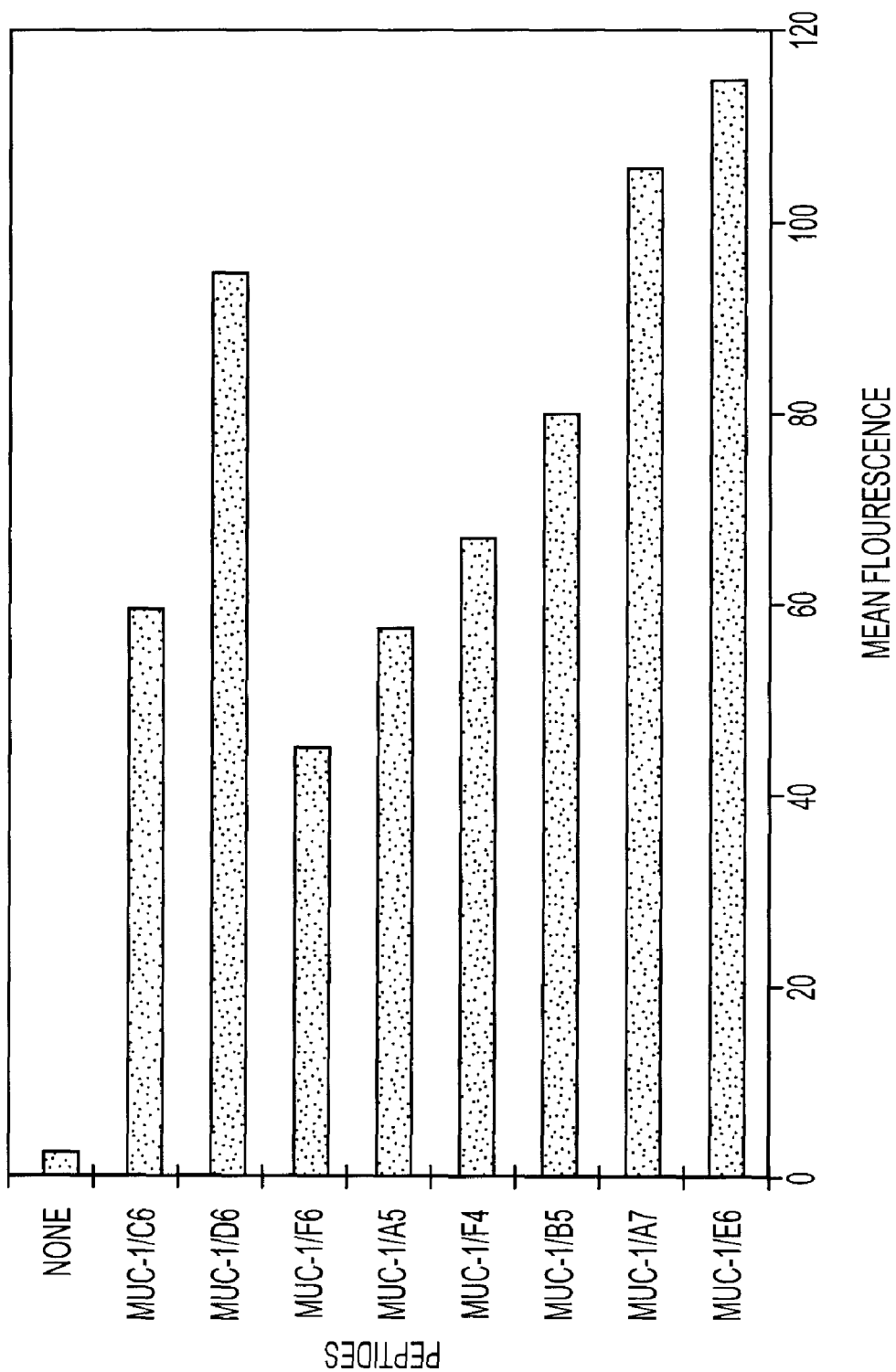
FIG. 18 demonstrates stabilization of cell surface HhD on RMA-S-cells by Mucin (MUC-1/A7, E6, D6) derived peptides. Details are as described in FIG. 1.

These 9 residue peptides are derived from the signal peptide, cytoplasmic and extracellular domains of the MUC-1 protein. Among these peptides only the MUC-1/B5 peptide has an identical sequence to the murine homologue. HLA-A.21 binding of MUC-1-derived peptides were evaluated by FACS analysis. The selected peptides were loaded on the murine TAP-deficient RMA-S-HhD transfectants and MHC stabilization was monitored (FIG. 18). Although all peptides bound efficiently at the 1-100 μM range, 3 peptides MUC-1/D6, MUC-1/E6 and MUC-1/A7 exhibited higher binding affinity. In addition, similar binding affinities of these peptides were obtained upon loading on human TAP deficient T2 cells, expressing endogenous HLA-A2.1 molecules (data not shown).

Figure 19:
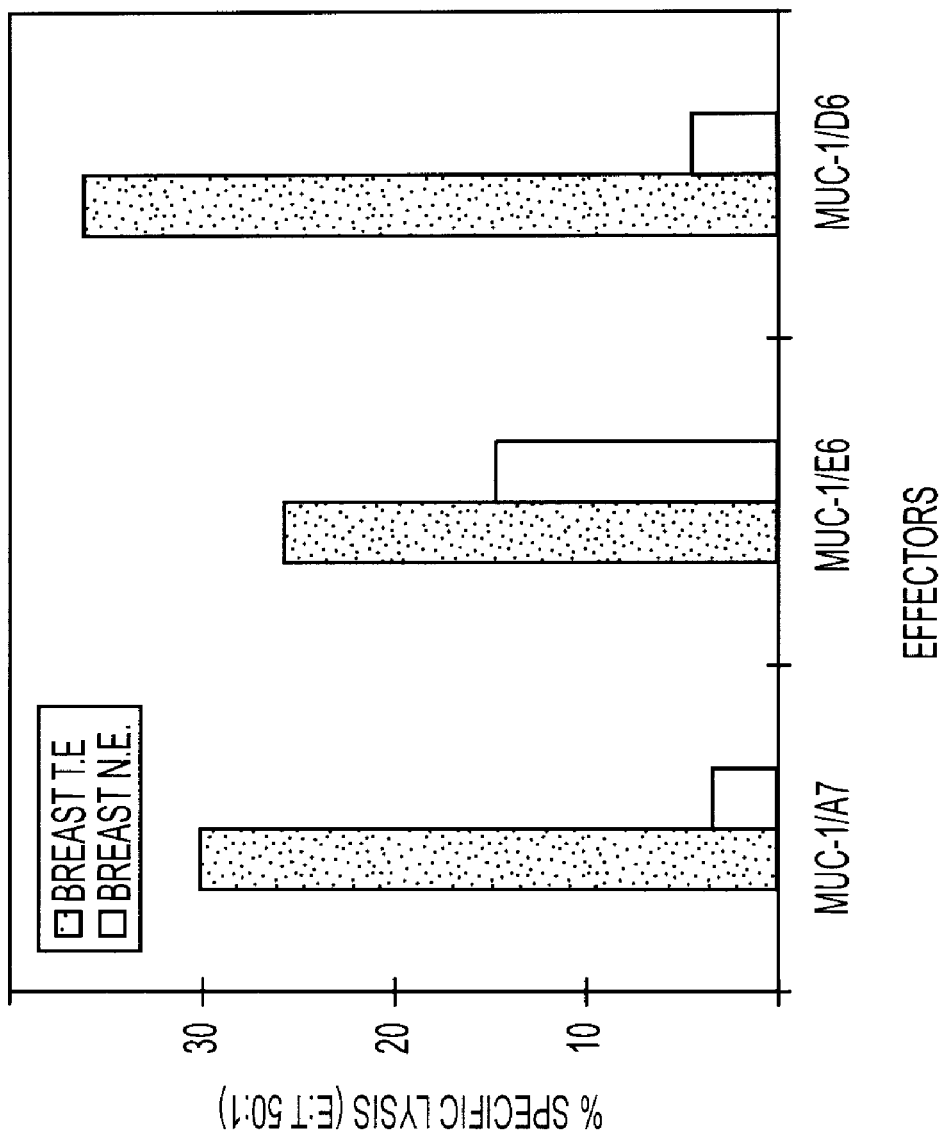
FIG. 19 demonstrates immunogenicity of MUC-1 derived peptides. HhD mice were immunized and CTL tested as in FIG. 14.

Synthetic peptides corresponding to the MUC-1 TRA epitopes were shown to induce CTL reaction in patients (77) as well as in HLA-A20.1 K$^b$ transgenic mice (78). Hence we primarily examined the lysis pattern of each of the particular peptides listed in Table 8 following an immunization with a pool of the MUC-1-derived synthetic peptides (FIG. 19). CTL results showed significant lysis of RMA-S-HhD target cells loaded either with the MUC-1/D6 peptide (38%) or with the MUC-1/A7 peptide (30%). Lower lysis rate of 15% with the MUC-1/E6 and with the MUC-1/F6 peptides was demonstrated. The rest of the peptides showed only background lysis properties. Hence MUC-1/D6, MUC-1/A7 and MUC-1/E6 harbor immunogenic properties.

Figure 20:
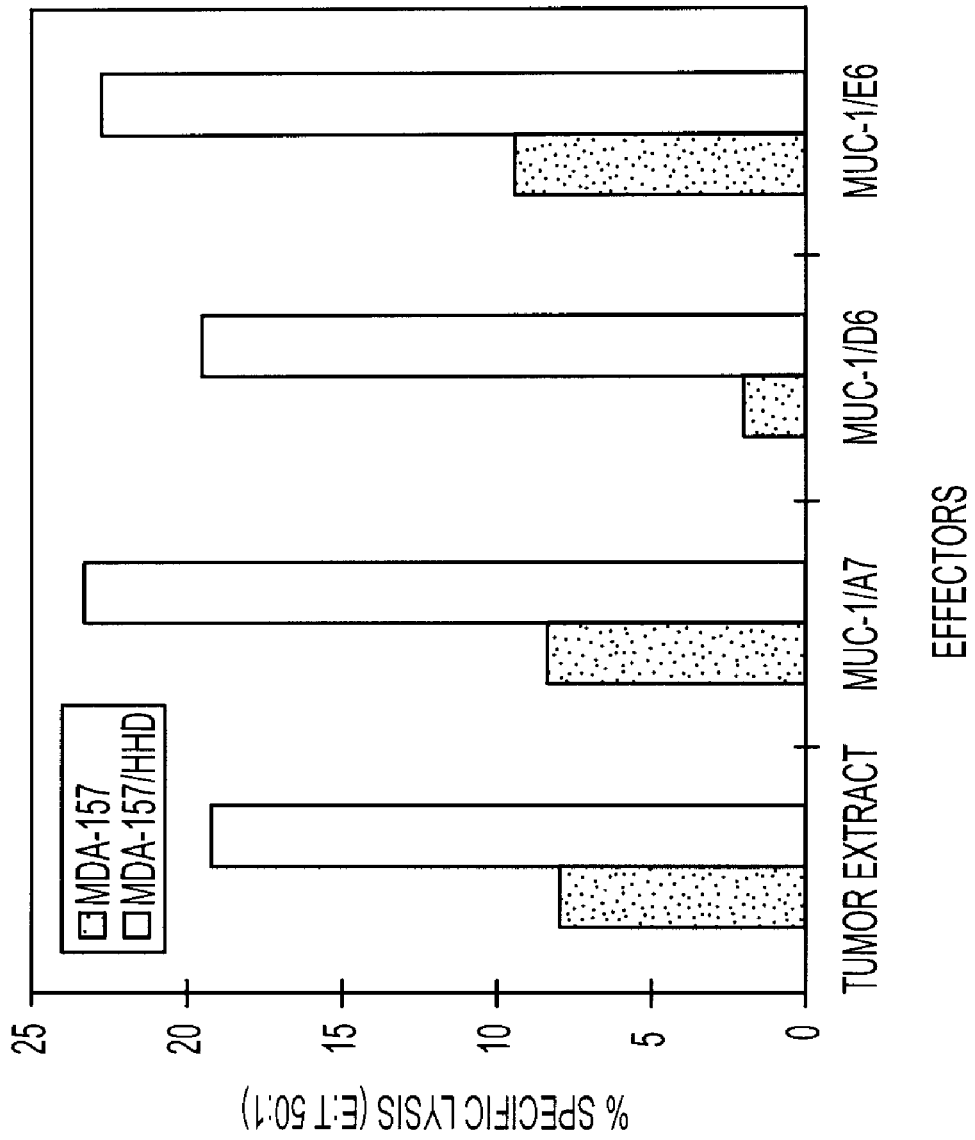
FIG. 20 demonstrates HLA-A2.1 (HhD) restricted lysis of a breast carcinoma cell line by CTL induced against MUC-1 derived peptides. Details as described in FIG. 17.

To determine the processing and presentation of MUC-1-derived peptides by breast carcinoma tumors, we selected the MDA-MB-157 cell line which is characterized by high MUC-1 expression and low class I expression (data not shown). Both the parental tumor cell line and its HhD transfectant (MDA-MB-157-HhD), were used as targets in CTL assays (FIG. 20). Mice were immunized with either RMA-S-HhD-B7.1 cells loaded with MUC-1 selected peptides MUC-1/D6, MUC-1/A7 and MUC-1/E6, or with peptide extract derived from fresh patients' tumors. Preferential lysis of the MDA-MB-157-HhD cell line by anti MUC-1-derived peptides activated lymphocytes suggested both breast associated as well as MHC-restricted lysis. Moreover, this data strongly support the processing and presentation of non TRA associated MUC-1-derive peptides in MDA-MB-157-HhD breast carcinomas cells. Further analysis showed inhibition of lysis by anti HLA monoclonal antibody w6/32 (data not shown). In addition specific lysis of MDA-MB-157-HhD cells by CTL directed against fresh tumor extracted peptides emphasized an overlap in the peptide repertoire between the breast tumor cell line and fresh breast tumor extract.

Figure 21:
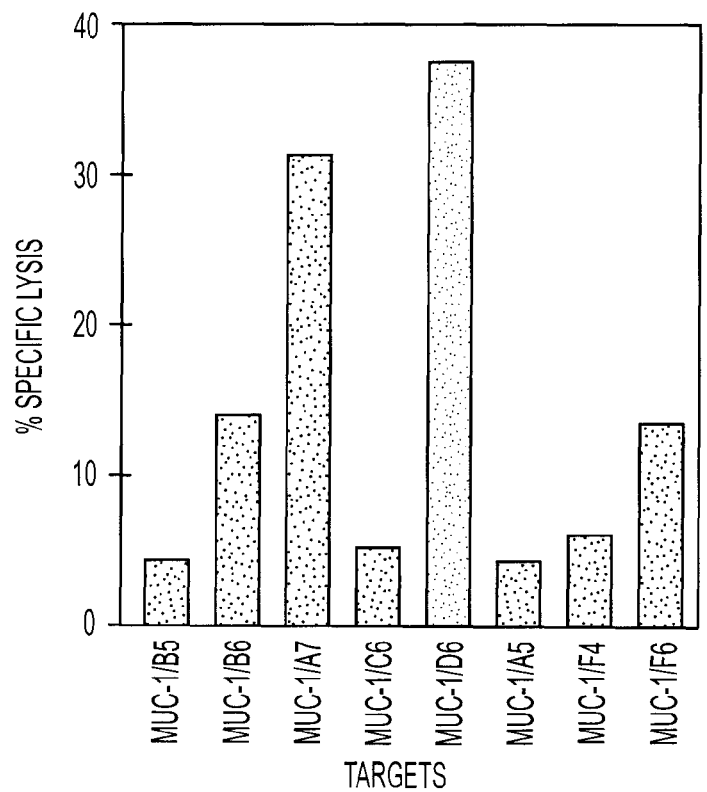
FIG. 21 demonstrates lysis of MUC-1 loaded target cells by CTL induced against breast carcinoma extracted peptides in HhD mice. Details are as described in FIG. 15. E:T is 50:1.

To prove the existence of MUC-1/D6, MUC-1/A7 and MUC-1/E6 peptides in patients' derived breast tumor peptide extracts, a CTL experiment was performed by utilizing CTL against breast tumor peptide extracts as effectors against target cells presenting MUC-1 peptides or a control of normal breast tissue (FIG. 21). All 3 MUC-1-derived peptides, but not the HLA-A2.1 melanoma associated peptide tyrosinase, could be recognized and lysed by anti-tumor extract CTL. RMA-S-HhD cells loaded with normal breast extract gave in different experiment between 40-50% of the lysis induced against tumor extract loaded targets. This result is expected since a part of the tumor extract peptide repertoire consists of normal peptides.

Figure 22:
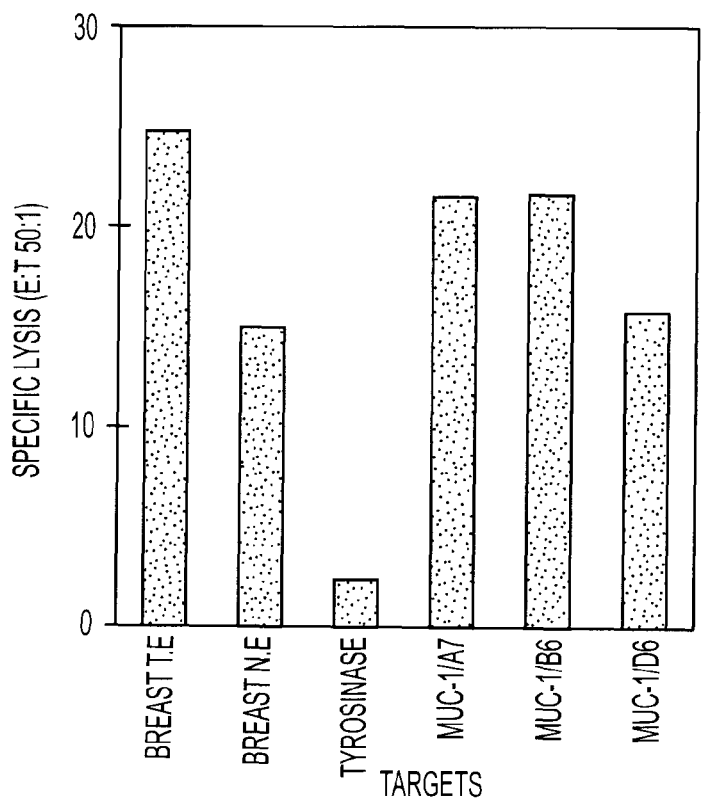
FIG. 22 demonstrates differential lysis of tumor extracted peptide loaded target cells by CTL induced against MUC-1 derived peptides in HhD mice. Details are as described in FIG. 16.
Figure 23A:
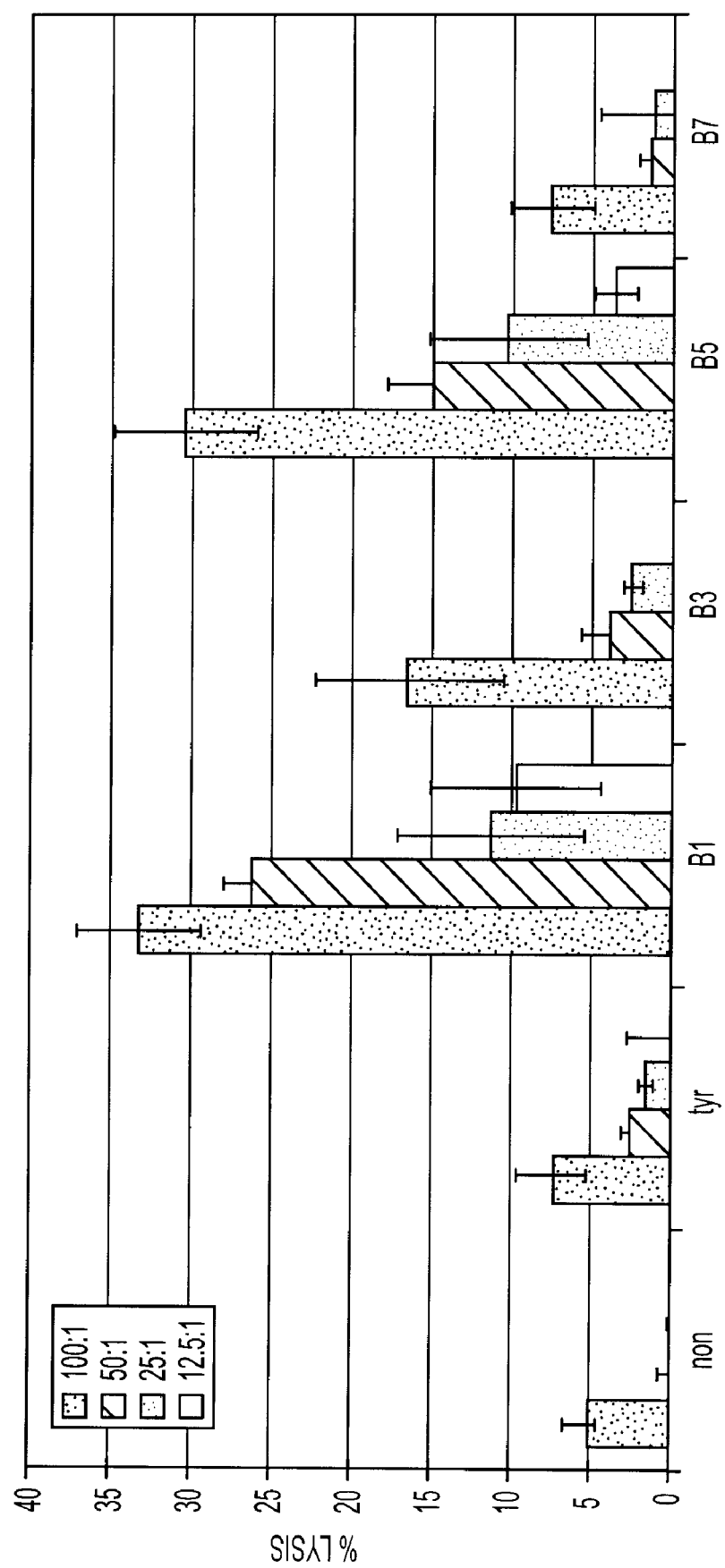
FIGS. 23a-e demonstrate lysis of additional human Uroplakin (Ib, II and III) peptide loaded target cells by CTL induced against the peptides in HhD mice. Mice were immunized with RMA-S-HhD-B7.1 cells, loaded with Uroplakin derived synthetic peptides, as described in Materials and Methods. Loading was performed with individual peptides and cells were pooled for immunization. Resensitized CTL (see Materials and Methods) were tested for lysis of RMA-S-HhD targets loaded with Uroplakin peptides or with an irrelevant HLA-A2 binding peptide derived from tyrosinase. Results are expressed as % Lysis using E:T ratios of 100:1, 50:1, 25:1, and 12.5:1.
Figure 23B:
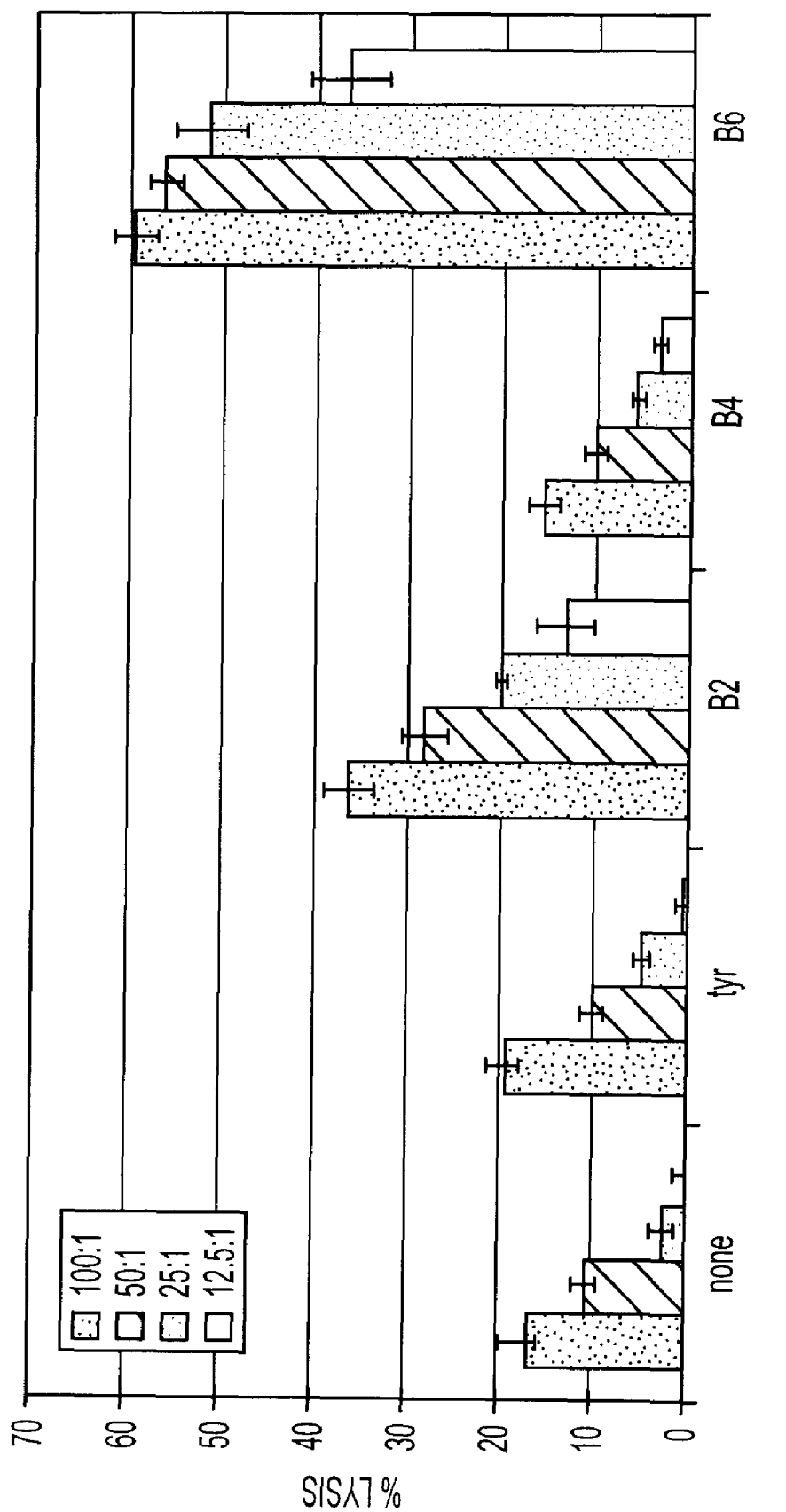
Figure 23C:
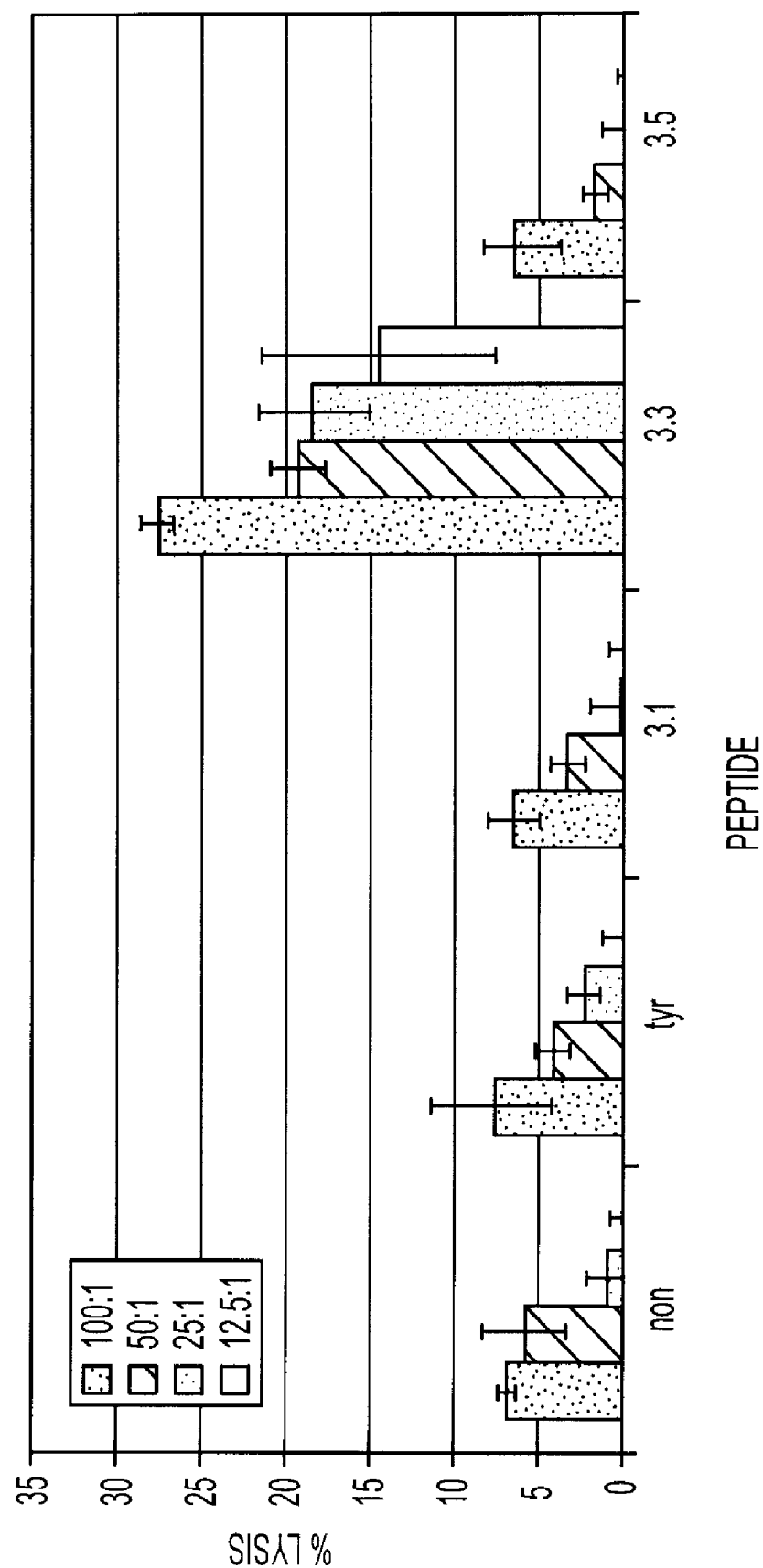
Figure 23D:
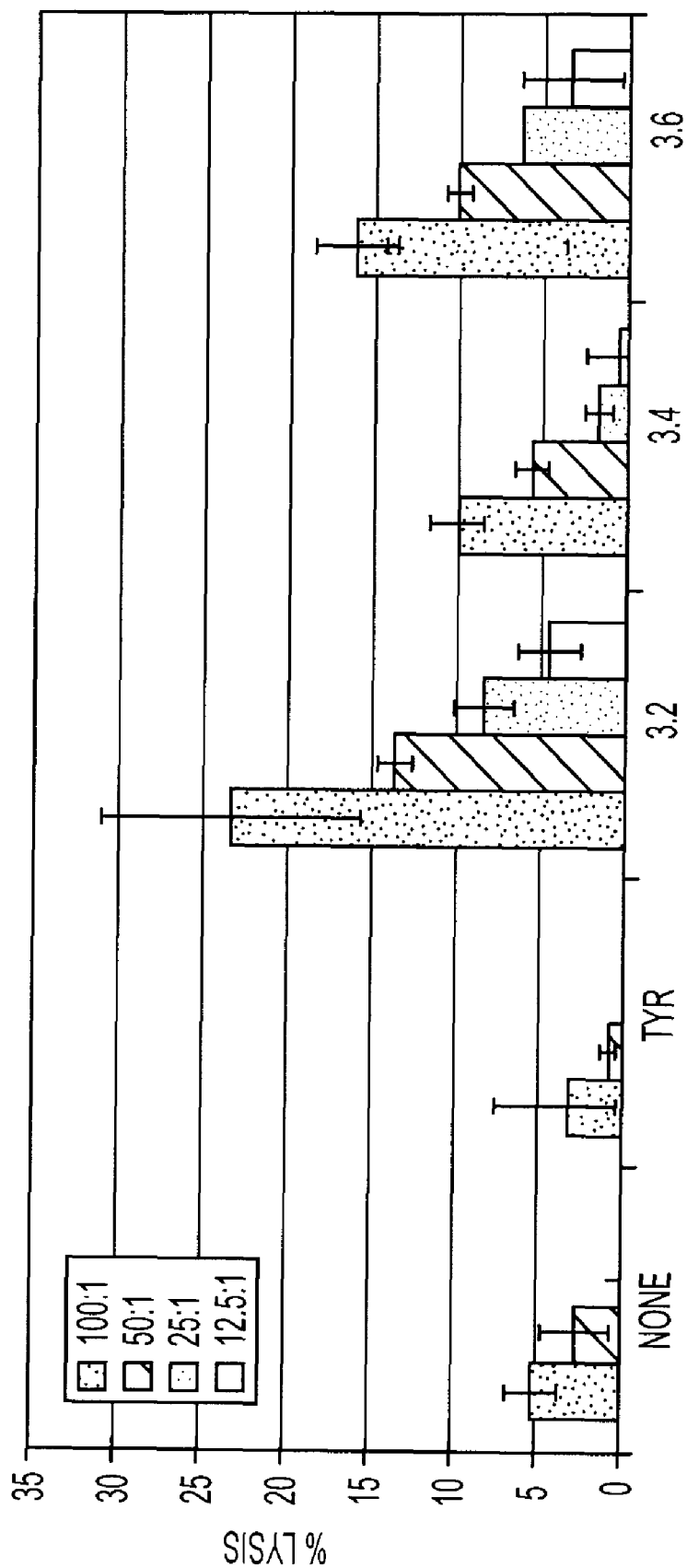
Figure 23E:
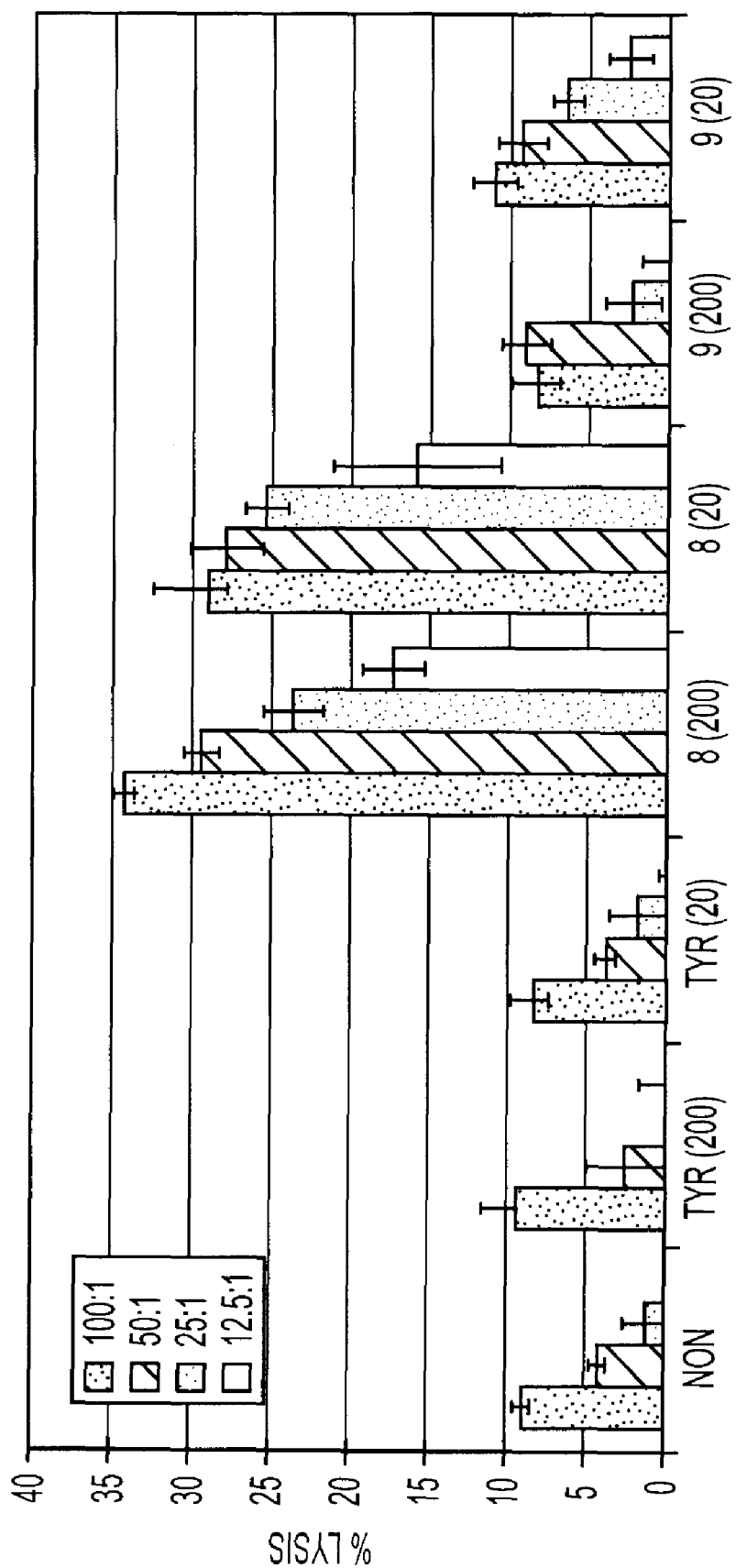

A crucial parameter for selection of TAA peptides based vaccines are their expression frequency by tumors in comparison with normal tissues. Since MUC-1 protein is known to be overexpressed in tumors, with no tumor specific mutations, it is of obvious interest to examine the abundance of MUC-1 peptides in patients' derived normal breast tissue extract in comparison to tumor extract. CTL generated against MUC-1 peptides MUC-1/D6, MUC-1/A7 and MUC-1/E6, showed a 1.8-9.0 fold higher reactivity to tumor extract versus normal tissue extract (FIG. 22). The same difference in preferential tumor versus normal tissue recognition by CTL could be detected upon vaccination with breast tumor extract peptides, supporting the window of specificity between normal and tumor tissues. These results suggest that MUC-1/D6, MUC-1/A7 and MUC-1/E6 are potential tumor associated antigen peptides.

Example 5

Figure 24A:
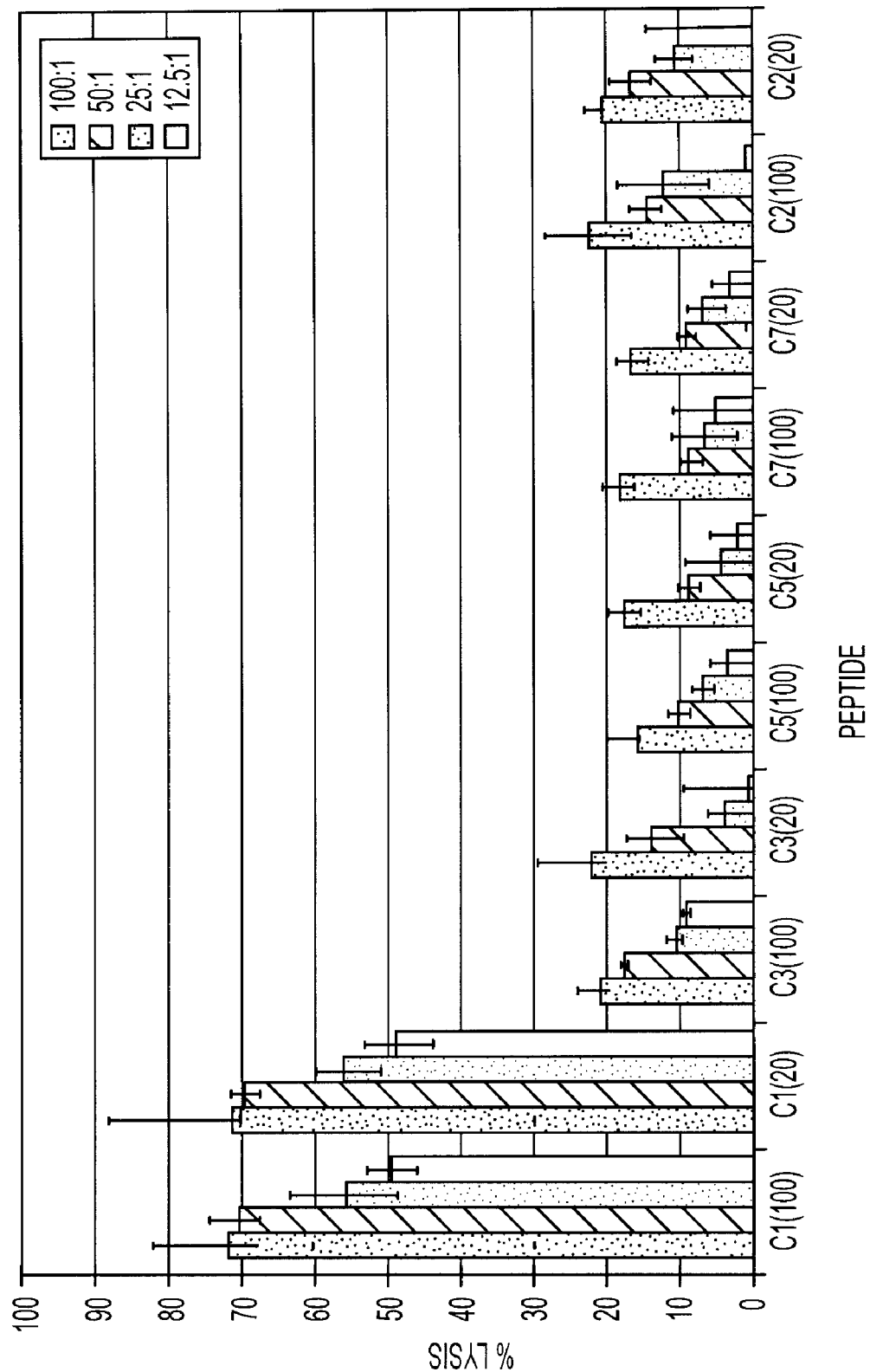
FIG. 24a-c demonstrate lysis of human CRIPTO-a peptide loaded target cells by CTL induced against peptides in HhD mice. Mice were immunized with RMA-S-HhD-B7.1 cells, loaded with CRIPTO-1 derived synthetic peptides, as described in Materials and Methods. Loading was performed with individual peptides and cells were pooled for immunization (pool of C1, C3, C5, and C7 for FIG. 24, pool of C2, C4, C6, and C8 for FIG. 24b, and pool of C10-12 for FIG. 24c). Resensitized CTL were tested for lysis of RMA-S-HhD targets loaded with CRIPTO-1 peptides at two concentrations (200 or 20 µM), or with an irrelevant HLA-A2 binding peptide (C2 for FIG. 24a, C10 for FIG. 24b). Results are expressed a % Lysis using E:T ratios of 100:1, 50:1, 25:1, and 12.5:1.
Figure 24B:
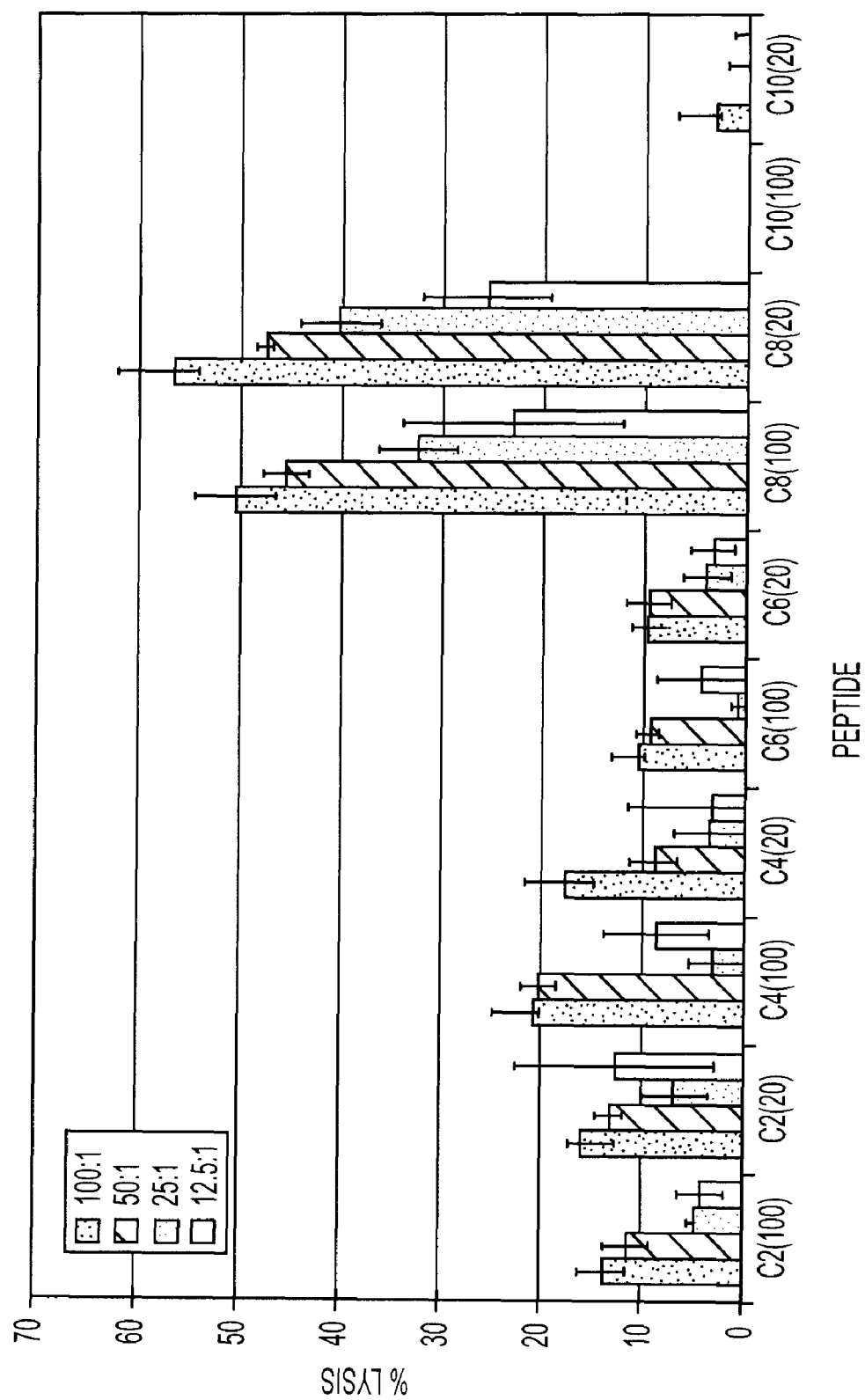
Figure 24C:
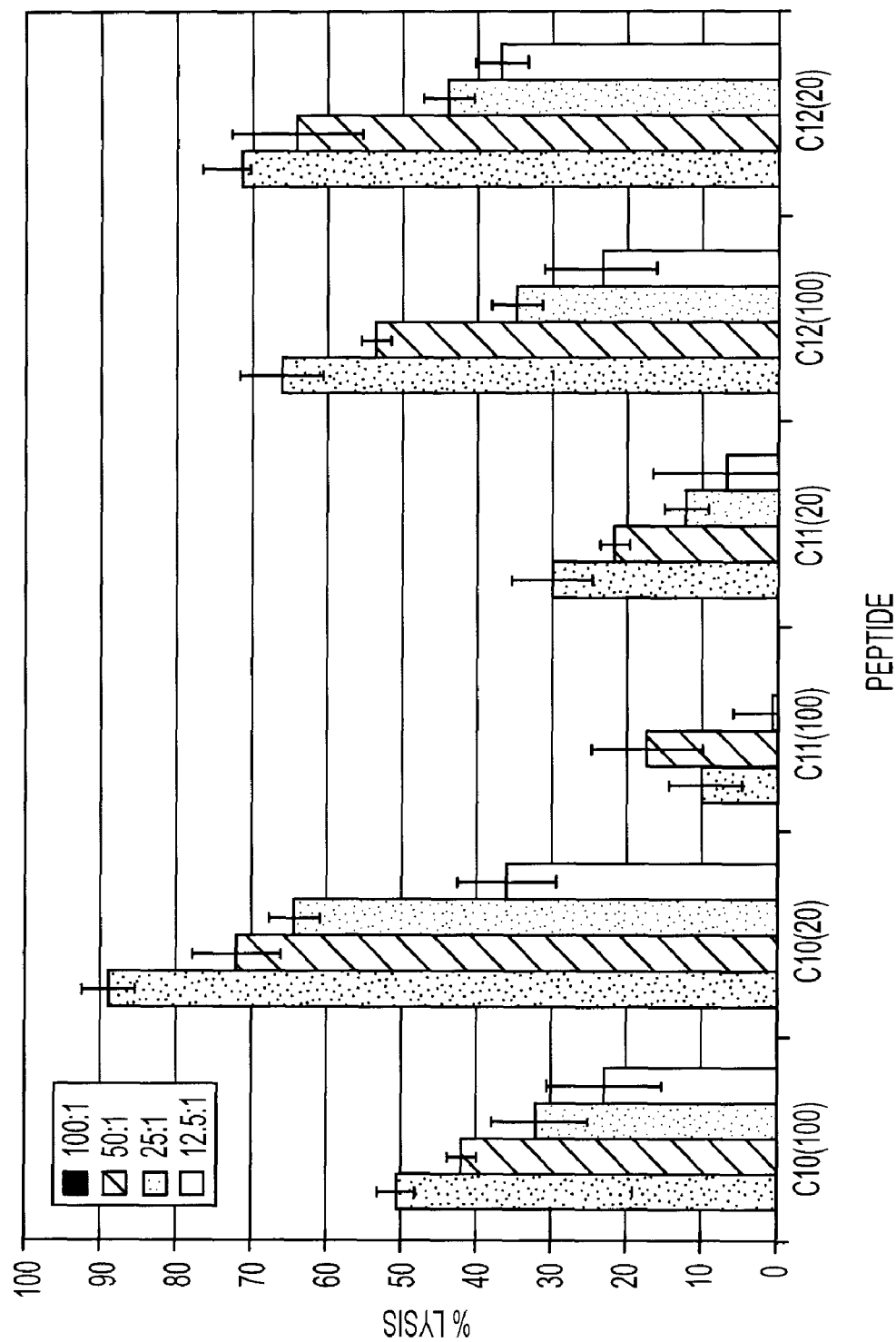

Induction of CTL Response by Teratocarcinoma-Derived Growth Factor (CRIPTO-1) Derived Peptides The CRIPTO-1 gene (also known as Teratocarcinoma-derived growth factor) was first identified and cloned from an undifferentiated human embryonal carcinoma cell line (83). It encodes a 188 amino acid glycoprotein with a region of structural homology to members of the epidermal growth factor family, but lacks a hydrophobic signal peptide and transmembrane domain. The receptor for CRIPTO-1 has not been identified, yet it has been shown to function as a growth factor. The gene can act as a dominantly transforming oncogene in vitro. A number of studies have shown elevated expression of CRIPTO-1 mRNA and protein in several human cancers, including human primary breast, gastric, colon, pancreatic, and bladder (84-88). It is therefore an attractive candidate tumor associated antigen for specific, active immunotherapy. Peptides have been synthesized with HLA-A2.01 binding potential based on the published sequences of CRIPTO-1, and these peptides have been used for immunization of HhD transgenic mice (see Table 9). FIGS. 24a-c show that some of the tested peptides (C1, C8, C10, and C12) can elicit lymphocyte response which specifically lyses CRIPTO-1 peptide-loaded target cells.

TABLE 9

Predicted human Cripto-1 derived peptides that bind to HLA-A2

| Peptide | Start Position | Sequence | SEQ ID NO: |
|---|---|---|---|
| Cripto-1/C1 | 5 | KMARFSYSV | 66 |
| Cripto-1/C2 | 151 | GLVMDEHLV | 67 |
| Cripto-1/C3 | 145 | FLPGCDGLV | 68 |
| Cripto-1/C4 | 89 | CMLGSFCAC | 69 |
| Cripto-1/C5 | 43 | YLAFRDDSI | 70 |
| Cripto-1/C6 | 123 | WLPKKCSLC | 71 |
| Cripto-1/C7 | 83 | CLNGGTCML | 72 |
| Cripto-1/C8 | 176 | MLVGICLSI | 73 |
| Cripto-1/C9 | 23 | FELGLVAGL | 74 |
| Cripto-1/C10 | 5 | KMVRFSYSV | 75 |
| Cripto-1/C11 | 83 | CLNEGTCML | 76 |
| Cripto-1/C12 | 176 | MLAGICLSI | 77 |

Table 9 shows the sequences of the peptides tested in single letter amino acid code and their starting position in the intact protein (according to NCBI accession nos. 117473 (C1-C9) and 321120 (C10-C12).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES CITED

1. Fidler, I. J. and Balch, C. M. (1987) The biology of cancer metastasis and implications for therapy. Curr. Progr. Surg. 24, 137-209. Boring, C. C., Squires, T. S., Tong, T., Montgomery, S.,
2. Abeloff, M. D. (1996) Breast Cancer. Current opinion in oncology 8, 447-448.
3. Andriole, G. L. (1997) Adjuvant therapy for prostate cancer patients at high risk of recurrence following radical prostatectomy. Eur. Urol. Supp 3; 65-69.
4. Nseyo, U. O. and Lamm, D. L. (1997) Immunotherapy of bladder cancer. Semin. Surg. Oncol. 13, 342-349.
5. Kedar, E. and Klein, E. (1995) Cancer Immunotherapy: Are the results discouraging? Can they be improved? Adv. Immunol. 58, 245-322.
6. Urban, J. L. and Schreiber, H. (1992) Tumor antigens. Annu. Rev. Immunol. 10, 617-644.
7. Van Pel, A. and Boon, T. (1982) Protection against a non-immunogenic mouse leukemia by an immunogenic variant obtained by mutagenesis. Proc. Natl. Acad. Sci. USA 79, 4718-4722.
8. Pardoll, D. M. (1993) New strategies for enhancing the immunogenicity of tumors. Curr. Opinion Immunol. 5, 719-725.
9. Qin, Z. and Blankenstein, T. (1996) Influence of local cytokines on tumor metastasis: using cytokine gene transfected tumor cells as experimental models. In "Attempts to Understand Metastasis Formation III", Therapeutic Approaches for Metastasis Treatment, Current Topics in Microbiology and Immunology (U. Gunlhert, P. M. Schlag and W. Birchmeier, eds.) 213III, 55-64.
10. Pardoll, D. M. (1996) Cancer vaccines: a road map for the next decade. Curr. Opinion Immunol. 8, 619-621.
11. Boon, T. and van der Bruggen, P. (1996) Human tumor antigens recognized by T lymphocytes. J. Exptl. Med. 183, 725-729.
12. Townsend, A. and Bodmer, H. (1989) Antigen recognition by class I-restricted T lymphocytes. Annu. Rev. Immunol. 7, 601-624.
13. Rammensee, H.-G., Falk, K. and Rotzschke, O. (1993) Peptides naturally presented by MHC class I molecules. Annu. Rev. Immunol. 11, 213-244.
14. Feltkamp, M., Smits, H. L., Vierboom, M., Minnaar, R. P., dejough, B. M., Drijfhout, J. W., Schegget, J., Melief, C. J. M. and Kast, W. M. (1993) Vaccination with cytotoxic T lymphocyte epitope-containing peptide protects against a tumor induced by human papillomavirus type 16-transformed cells. Eur. J. Immunol. 23, 2242-2249.
15. Kast, W. M., Brandt, R. M. P., Sidney, J., Drijfhout, J. W., Kubo, R. T., Melief, C. J. M. and Sette, A. (1994) Role of HLA-A motifs in identification of potential CTL epitopes in human papillomavirus type 16 E6 and E7 proteins. J. Immunol. 152, 3904-3912.
16. Mandelboim, O., Berke, G., Fridkin, M., Feldman, M., Eisenstein, M. and Eisenbach, L. (1994) CTL induction by a tumor-associated antigen octapeptide derived from a murine lung carcinoma. Nature (Lond.) 369, 67-71.
17. Cox, A., Skipper, J., Chen, Y., Henderson, R., Darrow, T., Shabanowitz, J., Engelhard, V., Hunt, D. and Slingluff, C. (1994) Identification of a peptide recognized by five melanoma-specific human cytotoxic T cell lines. Science 264, 716-719.
18. Blake, J., Johnston, J., Hellstrom, K. E., Marquardt, H. and Chen, L. (1996) Use of combinatorial peptide libraries to construct functional mimics of tumor epitopes recognized by MHC class I restricted T lymhocytes. J. exp. Med. 184, 121-130.
19. Boon, T., Cerottini, J.-C., Van den Eynde, B., Van der Bruggen, P. and Van Pel, A. (1994) Tumor antigens recognized by T lymphocytes. Annu. Rev. Immunol. 12, 337-365.
20. Marchand, M., Weynants, P., Rankin, E., Arienti, F., Belli, F., Parmiani, G., Cascinelli, N., Bourland, A., Wanwijck, R., Humblet, Y., Canon, J. L., Naeyaert, J. M., Plagne, R., Deraemaeker, R., Knuth, A., Jager, E., Brasseur, F., Herman, J., Coulie, P. G. and Boon, T. (1995) Int. J. Cancer 63, 883-885.
21. Rosenberg, S. A. et al. (1998) Immunologic and therapeutic evaluation of a synthetic peptide vaccine for the treatment of patients with metastatic melanoma. Nature Med. 4, 321-327.
22. Nestlel, F. L., Alijagic, S., Gillietl, M., Sun, Y., Grabbe, S., Dummerl, R., Burge, G. and Schadendorf, D. (1998) Vaccination of melanoma patients with peptide or tumor lysate-pulsed dendritic cells. Nature Med. 4, 328-332.
23. Mandelboim, O., Vadai, E., Fridkin, M., Katz-Hillel, A., Feldman, M., Berke, G. and Eisenbach, L. (1995) Regression of established murine carcinoma metastases following vaccination with tumor-associated antigen. Nature Med. 1, 1179-1183.
24. Mayordomo, J. I., Zorina, T., Storkus, W. J., Zitvogel, L., Cellzzi, C, Falo, L. D., Melief, C. J., Ildstadst, W. M., Deleo, A. B. (1995. Bone marrow derived dendritic cells pulsed with synthetic tumor peptides elicit protective and therapeutic anti tumor immunity. Nature Medicine 1, 1297-1302.
25. Fearon, E. R., Pardoll, D. M., Itaya, T., Golumbek, P., Levitsky, H. I., Simons, J. W., Karasuyama, H., Vogelstein, B., and Frost, P. (1990) Interleukin-2 production by tumor cells by passes T helper function in generation of an anti-tumor response. Cell 60, 397-403.
26. Bakker, A., Schreurs, M., deBoer, A., Kawakami, Y., Rosenberg, S., Adema, G. and Figdor, C. (1994) Melanocyte lineage-specific antigen gp100 is recognized by melanoma-derived tumor-infiltrating lymphocytes. J. Exp. Med. 179, 1005-1009.
27. Wentworth, P. A., Vitiello, A., Sidney, J., Keogh, E., Chesnut, R. W., Grey, H. and Sette, A. (1996) Differences and similarities in the A2.1-restricted cytotoxic T cell repertoire in humans and human leukocyte antigen-transgenic mice. Eur. J. Immunol. 26, 97-101.
28. Barra, C., Gournier, H., Garcia, Z., Marche, P. N., Jouvin-Marche, E., Briand, P., Fillipi, P. and Lemonnier, F. A. (1993) Abrogation of H-2-restricted CTL responses and efficient recognition of HLA-A3 molecules in DBA/2 HLA/A24 responder mice. J. Immunol. 150, 3681-3689.
29. Vitiello, A., Marchesini, D., Furze, J., Sherman, L. A., Chestnut, R. W. (1991) Analysis of HLA restricted influenza specific cytotoxic T lymphocytes response in transgenic mice carrying a chimeric human-mouse class I major histocompatibility complex. J. Exp. Med. 173, 1007-1015.
30. Pascolo, S., Bervas, N., Ure, J. M., Smith, A. G., Lemmonier, F. A. and Rerarnau, B. (HLA-A2.1 restricted education and cytolytic activity of CD8$^+$ T lymphocytes from β2 microglobulin (β$_2$m) HLA-A2.1 monochain transgenic, H-2 D$^b$, β$_2$m double knockout mice. J. Exp. Med. 185, 2043-2051.

31. Spooner, R. A., Deonarain, M. P. and Epenetos, A. A., DNA vaccination for cancer treatment. Gene Therapy 2, 173-180, 1995.

32. Ulmer, J. B., Donnelly, J. J., Parker, S. E., Rhodes, G. H., Felgner, P. L., Dwaraki, V. J., Gromkowski, S. H., Deck, R. R., DeWitt, C. M., Friedman, A., Hawe, L. A., Leander, K. R., Martinez, D., Perry, H. C., Shiver, J. W., Montgomery, D. L. and Liu, M. A., Heterologous protection against influenza by injection of DNA encoding a viral protein. Science 259, 1745-1749, 1993.

33. Conry, R. M., LoBuglio, A. F., Kantor, J., Schlom, J., Loechel, F., Moore, S. E., Sumerel, L. A., Barlow, D. L., Abrams, S. and Curiel, D. T., Immune response to a carcinoembryonic antigen polynucleotide vaccine. Canceer Res., 54, 1164-1168, 1994.

34. Conry, R. M., LoBuglio, A. F., Loechel, F., Moore, S. E., Sumerel, L. A., Barlow, D. L., Pike, J. and Curiel, D. T. A carcinoembryonic antigen polynucleotide vaccine for human clinical use. Cancer Gene Therapy 2, 33-38, 1995.

35. Acres, R. B., Hareuveni, M., Balloul, J.-M. and Kieny, M.-P. Vaccinia virus MUC1 immunization of mice: immune response and protection against the growth of murine tumors bearing the MUC1 antigen. J. Immunother. 14, 136-143, 1993.

36. Whitton, J. L., Sheng, N., Oldstone, M. B. and McKee, T. A., A "string-of-beads" vaccine, comprising linked minigenes, confers protection from lethal-dose virus challenge. J. Virol. 67, 348-352, 1993.

37. Thomson, S. A., Elliott, S. L., Sherritt, M. A., Sproat, K. W., Coupar, B. E., Scalzo, A. A., Forbes, C. A., Ladhams, A. M., Mo, X. Y., Tripp, R. A., Doherty, P. C., Moss, D. J. and Suhrbier, A., Recombinant polyepitope vaccines for the delivery of multiple CD8 cytotoxic T cell epitopes. J. Immunol. 157, 822-826, 1996.

38. Thomson, S. A., Sherritt, M. A., Medveczky, J., Elliott, S. L., Moss, D. J., Fernando, G. J., Brown, L. E., and Suhrbier, A., Delivery of multiple CD8 cytotoxic T cell epitopes by DNA vaccination. J. Immunol. 160, 1717-1723, 1998.

39. Boczkowski, D., Nair, S. K., Snyder, D. and Gilboa, E., Dendritic cells pulsed with RNA are potent antigen-presenting cells in vitro and in vivo. J. Exp. Med. 184, 465-472, 1996.

40. Mayordomo, J. I., Zorina, T., Storkus, W. J., Zitvogel, L., Celluzzi, C., Falo, L. D., Melief, C. J., Ildstad, S. T., Kast, W. M., Deleo, A. B., et al., Bone marrow-derived dendritic cells pulsed with synthetic tumor peptides elicit protective and therapeutic antitumor immunity. Nature Med. 1, 1297-1302, 1995.

41. Mandelboim, O., Berke, G., Fridkin, M., Feldman, M., Eisenstein, M., and Eisenbach, L., CTL induction by a tumor-associated antigen octapeptide derived from a murine lung carcinoma. Nature 369, 67-71, 1994.

42. Mandelboim, O., Vadai, E., Fridkin, M., Katz-Hillel, A., Feldman, M., Berke, G., and Eisenbach, L., Regression of established murine carcinoma metastases following vaccination with tumour-associated antigen peptides. Nat. Med. 1, 1179-1183, 1995.

43. Mukherji, B., Chakraborty, N. G., Yamasaki, S., Okino, T., Yamase, H., Sporn, J. R., Kurtzman, S. K., Ergin, M. T., Ozols, J., Meehan, J., et al., Induction of antigen-specific cytolytic T cells in situ in human melanoma by immunization with synthetic peptide-pulsed autologous antigen pre senting cells. Proc. Natl. Acad. Sci. USA 92, 8078-8082, 1995.

44. Gjertsen, M. K., Bakka, A., Breivik, J., Saeterdal, I., Gedde-Dahl, Stokke, K. T., Solheim, B. G., Egge, T. S., Soreide, O., Thorsby, E., and Gaudernack, G., Ex vivo ras peptide vaccination in patients with advanced pancreatic cancer: results of a phase I/II study. Int. J. Cancer 65, 450-453, 1996.

45. Murphy, G., Tjoa, B., Ragde, H., Kenny, G. and Boynton, A., Phase I clinical trial: T-cell therapy for prostate cancer using autologous dendritic cells pulsed with HLA-A0201-specific peptide from prostate-specific membrane antigen. Prostate 29, 371-380, 1996.

46. Messing, E. M. and Catalona, W. Urothelial tumors of the urinary tract. In Campbell's Urology, Eds. Walsh, P. C., Retik, A. B., Vaugham, E. D. and Wein, A. J. (7th edition, WB, Sounders Co. 1998), 2327-2410.

47. Ioachim-Velogianni, E., Stavropoulos, N. E., Kitsiou, E., Stefanaki, S, and Agnantis, N. J. (1995) Distribution of CD1A-positive Langerhans cells and lymphocytes subsets in transitional cell carcinoma of the urinary bladder. An immunohistological study on frozen sections. J. Pathol. 155, 401-406.

48. Thanhauser, A., Bohle, A., Flad, H. D., Ernst, M., Mattern, T. and Ulmer, A. J. (1993) Induction of bacillus Calmette-Gherin activated killer cells from human peripheral blood mononuclear cells against bladder carcinoma cell lines in vitro. Cancer Immunol. Immunother. 37, 105-111.

49. Patard, H., Muscatelli-Groux, B., Saint, F., Popov, Z., Maille, P., Abbou, C. and Chopin, D. (1996) Evaluation of local immune response after intravesical bacille Calmette Guerin treatment for superficial bladder cancer. Br. J. Urol. 78, 709-714.

50. Housseau, F., Zeliskewski, D., Roy, M. et al. (1997) MHC-dependent cytolysis of autologous tumor cells by lymphocytes infiltrating urothelial carcinomas. Int. J. Cancer 71, 585-594.

51. Moll, R., Wu, X-R., Lin, J-H. and Sun, T-T. (1995) Uroplakins, specific membrane proteins of urothelial umbrella cells, as histological markers of metastatic transitional cell carcinomas. Am. J. Pathol. 147, 1383-1397.

52. Mandelboim, O., Bar-Haim, E., Vadai, E., Fridkin, M. and Eisenbach, L. (1997) Identification of shared Tumor-Associated Antigen peptides between two spontaneous lung carcinomas. J. Immunol. 159, 6030-6036.

53. Boring, C. C., Squires, T. S., Tong, T. and Montgomery, S. (1994) Cancer statistics 1994 CA 43, 7-26.

54. Carter, H. B., Pearson, J. D., Metter, J. E. et al. (1992) Longitudinal evaluation of prostate specific antigen levels in men with and without prostate disease. JAMA 267, 2215-2220.

55. Partin, A. W., Poind, C. R., Clemens, J. Q. et al. (1993) Serum PSA after anatomic radical prostatectomy. Urol. Clin. North Am. 20, 713-725.

56. Epstein, J. I., Partin, A. W., Sauvageot, J. and Walsh, P. C. (1996) Prediction of progression following radical prostatectomy. A multivariate analysis of 721 men with long term follow up. Am. J. Surg. Pathol. 20, 286-292.

57. Eisenberger, M. H. (1998) Chemotherapy for hormone resistant prostate cancer. In Campbell's Urology, Eds. Walsh, P. C., Retik, A. B., Vaugham, E. D. and Wein, A. J. (7th edition, WB, Sounders Co.) 2645-2658.

58. Schroder, F. H. (1998) Endocrine treatment of prostate cancer. In Campbell's Urology, Eds. Walsh, P. C., Retik, A.

B., Vaugham, E. D. and Wein, A. J. (7th edition, WB, Sounders Co.) 2627-2644.

59. Xue, B. H., Zhang, Y., Sosman, J. A. and Peace, D. J. (1997) Induction of human cytotoxic T lymphocytes specific for prostate specific antigen. The Prostate 30, 73-78.

60. Correale, P., Walmsley, K., Nieroda, C., Zhu, M., Schlom, J. and Tsang, K. Y. (1997) In vitro generation of human cytotoxic T lymphocytes specific for peptides derived from prostate specific antigen. J. Natl. Cancer Inst. 89, 272-275.

61. Tjoa, B., Bounton, A., Kenny, G., Ragde, H., Misrock, S. L. and Murphy, G. (1996) Presentation of prostate tumor antigens by dendritic cells stimulates T cell proliferation and cytotoxicity. Prostate 28, 65-69.

62. Murphy, G., Tjoa, B., Ragde, H., Kenny, G. and Bounton, A. (1996) Phase I clinical trial: T cell therapy for prostate cancer using autologous dendritic cells pulsed with HLA-A0201 specific peptides from Prostate Specific Membrane Antigen. The Prostate 29, 371-380.

63. Bonandona, G. (1996) Future development in adjuvant systemic therapy for high risk breast cancer. Cancer Res. 140, 227-234.

64. Barnd, D. L., Lan, M., Metzger, R., Finn, O. J. (1989. Specific, MHC-unrestrieted recognition of tumor associated mucins by human cytotoxic T cells. Proc. Natl. Acad. SCI. USA 86, 7159-7163.

65. Agrawal, B., Reddish, M., Longenecker, B. M. (1996). Invitro induction of MUC-1 peptide specific type 1 T lymphocyte and cytotoxic T lymphocyte responses from healthy multiparous donors. J. Immunol. 157, 2089-2095.

66. Fisk, B., Blevins, T. L., Taylor-Wharton, J., Ionnides, C. G., (1995). Identification of an immunodominant peptide of HER2/neu protooncogene recognized by ovarian Tumor specific cytotoxic T lymphocyte lines. J. Exp. Med. 181, 2109-2117.

67. Linehan, C., Goedegebuure, P. S., peoples, G. E., Rogers, S. O., Eberlein, P. J. (1995) Tumor specific and HLA-A2 restricted cytolysis by tumor-associated lymphocytes in human metastatic breast cancer. J. Immunol 155, 4486-4491.

68. Larocca, D., Peterson, J. A., Urrea, R., Kuniyoshi, J., Bistrain, A. M. and Ceriani, R. L. (1991) A Mr 46,000 human milk fat globule protein that is highly expressed in human breast tumors contains factor VIII-like domains. Cancer Res. 15, 4994-4998.

69. Taylor, M. R., Couto, J. R., Scallan, C. D., Ceriani, R. L. and Peterson, J.A. (1997) Lactadherin (formerly BA-46), a membrane-associated glycoprotein expressed in human milk and breast carcinomas, promotes Arg-Gly-Asp (RGD)-dependent cell adhesion. DNA Cell Biol. 16, 861-869.

70. Ceriani, R. L., Blank, E. W., Couto, J. R., and Peterson, J. A. (1995) Biological activity of two humanized antibodies against two different breast cancer antigens and comparison to their original murine forms. Cancer Res. 155, 5852-S5856S.

71. Couto, J. R., Blank, E. W., Peterson, J. A., Ceriani, and R. L. (1995) Anti-BA-46 monoclonal antibody Mc3: humanization using a novel positional consensus and in vivo and in vitro characterization. Cancer Res. 55, 1717-1722.

72. Ho, S. B., Niehans, G. A., Lyftogt, C., Yan, P. S., Cherwitz, D. L., Gum, E. T., Dahiya, R., and Kim, Y. S. (1993) Heterogeniety of Mucin gene expression in normal and neoplastic tissues. Cancer Res 1, 641-651

73. Spicer, A. P., Rowse, G. J., Linder, T. K. and Gendler, S. J. (1995) Delayed mammary tumor progression in Muc-1 null mice. J. Bio. Chem. 270, 30093.

74. McGuckin, M. A., Walsh, M. D., Hohn, B. G., Ward, B. G. and Wright, R. G. (1995) Prognostic significance of Muc-1 epithelial Mucin expression in breast cancer. Hum. Pathol. 26, 432.

75. Wreschner, D. H., Hareuveni, M., Tsarfaty, I., Smorodinsky, N., Horev, J., Zaretsky, J., Kotkes, P., Weiss, M., Lathe, R. and Dion, A. (1990) Human epithelial tumor antigen sequences. Differential splicing may generate multiple protein forms. Eur. J. Biochem. 189, 463.

76. Domenech, N. and Finn, O. J. (1995) In vitro studies of MHC-restricted recognition of a peptide from the MUC1 tandem repeat domain by CTL. FASEB J. 9, 1023.

77. Domenech, N., Henderson, R. A. and Finn, O. J. (1995) Identification of a HLA-A11-restricted epitope from the tandem repeat domain of the epithelial tumor antigen Mucin. J Immunol 15, 4766.

78. Apostolopoulos, V., Karanikas, V., Haurum, J. S, and McKenzie, I. F. (1997) Induction of HLA-A2-restricted CTLs to the Mucin 1 human breast cancer antigen. J. Immunol. 159, 5211.

79. Mackenzi, P. Y. and Longenecker, B. M. (1991) Specific immunosuppressive activity of epiglycanin, a Mucin-like glycoprotein secreted by a murine mammary adenocarcinoma (TA3-HA). Cancer Res. 15, 1170.

80. Gimmi, C. D., Morrison, B. W., Mainpric, B. A., Gribben, J. G., Boussiotis, V. A., Freeman, G. J., Park, S. Y., Watanabe, M., Gong, J., Hayes, D. F., Kufe, D. W. and Nadler, L. M. (1996) Breast cancer-associated antigen, DF3/MUC1, induces apoptosis of activated human T cells. Nat. Med. Dec. 2, 1367.

81. Agrawal, B., Krantz, M. J., Reddish, M A., Longenecker and B. M. (1998) Cancer-associated MUC1 Mucin inhibits human T-cell proliferation, which is reversible by IL-2. Nat. Med. 4, 43.

82. Parker, K. C., Bednarek, M. A., Coligan, J. E., Scheme for ranking potential HLA-A2 binding peptides based on independent binding of individual peptide side-chains. J. Immunol. 152, 163-175, 1994.

83. Ciccodicola, A., Dono, R., Obici, S., Simeone, A., Zollo, M., and Persico, M. G. (1989) Molecular characterization of a gene of the 'EGF family' expressed in undifferentiated human NTERA2 teratocarcinoma cells. EMBO J. 8, 1987.

84. Qi, C. F., Liscia, D. S., Normano, N., Merlo, G., Johnson, G. R., Gullick, W. J., Ciardiello, F., Sacki, T., Brandt, R., Kim, N., Kenney, N., and Salomon, D. S. (1994) Expression of Transforming Growth Factor A, Amphiregulin and Cripto-I in Human Breast Carcinomas. Br J Cancer, 69, 903.

85. Kuniyasu, H., Yoshida, K., Yokoazaki, H., et al. (1991) Expression of Cripto, a Novel Gene of the Epidermal Growth Factor Family, in Human Gastrointestinal Carcinomas. Jpn J Cancer Res 82, 969.

86. Saeki, T., Stromberg, K., Qi, C. F., et al. (1992) Differential Immunohistochemical Detection of Amphiregulin and Cripto in Human Normal Colon and Colorectal Cancers Tumours. Cancer Res. 52, 3467.

87. Freiss, H., Yamanaka, Y., Buchler, M., Korbin, M. S., et al. (1994) Cripto, A Member of The Epidermal Growth Factor Family, is Over Expressed in Human Pancreatic Cancer and Chronic Pancreatitis. Int J Cancer 56, 688.

88. Byrne, R. L., Autzen, P., Birch, P., Robinson, M. C., Gullick, W. J., et al. (1998). The Immunohistochemical Detection of Cripto-1 in Benign and Malignant Human Bladder. J. Pathol. 185, 108.

What is claimed is:

1. An isolated peptide consisting of a peptide selected from the group consisting of SEQ ID NOs:1-19 and 50-64.

2. The isolated peptide according to claim 1, consisting of SEQ ID NO: 1, 3, 8 or 9.

3. The isolated peptide according to claim 1, consisting of SEQ ID NO: 13, 16 or 17.

4. The isolated peptide according to claim 1, consisting of SEQ ID NO: 50, 51, 54, 55, 56, 61 or 64.

5. A pharmaceutical composition comprising, as an active ingredient, at least one isolated peptide as set forth in claim 1 and a pharmaceutically acceptable carrier.

6. The pharmaceutical composition of claim 5, wherein said composition further comprises, as an active ingredient, an antigen presenting cell, said antigen presenting cell presenting a peptide selected from the group consisting of SEQ ID NOs:1-19 and 50-64.

7. A method of treating a cancer or for inhibiting metastases thereof, comprising administering to a patient in need thereof an effective amount of the pharmaceutical composition of claim 5.

8. The method of claim 7, wherein the cancer is transitional cell carcinoma (TCC) of the bladder.

* * * * *

SEQUENCE LISTING

<160> NUMBER OF SEQ ID NOS: 78

<210> SEQ ID NO 1
<211> LENGTH: 9
<212> TYPE: PRT
<213> ORGANISM: Homo sapiens

<400> SEQUENCE: 1

Phe Leu Leu Val Leu Gly Phe Ile Ile
1               5

<210> SEQ ID NO 2
<211> LENGTH: 9
<212> TYPE: PRT
<213> ORGANISM: Homo sapiens

<400> SEQUENCE: 2

Val Leu Pro Ser Val Ala Met Phe Leu
1               5

<210> SEQ ID NO 3
<211> LENGTH: 9
<212> TYPE: PRT
<213> ORGANISM: Homo sapiens

<400> SEQUENCE: 3

Leu Val Leu Gly Phe Ile Ile Ala Leu
1               5

<210> SEQ ID NO 4
<211> LENGTH: 9
<212> TYPE: PRT
<213> ORGANISM: Homo sapiens

<400> SEQUENCE: 4

Lys Val Val Thr Ser Ser Phe Val Val
1               5

<210> SEQ ID NO 5
<211> LENGTH: 9
<212> TYPE: PRT
<213> ORGANISM: Homo sapiens

<400> SEQUENCE: 5

Leu Val Pro Gly Thr Lys Phe Tyr Ile
1               5

<210> SEQ ID NO 6
<211> LENGTH: 9
<212> TYPE: PRT
<213> ORGANISM: Homo sapiens

<400> SEQUENCE: 6

Leu Leu Pro Ile Arg Thr Leu Pro Leu
1               5

<210> SEQ ID NO 7
<211> LENGTH: 9
<212> TYPE: PRT
<213> ORGANISM: Homo sapiens

<400> SEQUENCE: 7

Tyr Leu Val Lys Lys Gly Thr Ala Thr

```
1               5

<210> SEQ ID NO 8
<211> LENGTH: 9
<212> TYPE: PRT
<213> ORGANISM: Homo sapiens

<400> SEQUENCE: 8

Ser Leu Phe Ala Glu Thr Ile Trp Val
1               5

<210> SEQ ID NO 9
<211> LENGTH: 9
<212> TYPE: PRT
<213> ORGANISM: Homo sapiens

<400> SEQUENCE: 9

Met Leu Ile Ala Met Tyr Phe Tyr Thr
1               5

<210> SEQ ID NO 10
<211> LENGTH: 9
<212> TYPE: PRT
<213> ORGANISM: Homo sapiens

<400> SEQUENCE: 10

Leu Met Trp Thr Leu Pro Val Met Leu
1               5

<210> SEQ ID NO 11
<211> LENGTH: 9
<212> TYPE: PRT
<213> ORGANISM: Homo sapiens

<400> SEQUENCE: 11

Met Leu Ile Val Tyr Ile Phe Glu Cys
1               5

<210> SEQ ID NO 12
<211> LENGTH: 9
<212> TYPE: PRT
<213> ORGANISM: Homo sapiens

<400> SEQUENCE: 12

Tyr Ile Phe Glu Cys Ala Ser Cys Ile
1               5

<210> SEQ ID NO 13
<211> LENGTH: 9
<212> TYPE: PRT
<213> ORGANISM: Homo sapiens

<400> SEQUENCE: 13

Leu Val Leu Met Leu Ile Val Tyr Ile
1               5

<210> SEQ ID NO 14
<211> LENGTH: 9
<212> TYPE: PRT
<213> ORGANISM: Homo sapiens

<400> SEQUENCE: 14

Ala Leu Cys Arg Arg Arg Ser Met Val
1               5
```

```
<210> SEQ ID NO 15
<211> LENGTH: 9
<212> TYPE: PRT
<213> ORGANISM: Homo sapiens

<400> SEQUENCE: 15

Leu Leu Ser Gly Leu Ser Leu Phe Ala
1               5

<210> SEQ ID NO 16
<211> LENGTH: 9
<212> TYPE: PRT
<213> ORGANISM: Homo sapiens

<400> SEQUENCE: 16

Phe Leu Leu Val Val Gly Leu Ile Val
1               5

<210> SEQ ID NO 17
<211> LENGTH: 9
<212> TYPE: PRT
<213> ORGANISM: Homo sapiens

<400> SEQUENCE: 17

Leu Val Val Gly Leu Ile Val Ala Leu
1               5

<210> SEQ ID NO 18
<211> LENGTH: 9
<212> TYPE: PRT
<213> ORGANISM: Homo sapiens

<400> SEQUENCE: 18

Lys Val Val Lys Ser Asp Phe Val Val
1               5

<210> SEQ ID NO 19
<211> LENGTH: 9
<212> TYPE: PRT
<213> ORGANISM: Homo sapiens

<400> SEQUENCE: 19

Thr Leu Pro Val Gln Thr Leu Pro Leu
1               5

<210> SEQ ID NO 20
<211> LENGTH: 9
<212> TYPE: PRT
<213> ORGANISM: Homo sapiens

<400> SEQUENCE: 20

Asp Leu His Val Ile Ser Asn Asp Val
1               5

<210> SEQ ID NO 21
<211> LENGTH: 9
<212> TYPE: PRT
<213> ORGANISM: Homo sapiens

<400> SEQUENCE: 21

Val Leu Val His Pro Gln Trp Val Leu
1               5

<210> SEQ ID NO 22
```

```
<211> LENGTH: 9
<212> TYPE: PRT
<213> ORGANISM: Homo sapiens

<400> SEQUENCE: 22

Phe Leu Arg Pro Gly Asp Asp Ser Ser
1               5

<210> SEQ ID NO 23
<211> LENGTH: 9
<212> TYPE: PRT
<213> ORGANISM: Homo sapiens

<400> SEQUENCE: 23

Ala Leu Gly Thr Thr Cys Tyr Ala Ser
1               5

<210> SEQ ID NO 24
<211> LENGTH: 9
<212> TYPE: PRT
<213> ORGANISM: Homo sapiens

<400> SEQUENCE: 24

Lys Leu Gln Cys Val Asp Leu His Val
1               5

<210> SEQ ID NO 25
<211> LENGTH: 9
<212> TYPE: PRT
<213> ORGANISM: Homo sapiens

<400> SEQUENCE: 25

Glu Leu Ala His Tyr Asp Val Leu Leu
1               5

<210> SEQ ID NO 26
<211> LENGTH: 9
<212> TYPE: PRT
<213> ORGANISM: Homo sapiens

<400> SEQUENCE: 26

Asn Leu Asn Gly Ala Gly Asp Pro Leu
1               5

<210> SEQ ID NO 27
<211> LENGTH: 9
<212> TYPE: PRT
<213> ORGANISM: Homo sapiens

<400> SEQUENCE: 27

Thr Leu Arg Val Asp Cys Thr Pro Leu
1               5

<210> SEQ ID NO 28
<211> LENGTH: 9
<212> TYPE: PRT
<213> ORGANISM: Homo sapiens

<400> SEQUENCE: 28

Met Met Asn Asp Gln Leu Met Phe Leu
1               5

<210> SEQ ID NO 29
<211> LENGTH: 9
<212> TYPE: PRT
```

<213> ORGANISM: Homo sapiens

<400> SEQUENCE: 29

Ala Leu Phe Asp Ile Glu Ser Lys Val
1               5

<210> SEQ ID NO 30
<211> LENGTH: 9
<212> TYPE: PRT
<213> ORGANISM: Homo sapiens

<400> SEQUENCE: 30

Leu Leu His Glu Thr Asp Ser Ala Val
1               5

<210> SEQ ID NO 31
<211> LENGTH: 9
<212> TYPE: PRT
<213> ORGANISM: Homo sapiens

<400> SEQUENCE: 31

Val Leu Ala Lys Glu Leu Lys Phe Val
1               5

<210> SEQ ID NO 32
<211> LENGTH: 9
<212> TYPE: PRT
<213> ORGANISM: Homo sapiens

<400> SEQUENCE: 32

Ile Leu Leu Trp Gln Pro Ile Pro Val
1               5

<210> SEQ ID NO 33
<211> LENGTH: 9
<212> TYPE: PRT
<213> ORGANISM: Homo sapiens

<400> SEQUENCE: 33

Asp Leu Phe Gly Ile Trp Ser Lys Val
1               5

<210> SEQ ID NO 34
<211> LENGTH: 9
<212> TYPE: PRT
<213> ORGANISM: Homo sapiens

<400> SEQUENCE: 34

Pro Leu Glu Arg Phe Ala Glu Leu Val
1               5

<210> SEQ ID NO 35
<211> LENGTH: 9
<212> TYPE: PRT
<213> ORGANISM: Homo sapiens

<400> SEQUENCE: 35

Lys Gln Gly Asn Phe Asn Ala Trp Val
1               5

<210> SEQ ID NO 36
<211> LENGTH: 9
<212> TYPE: PRT
<213> ORGANISM: Homo sapiens

```
<400> SEQUENCE: 36

Asn Leu Leu Arg Arg Met Trp Val Thr
1               5

<210> SEQ ID NO 37
<211> LENGTH: 9
<212> TYPE: PRT
<213> ORGANISM: Homo sapiens

<400> SEQUENCE: 37

Asn Leu Phe Glu Thr Pro Ile Leu Ala
1               5

<210> SEQ ID NO 38
<211> LENGTH: 9
<212> TYPE: PRT
<213> ORGANISM: Homo sapiens

<400> SEQUENCE: 38

Asn Leu Phe Glu Thr Pro Val Glu Ala
1               5

<210> SEQ ID NO 39
<211> LENGTH: 9
<212> TYPE: PRT
<213> ORGANISM: Homo sapiens

<400> SEQUENCE: 39

Gly Leu Gln His Trp Val Pro Glu Leu
1               5

<210> SEQ ID NO 40
<211> LENGTH: 9
<212> TYPE: PRT
<213> ORGANISM: Homo sapiens

<400> SEQUENCE: 40

Val Gln Phe Val Ala Ser Tyr Lys Val
1               5

<210> SEQ ID NO 41
<211> LENGTH: 9
<212> TYPE: PRT
<213> ORGANISM: Homo sapiens

<400> SEQUENCE: 41

Arg Leu Leu Ala Ala Leu Cys Gly Ala
1               5

<210> SEQ ID NO 42
<211> LENGTH: 9
<212> TYPE: PRT
<213> ORGANISM: Homo sapiens

<400> SEQUENCE: 42

Leu Leu Leu Leu Thr Val Leu Thr Val
1               5

<210> SEQ ID NO 43
<211> LENGTH: 9
<212> TYPE: PRT
<213> ORGANISM: Homo sapiens

<400> SEQUENCE: 43
```

```
Leu Leu Leu Thr Val Leu Thr Val Val
1               5

<210> SEQ ID NO 44
<211> LENGTH: 9
<212> TYPE: PRT
<213> ORGANISM: Homo sapiens

<400> SEQUENCE: 44

Phe Leu Ser Phe His Ile Ser Asn Leu
1               5

<210> SEQ ID NO 45
<211> LENGTH: 9
<212> TYPE: PRT
<213> ORGANISM: Homo sapiens

<400> SEQUENCE: 45

Leu Leu Val Leu Val Cys Val Leu Val
1               5

<210> SEQ ID NO 46
<211> LENGTH: 9
<212> TYPE: PRT
<213> ORGANISM: Homo sapiens

<400> SEQUENCE: 46

Ala Leu Leu Val Leu Val Cys Val Leu
1               5

<210> SEQ ID NO 47
<211> LENGTH: 9
<212> TYPE: PRT
<213> ORGANISM: Homo sapiens

<400> SEQUENCE: 47

Ser Leu Ser Tyr Thr Asn Pro Ala Val
1               5

<210> SEQ ID NO 48
<211> LENGTH: 9
<212> TYPE: PRT
<213> ORGANISM: Homo sapiens

<400> SEQUENCE: 48

Asn Leu Thr Ile Ser Asp Val Ser Val
1               5

<210> SEQ ID NO 49
<211> LENGTH: 9
<212> TYPE: PRT
<213> ORGANISM: Homo sapiens

<400> SEQUENCE: 49

Ala Leu Ala Ser Thr Ala Pro Pro Val
1               5

<210> SEQ ID NO 50
<211> LENGTH: 9
<212> TYPE: PRT
<213> ORGANISM: Homo sapiens

<400> SEQUENCE: 50

Ala Ile Leu Cys Trp Thr Phe Trp Val
1               5
```

```
<210> SEQ ID NO 51
<211> LENGTH: 9
<212> TYPE: PRT
<213> ORGANISM: Homo sapiens

<400> SEQUENCE: 51

Phe Ile Leu Met Phe Ile Val Tyr Ala
1               5

<210> SEQ ID NO 52
<211> LENGTH: 9
<212> TYPE: PRT
<213> ORGANISM: Homo sapiens

<400> SEQUENCE: 52

Leu Thr Ala Glu Cys Ile Phe Phe Val
1               5

<210> SEQ ID NO 53
<211> LENGTH: 9
<212> TYPE: PRT
<213> ORGANISM: Homo sapiens

<400> SEQUENCE: 53

Met Leu Gln Asp Asn Cys Cys Gly Val
1               5

<210> SEQ ID NO 54
<211> LENGTH: 9
<212> TYPE: PRT
<213> ORGANISM: Homo sapiens

<400> SEQUENCE: 54

Ile Leu Cys Trp Thr Phe Trp Val Leu
1               5

<210> SEQ ID NO 55
<211> LENGTH: 9
<212> TYPE: PRT
<213> ORGANISM: Homo sapiens

<400> SEQUENCE: 55

Lys Ile Leu Leu Ala Tyr Phe Ile Leu
1               5

<210> SEQ ID NO 56
<211> LENGTH: 9
<212> TYPE: PRT
<213> ORGANISM: Homo sapiens

<400> SEQUENCE: 56

Phe Val Gly Ile Cys Leu Phe Cys Leu
1               5

<210> SEQ ID NO 57
<211> LENGTH: 9
<212> TYPE: PRT
<213> ORGANISM: Homo sapiens

<400> SEQUENCE: 57

Val Leu Leu Ser Val Ala Met Phe Leu
1               5
```

```
<210> SEQ ID NO 58
<211> LENGTH: 9
<212> TYPE: PRT
<213> ORGANISM: Homo sapiens

<400> SEQUENCE: 58

Leu Leu Ser Val Ala Met Phe Leu Leu
1               5

<210> SEQ ID NO 59
<211> LENGTH: 9
<212> TYPE: PRT
<213> ORGANISM: Homo sapiens

<400> SEQUENCE: 59

Ile Leu Gly Ser Leu Pro Phe Phe Leu
1               5

<210> SEQ ID NO 60
<211> LENGTH: 9
<212> TYPE: PRT
<213> ORGANISM: Homo sapiens

<400> SEQUENCE: 60

Ile Leu Asn Ala Tyr Leu Val Arg Val
1               5

<210> SEQ ID NO 61
<211> LENGTH: 9
<212> TYPE: PRT
<213> ORGANISM: Homo sapiens

<400> SEQUENCE: 61

Phe Leu Leu Val Gly Phe Ala Gly Ala
1               5

<210> SEQ ID NO 62
<211> LENGTH: 9
<212> TYPE: PRT
<213> ORGANISM: Homo sapiens

<400> SEQUENCE: 62

Asn Leu Gln Pro Gln Leu Ala Ser Val
1               5

<210> SEQ ID NO 63
<211> LENGTH: 9
<212> TYPE: PRT
<213> ORGANISM: Homo sapiens

<400> SEQUENCE: 63

Cys Met Phe Asp Ser Lys Glu Ala Leu
1               5

<210> SEQ ID NO 64
<211> LENGTH: 9
<212> TYPE: PRT
<213> ORGANISM: Homo sapiens

<400> SEQUENCE: 64

Tyr Leu Tyr Val Leu Val Asp Ser Ala
1               5

<210> SEQ ID NO 65
<211> LENGTH: 9
```

```
<212> TYPE: PRT
<213> ORGANISM: Homo sapiens

<400> SEQUENCE: 65

Tyr Met Asp Gly Thr Met Ser Gln Val
1               5

<210> SEQ ID NO 66
<211> LENGTH: 9
<212> TYPE: PRT
<213> ORGANISM: Homo sapiens

<400> SEQUENCE: 66

Lys Met Ala Arg Phe Ser Tyr Ser Val
1               5

<210> SEQ ID NO 67
<211> LENGTH: 9
<212> TYPE: PRT
<213> ORGANISM: Homo sapiens

<400> SEQUENCE: 67

Gly Leu Val Met Asp Glu His Leu Val
1               5

<210> SEQ ID NO 68
<211> LENGTH: 9
<212> TYPE: PRT
<213> ORGANISM: Homo sapiens

<400> SEQUENCE: 68

Phe Leu Pro Gly Cys Asp Gly Leu Val
1               5

<210> SEQ ID NO 69
<211> LENGTH: 9
<212> TYPE: PRT
<213> ORGANISM: Homo sapiens

<400> SEQUENCE: 69

Cys Met Leu Gly Ser Phe Cys Ala Cys
1               5

<210> SEQ ID NO 70
<211> LENGTH: 9
<212> TYPE: PRT
<213> ORGANISM: Homo sapiens

<400> SEQUENCE: 70

Tyr Leu Ala Phe Arg Asp Asp Ser Ile
1               5

<210> SEQ ID NO 71
<211> LENGTH: 9
<212> TYPE: PRT
<213> ORGANISM: Homo sapiens

<400> SEQUENCE: 71

Trp Leu Pro Lys Lys Cys Ser Leu Cys
1               5

<210> SEQ ID NO 72
<211> LENGTH: 9
<212> TYPE: PRT
<213> ORGANISM: Homo sapiens
```

```
<400> SEQUENCE: 72

Cys Leu Asn Gly Gly Thr Cys Met Leu
1               5

<210> SEQ ID NO 73
<211> LENGTH: 9
<212> TYPE: PRT
<213> ORGANISM: Homo sapiens

<400> SEQUENCE: 73

Met Leu Val Gly Ile Cys Leu Ser Ile
1               5

<210> SEQ ID NO 74
<211> LENGTH: 9
<212> TYPE: PRT
<213> ORGANISM: Homo sapiens

<400> SEQUENCE: 74

Phe Glu Leu Gly Leu Val Ala Gly Leu
1               5

<210> SEQ ID NO 75
<211> LENGTH: 9
<212> TYPE: PRT
<213> ORGANISM: Homo sapiens

<400> SEQUENCE: 75

Lys Met Val Arg Phe Ser Tyr Ser Val
1               5

<210> SEQ ID NO 76
<211> LENGTH: 9
<212> TYPE: PRT
<213> ORGANISM: Homo sapiens

<400> SEQUENCE: 76

Cys Leu Asn Glu Gly Thr Cys Met Leu
1               5

<210> SEQ ID NO 77
<211> LENGTH: 9
<212> TYPE: PRT
<213> ORGANISM: Homo sapiens

<400> SEQUENCE: 77

Met Leu Ala Gly Ile Cys Leu Ser Ile
1               5

<210> SEQ ID NO 78
<211> LENGTH: 387
<212> TYPE: PRT
<213> ORGANISM: Human Lactaherin

<400> SEQUENCE: 78

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
```

-continued

```
                50                  55                  60
His Cys Glu Thr Lys Cys Val Glu Pro Leu Gly Met Glu Asn Gly Asn
 65                  70                  75                  80

Ile Ala Asn Ser Gln Ile Ala Ala Ser Ser Val Arg Val Thr Phe Leu
                 85                  90                  95

Gly Leu Gln His Trp Val Pro Glu Leu Ala Arg Leu Asn Arg Ala Gly
                100                 105                 110

Met Val Asn Ala Trp Thr Pro Ser Ser Asn Asp Asp Asn Pro Trp Ile
                115                 120                 125

Gln Val Asn Leu Leu Arg Arg Met Trp Val Thr Gly Val Val Thr Gln
130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
                180                 185                 190

Val Asn Leu Phe Glu Thr Pro Val Glu Ala Gln Tyr Val Arg Leu Tyr
                195                 200                 205

Pro Thr Ser Cys His Thr Ala Cys Thr Leu Arg Phe Glu Leu Leu Gly
210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
                260                 265                 270

Gly Asn Phe Asn Ala Trp Val Ala Gly Ser Tyr Gly Asn Asp Gln Trp
                275                 280                 285

Leu Gln Val Asp Leu Gly Ser Ser Lys Glu Val Thr Gly Ile Ile Thr
                290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
                340                 345                 350

His Lys Lys Asn Leu Phe Glu Thr Pro Ile Leu Ala Arg Tyr Val Arg
                355                 360                 365

Ile Leu Pro Val Ala Trp His Asn Arg Ile Ala Leu Arg Leu Glu Leu
                370                 375                 380

Leu Gly Cys
385
```